US010188713B2

(12) United States Patent
Vile et al.

(10) Patent No.: US 10,188,713 B2
(45) Date of Patent: Jan. 29, 2019

(54) METHODS AND MATERIALS FOR TREATING CANCER

(71) Applicants: Mayo Foundation for Medical Education and Research, Rochester, MN (US); University of Leeds, Leeds (GB)

(72) Inventors: Richard G. Vile, Rochester, MN (US); Timothy J. Kottke, Oronoco, MN (US); Jill M. Thompson, Stewartville, MN (US); Jose S. Pulido, Rochester, MN (US); Alan A. Melcher, Leeds (GB); Peter Selby, Leeds (GB)

(73) Assignees: Mayo Foundation for Medical Education and Research, Rochester, MN (US); University of Leeds, Leeds (GB)

( * ) Notice: Subject to any disclaimer, the term of this patent is extended or adjusted under 35 U.S.C. 154(b) by 40 days.

(21) Appl. No.: 15/126,338

(22) PCT Filed: Mar. 19, 2015

(86) PCT No.: PCT/US2015/021576
§ 371 (c)(1),
(2) Date: Sep. 15, 2016

(87) PCT Pub. No.: WO2015/143223
PCT Pub. Date: Sep. 24, 2015

(65) Prior Publication Data
US 2017/0080066 A1  Mar. 23, 2017

Related U.S. Application Data

(60) Provisional application No. 61/955,677, filed on Mar. 19, 2014.

(51) Int. Cl.
*A61K 39/00* (2006.01)
*A61K 39/39* (2006.01)
*A61K 39/395* (2006.01)
*C12N 7/00* (2006.01)

(52) U.S. Cl.
CPC .......... *A61K 39/0011* (2013.01); *A61K 39/39* (2013.01); *A61K 39/3955* (2013.01); *C12N 7/00* (2013.01); *A61K 2039/505* (2013.01); *A61K 2039/5256* (2013.01); *A61K 2039/53* (2013.01); *A61K 2039/54* (2013.01); *A61K 2039/552* (2013.01); *A61K 2039/55516* (2013.01); *A61K 2039/70* (2013.01); *C12N 2760/20243* (2013.01)

(58) Field of Classification Search
CPC . A61K 39/0011; A61K 39/3955; A61K 39/39
See application file for complete search history.

(56) References Cited

U.S. PATENT DOCUMENTS

| | | | |
|---|---|---|---|
| 5,695,963 A | 12/1997 | McKnight et al. | |
| 6,140,053 A | 10/2000 | Koster | |
| 2010/0121033 A1* | 5/2010 | Camphausen | C07K 14/78 530/363 |
| 2010/0129389 A1 | 5/2010 | Ware | |
| 2010/0168206 A1 | 7/2010 | Gollob et al. | |
| 2010/0221349 A1 | 9/2010 | Fuller | |
| 2012/0258046 A1 | 10/2012 | Mutzke | |
| 2012/0308484 A1 | 12/2012 | Szalay et al. | |
| 2012/0308601 A1 | 12/2012 | Vile et al. | |
| 2013/0287772 A1 | 10/2013 | Halbert et al. | |
| 2015/0064218 A1 | 3/2015 | Pulido et al. | |
| 2017/0080065 A1 | 3/2017 | Pulido et al. | |
| 2017/0143813 A1 | 5/2017 | Pulido et al. | |

FOREIGN PATENT DOCUMENTS

| WO | WO 2008/109825 | 9/2008 |
|---|---|---|
| WO | WO 2011/100468 | 8/2011 |
| WO | WO 2013/036201 | 3/2013 |
| WO | WO 2013/138697 | 9/2013 |
| WO | WO 2013/173223 | 11/2013 |
| WO | WO 2013/178344 | 12/2013 |

OTHER PUBLICATIONS

De Gruijl et al., "Whole-cell cancer vaccination: from autologous to allogeneic tumor- and dendritic cell-based vaccines," Cancer Immunology Immunotherapy., 57:1569-1577, 2008.
Anonymous: "Programme replicating oncolytic virus therapeutics 2013," Jun. 1, 2013, pp. 1-5, Retrieved from the Internet: URL: http://www.iovmc.org/2013/programme/ Retrieved on Sep. 14, 2017.
Extended European Search report for International Application No. EP15765847.7, dated Oct. 13, 2017, 7 pages.
Gessi et al., "GNA11 and N-RAS mutations: alternatives for MAPK pathway activating GNAQ mutations in primary melanocytic tumors of the central nervous system," *Neuropathology Applied Neurobiology*., 39(4):417-425, Apr. 25, 2013.
Partial Supplementary European Search Report for International Application No. 15765220.7, dated Oct. 23, 2017, 26 pages.
Woodman., "Metastatic uveal melanoma: biology and emerging treatments," *Cancer J.*, 18(2):148-152, Feb. 26, 2014.
Lee et al., "A comprehensive guide to the MAGE family of ubiquitin ligases," J Mol Biol., 429:1114-1142, Apr. 2017.

(Continued)

*Primary Examiner* — Antonio Galisteo Gonzalez
(74) *Attorney, Agent, or Firm* — Fish & Richardson P.C.

(57) ABSTRACT

This document provides methods and materials for treating cancer. For example, methods and materials for identifying antigens and combinations of antigens that can be used to treat cancer as well as combinations of antigens having the ability to reduce established tumors (e.g., gliomas) within a mammal (e.g., a human) are provided. In general, one aspect of this document features a composition comprising, or consisting essentially of, nucleic acid encoding HIF-2a, SOX-10, C-MYC, and TYRP-1, wherein the composition comprises less than 100 separate nucleic acid molecules.

2 Claims, 43 Drawing Sheets
Specification includes a Sequence Listing.

(56) References Cited

OTHER PUBLICATIONS

Lucas et al., "A new MAGE gene with ubiquitous expression does not code for known MAGE antigens recognized by T cells," Cancer Research., 59:4100-4103, Aug. 15, 1999.
Sang et al. Melanoma-associated antigen genes—An update. Cancer Letters, vol. 302, pp. 85-90, 2011. (Year: 2011).
Tseng et al., "Letter to the Editor: Long-term survivors after immunotherapy for metastatic melanoma," Immunology Letters., vol. 139:117-118, Feb. 2011.
Drape et al. Epidermal DNA vaccine for influenza is immunogenic in humans. Vaccine, vol. 24, pp. 4475-4481, 2006.
Kottke et al. Broad antigenic coverage induced by vaccination with virus-based cDNA libraries cures established tumors. Nature Medicine, vol. 17, No. 7, pp. 854-860, Jul. 2011, published online Jun. 19, 2011.
Nucleic Acids and Protein Calculations: DNA Molar Conversions, printed from http://www.genscript.com/converstion.html, as p. 1/1 on Apr. 24, 2017.
Rochard et al. Genetic immunization with plasmid DNA mediated by electrotransfer. Human Gene Therapy, vol. 22, pp. 789-798, Jul. 2011.
Steitz et al. Genetic immunization of mice with human tyrosinase-related protein 2: Implications for the immunotherapy of melanoma. International Journal of Cancer, vol. 86, pp. 89-94, 2000.
Yang et al. Dendritic cell-directed lentivector vaccine induces antigen-specific immune responses against murine melanoma. Cancer Gene Therapy, vol. 18, pp. 370-380, 2011.
GenBank® Accession No. AAB29640, GI: 544859, "N-ras [*Homo sapiens*]," Sep. 23, 1994, 1 page.
GenBank® Accession No. AC_000025.1, GI: 83280973, "Mus musculus strain mixed chromosome 3, alternate assembly Mm_Celera, whole genome shotgun sequence," Oct. 19, 2010, 2 pages.
GenBank® Accession No. AF047043.1, "Mus musculus Sox-10 protein (Sox10) mRNA, complete cds," Jun. 27, 1998, 2 pages.
GenBank® Accession No. AF063658 GI: 3132832, "*Homo sapiens* vascular endothelial growth factor receptor 2 (KDR) mRNA, complete cds," May 16, 1998, 2 pages.
GenBank® Accession No. AF399931.1 GI: 33307711, "*Homo sapiens* P-glycoprotein (ABCB1) mRNA, complete cds," Jun. 10, 2004, 2 pages.
GenBank® Accession No. AF493896.1 GI: 20147684, "*Homo sapiens* guanine nucleotide binding protein alpha q (GNAQ) mRNA, complete cds," Apr. 14, 2002, 1 pages.
GenBank® Accession No. AF493919.1 GI: 20147730, "*Homo sapiens* Ras family small GTP binding protein N-Ras (NRAS) mRNA, complete cds," Apr. 14, 2002, 1 page.
GenBank® Accession No. AY101192.1 GI: 21429238, "*Homo sapiens* CD44 antigen (CD44) mRNA, complete cds," Jun. 15, 2002, 2 pages.
GenBank® Accession No. AY101193.1 GI: 21429240, "*Homo sapiens* CD44 antigen (CD44) mRNA, complete cds," Jun. 15, 2002, 2 pages.
GenBank® Accession No. AY234788.1 GI: 34539754, "*Homo sapiens* P-glycoprotein ABCB5 mRNA, complete cds," Nov. 17, 2003, 2 pages.
GenBank® Accession No. AY425006.1 GI: 40795902, "*Homo sapiens* P-glycoprotein 1 (ABCB1) mRNA, partial cds, alternatively spliced," Apr. 27, 2004, 1 page.
GenBank® Accession No. AY864315.1 GI: 57791235, "Mus musculus strain BALB/c multidrug resistance protein 1a (Abcb1a) mRNA, complete cds," Jan. 19, 2005, 2 pages.
GenBank® Accession No. BC057583.1 GI: 34785834, "Mus musculus guanine nucleotide binding protein, alpha q polypeptide, mRNA (cDNA clone MGC:67083 IMAGE:6408959), complete cds," Aug. 11, 2006, 3 pages.
GenBank® Accession No. BC061634.1 GI: 38197294, "Mus musculus Y box protein 1, mRNA (cDNA clone MGC:68144 IMAGE:6530605), complete cds," Sep. 1, 2006, 3 pages.
GenBank® Accession No. BC071708.1 GI: 47940505, "*Homo sapiens* Y box binding protein 1, mRNA (cDNA clone MGC:87995 IMAGE:4361396), complete cds," Jun. 23, 2006, 3 pages.
GenBank® Accession No. BC076598.1 GI: 49903295, "Mus musculus tyrosinase-related protein 1, mRNA (cDNA clone MGC:96635 IMAGE:30613975), complete cds," Jul. 15, 2006, 3 pages.
GenBank® Accession No. BT020029 GI: 54696919, "*Homo sapiens* SRY (sex determining region Y)-box 10 mRNA, complete cds," Oct. 28, 2004, 2 pages.
GenBank® Accession No. CAG28611, GI: 47115303, "TYRP1 [*Homo sapiens*]," Oct 16, 2008, 2 pages.
GenBank® Accession No. CR407683.1 GI: 47115302, "*Homo sapiens* full open reading frame cDNA clone RZPDo834D033D for gene TYRP1, tyrosinase-related protein 1 complete cds, without stopcodon," Oct. 16, 2008, 2 pages.
GenBank® Accession No. EU854148.1 GI: 194740429, "*Homo sapiens* multidrug resistance protein 1 mRNA, complete cds, alternatively spliced," Aug. 5, 2008, 2 pages.
GenBank® Accession No. EU884114.1 GI: 215400615, "Mus musculus strain C57BL/6 soluble vascular endothelial growth factor receptor 2 mRNA, complete cds," Nov. 15, 2010, 2 pages.
GenBank® Accession No. J04444, GI: 181239, "Human cytochrome c-1 gene, complete cds," Nov. 2, 1994, 3 pages.
GenBank® Accession No. J05114 GI: 37092, "Human mRNA for transforming growth factor-beta(TGF-beta)," Mar. 27, 1995, 2 pages.
GenBank® Accession No. JQ655148.1 GI: 406817019, "Mus musculus P-glycoprotein (Abcb5) mRNA, complete cds," Feb. 9, 2014, 2 pages.
GenBank® Accession No. M13177.1 GI: 201952, "Mouse transforming growth factor beta mRNA (TGF-beta), complete cds," Apr. 27, 1993, 2 pages.
GenBank® Accession No. M23234.1 GI: 187501, "Human membrane glycoprotein P (mdr3) mRNA, complete cds," Jun. 11, 1993, 2 pages.
GenBank® Accession No. M24417.1 GI: 2000329, "Mouse phosphoglycoprotein mdr1a mRNA, 3' end," Nov. 18, 1993, 2 pages.
GenBank® Accession No. M33581.1 GI: 199104, "Mouse P-glycoprotein (mdr1a) mRNA, complete cds," Apr. 27, 1993, 3 pages.
GenBank® Accession No. M62867 GI: 199820, "Mouse Y box transcription factor (MSY-1) mRNA, complete cds," Mar. 7, 1995, 2 pages.
GenBank® Accession No. NC_000069.6 GI: 372099107, "Mus musculus strain C57BL/6J chromosome 3, MGSCv37 C57BL/6J," Oct. 19, 2010, 1 page.
GenBank® Accession No. NM_009863 GI: 409168309, "Mus musculus cell division cycle 7 (S. cerevisiae) (Cdc7), transcript variant 2, mRNA," Oct. 18, 2012, 4 pages.
GenBank® Accession No. NM_000550, GI: 169881242, "*Homo sapiens* tyrosinase-related protein 1 (TYRP1), mRNA," Mar. 12, 2011, 4 pages.
GenBank® Accession No. NM_001067.3 GI: 300193028, "*Homo sapiens* topoisomerase (DNA) II alpha 170kDa (TOP2A), mRNA," Mar. 11, 2011, 9 pages.
GenBank® Accession No. NM_001134419.1 GI: 197313664, "*Homo sapiens* cell division cycle 7 (CDC7), transcript variant 2, mRNA," Mar. 10, 2011, 5 pages.
GenBank® Accession No. NM_001134420.1 GI: 197313666, "*Homo sapiens* cell division cycle 7 homolog (S. cerevisiae) (CDC7), transcript variant 3, mRNA," Mar. 11, 2011, 5 pages.
GenBank® Accession No. NM_001163941.1 GI: 255708476, "*Homo sapiens* ATP-binding cassette, sub-family B (MDR/TAP), member 5 (ABCB5), transcript variant 1, mRNA," Mar. 11, 2011, 6 pages.
GenBank® Accession No. NM_001163942.1 GI: 255708370, "*Homo sapiens* ATP-binding cassette, sub-family B (MDR/TAP), member 5 (ABCB5), transcript variant 3, mRNA," Mar. 11, 2011, 4 pages.
GenBank® Accession No. NM_001163993.2 GI: 574957217, "*Homo sapiens* ATP-binding cassette, sub-family B (MDR/TAP), member 5 (ABCB5), transcript variant 4, mRNA," Mar. 12, 2011, 4 pages.
GenBank® Accession No. NM_001177352.1 GI: 293629263, "Mus musculus myelocytomatosis oncogene (MYC), transcript variant 1, mRNA," Mar. 11, 2011, 5 pages.

(56) References Cited

OTHER PUBLICATIONS

GenBank® Accession No. NM_001177353.1 GI: 293629266, "Mus musculus myelocytomatosis oncogene (Myc), transcript variant 2, mRNA," Mar. 13, 2011, 5 pages.
GenBank® Accession No. NM_001177354.1 GI: 293629269, "Mus musculus myelocytomatosis oncogene (Myc), transcript variant 2, mRNA," Mar. 11, 2011, 5 pages.
GenBank® Accession No. NM_001177787 GI: 295293147, "Mus musculus CD44 antigen (Cd44), transcript variant 6, mRNA," Mar. 12, 2011, 5 pages.
GenBank® Accession No. NM_001282014.1 GI: 530537243, "Mus musculus tyrosinase-related protein 1 (Tyrp1), transcript variant 2, mRNA," Aug. 14, 2013, 4 pages.
GenBank® Accession No. NM_001282015.1 GI: 530537245, "Mus musculus tyrosinase-related protein 1 (Tyrp1), transcript variant 3, mRNA," Aug. 14, 2013, 4 pages.
GenBank® Accession No. NM_001430 GI: 262527236, "*Homo sapiens* endothelial PAS domain protein 1 (EPAS1), mRNA," Mar. 13, 2011, 6 pages.
GenBank® Accession No. NM_002154, GI: 38327038, "*Homo sapiens* heat shock 70kDa protein 4 (HSPA4), mRNA," Feb. 15, 2009, 5 pages.
GenBank® Accession No. NM_002524, GI: 185134767, "*Homo sapiens* neuroblastoma RAS viral (v-ras) oncogene homolog (NRAS), mRNA," Mar. 13, 2011, 5 pages.
GenBank® Accession No. NM_002524.4 GI: 334688826, "*Homo sapiens* neuroblastoma RAS viral (v-ras) oncogene homolog (NRAS), mRNA," Jun. 2, 2011, 5 pages.
GenBank® Accession No. NM_003503.3 GI: 197313663, "*Homo sapiens* cell division cycle 7 homolog (S. cerevisiae) (CDC7), transcript variant 1, mRNA," Mar. 13, 2011, 5 pages.
GenBank® Accession No. NM_004333.4 GI: 187608632, "*Homo sapiens* v-raf murine sarcoma viral oncogene homolog B1 (BRAF), mRNA," Mar. 13, 2011, 7 pages.
GenBank® Accession No. NM_004559.3 GI: 109134359, "*Homo sapiens* Y box binding protein 1 (YBX1), mRNA," Mar. 13, 2011, 5 pages.
GenBank® Accession No. NM_008139.5 GI: 145966786, "Mus musculus guanine nucleotide binding protein, alpha q polypeptide (Gnaq), mRNA," Mar. 12, 2011, 5 pages.
GenBank® Accession No. NM_009863 GI: 409168309, "Mus musculus cell division cycle 7 (S. cerevisiae) (Cdc7), mRNA," Mar. 10, 2012, 4 pages.
GenBank® Accession No. NM_010849.4 GI: 100913213, "Mus musculus myelocytomatosis oncogene (Myc), transcript variant 1, mRNA," Mar. 11, 2011, 5 pages.
GenBank® Accession No. NM_010937.2 GI: 372099107, "Mus musculus neuroblastoma ras oncogene (Nras), mRNA," Mar. 13, 2011, 4 pages.
GenBank® Accession No. NM_011075 GI: 161169006, "Mus musculus ATP-binding cassette, sub-family B (MDR/TAP), member 1B (Abcb1b), mRNA," Mar. 10, 2011, 7 pages.
GenBank® Accession No. NM_011623, "Mus musculus topoisomerase (DNA) II alpha (Top2a), mRNA," Mar. 11, 2012, 7 pages.
GenBank® Accession No. NM_011732.2 GI: 113205058, "Mus musculus Y box protein 1 (Ybx1), mRNA," Mar. 13, 2011, 5 pages.
GenBank® Accession No. NM_029961 XM_906632 GI: 255708374, "Mus musculus ATP-binding cassette, sub-family B (MDR/TAP), member 5 (Abcb5), mRNA," Mar. 11, 2011, 4 pages.
GenBank® Accession No. NM_031202.3 GI: 530537240, "Mus musculus tyrosinase-related protein 1 (Tyrp1), mRNA," Mar. 11, 2011, 4 pages.
GenBank® Accession No. NM_139294.5 GI: 153791903, "Mus musculus Braf transforming gene (Braf), mRNA," Feb. 27, 2011, 7 pages.
GenBank® Accession No. NM_178559.5 GI: 255708475, "*Homo sapiens* ATP-binding cassette, sub-family B (MDR/TAP), member 5 (ABCB5), transcript variant 2, mRNA," Mar. 13, 2011, 6 pages.
GenBank® Accession No. NP_002145, GI: 38327039, "heat shock 70kDa protein 4 [*Homo sapiens*]," Feb. 15, 2009, 2 pages.
GenBank® Accession No. NP_061820, GI: 11128019, "cytochrome c [*Homo sapiens*]," Mar. 11, 2011, 2 pages.
GenBank® Accession No. NW_004078038.1, "*Homo sapiens* chromosome 9 genomic scaffold, alternate assembly CHM1_1.0, whole genome shotgun sequence," Nov. 2, 2012, 4 pages.
GenBank® Accession No. U40038.1 GI: 1181670, "Human GTP-binding protein alpha q subunit (GNAQ) mRNA, complete cds," Feb. 7, 1996, 2 pages.
GenBank® Accession No. V00568 GI: 34815, "Human mRNA encoding the c-myc oncogene," Oct. 7, 2008, 2 pages.
GenBank® Accession No. X02812 GI: 37092, "Human mRNA for transforming growth factor-beta (TGF-beta)," Mar. 27, 1995, 2 pages.
GenBank® Accession No. X51420.1 GI: 37512, "*Homo sapiens* mRNA for tyrosinase-related protein precursor (TYRP1)," Oct. 7, 2008, 2 pages.
GenBank® Accession No. X57621.1 GI: 55450, "M.musculus YB-1 mRNA," Apr. 18, 2005, 2 pages.
GenBank® Accession No. X58723 GI: 34522, "Human MDR1 (multidrug resistance) gene for P-glycoprotein," Nov. 14, 2006, 2 pages.
GenBank® Accession No. XM_001002680 GI: 255708374, "Predicted: Mus musculus ATP-binding cassette, sub-family B (MDR/TAP), member 5 (Abcb5), mRNA," Jun. 20, 2007, 2 pages.
GenBank® Accession No. XM_005250045.1 GI: 530387105, "Predicted: *Homo sapiens* v-raf murine sarcoma viral oncogene homolog B (BRAF), transcript variant X1, mRNA," Aug. 13, 2013, 4 pages.
GenBank® Accession No. XM_005250046.1 GI: 530387107, "Predicted: *Homo sapiens* v-raf murine sarcoma viral oncogene homolog B (BRAF), transcript variant X2, mRNA," Aug. 13, 2013, 4 pages.
GenBank® Accession No. XM_005250047.1 GI: 530387109, "Predicted: *Homo sapiens* v-raf murine sarcoma viral oncogene homolog B (BRAF), transcript variant X3, mRNA," 2 pages.
GenBank® Accession No. XM_005251574.1 GI: 530390132, "Predicted: *Homo sapiens* tyrosinase-related protein 1 (TYRP1), transcript variant X1, mRNA," Feb. 3, 2014, 3 pages.
GenBank® Accession No. XM_005270904.1 GI: 530362706, "Predicted: *Homo sapiens* Y box binding protein 1 (YBX1), transcript variant X1, mRNA," Aug. 13, 2013, 2 pages.
"A Randomized Study of Nivolumab Versus Bevacizumab and a Safety Study of Nivolumab in Adult Subjects With Recurrent Glioblastoma (GBM) (CheckMate 143)," Clinical Trials.gov [online] Dec. 2014, [retrieved on Mar. 18, 2015]. Retrieved from the Internet: <URL: https://clinicaltrials.gov/ct2/show/NCT02017717>, 3 pages.
"UniProt entry P08183—MDR1_HUMAN: Multidrug resistance protein 1," Aug. 1, 1988, pp. 1-12. Retrieved from the Internet: <http://www.uniprot.org/uniprot/P08183#pathology_and_biotech> on Jun. 3, 2015.
"UniProt entry P35968—VGFR2_Human: Vascular endothelial growth factor receptor 2," Jun. 1, 1994, pp. 1-8. Retrieved from the Internet: <http://www.uniprot.org/uniprot/P35968> on Jun. 3, 2015.
"Using Viro/Immunotherapy to Target Stem-Like Cells of Tumor Recurrence," Oncolytic Viruses and Stem Cell Workshop, National Cancer Institute (NCI), Washington D.C., Sep. 6, 2013, [slideshow] 51 pages.
Ahmad et al., "Optimised electroporation mediated DNA vaccination for treatment of prostate cancer," *Genetics Vaccines and Therapy*, 8:1, pp. 1-13, Feb. 5, 2010.
Alonso-Camino et al., "The profile of tumor antigens which can be targeted by immunotherapy depends upon the tumor's anatomical site," *Mol. Ther.*, 22(11):1936-1948, Nov. 2014.
Avogadri and Wolchok, "Selecting antigens for cancer vaccines," Nat. Biotechnol. 30(4):328-329, Apr. 10, 2012.
Barry et al., "Expression library immunization to discover and improve vaccine antigens," *Immunol Rev.*, 199:68-83, Jun. 2004.
Baxevanis et al., "Cancer immunotherapy," *Crit Rev Clin Lab Sci.*, 46(4): 167-189, 2009.
Boisgerault et al., "Functional cloning of recurrence-specific antigens identifies molecular targets to treat tumor relapse," Mol. Ther., 21(8):1507-1516, Epub Jun. 11, 2013.

(56) References Cited

OTHER PUBLICATIONS

Bridle et al., "Vesicular stomatitis virus as a novel cancer vaccine vector to prime antitumor immunity amenable to rapid boosting with adenovirus," Mol. Ther., 17(10):1814-1821, Oct. 2009.
Chen et al., "Principal expression of two mRNA isoforms (ABCB 5alpha and ABCB 5beta ) of the ATP-binding cassette transporter gene ABCB 5 in melanoma cells and melanocytes," Pigment Cell Res., 18(2):102-112, Apr. 2005 [author manuscript].
Cho et al., "A potent vaccination strategy that circumvents lymphodepletion for effective antitumor adoptive T-cell therapy," Cancer Res., 72:1986-1995, Apr. 15, 2012.
Chong et al., "Expression of co-stimulatory molecules by tumor cells decreases tumorigenicity but may also reduce systemic antitumor immunity," Hum Gene Ther., 7(14):1771-1779, Sep. 10, 1996.
Cluff, "Monophosphoryl Lipid A (MPL) as an Adjuvant for Anit-Cancer Vaccines: Clinical Results," Lipid A in Cancer Therapy, Landes Bioscience and Springer Science and Business Media, Chpt. 10, pp. 111-123, 2009.
Daniels et al., "A simple method to cure established tumors by inflammatory killing of normal cells," Nature Biol., 22(9):1125-1132, Epub Aug. 2004.
Diaz et al., "Oncolytic immunovirotherapy for melanoma using vesicular stomatitis virus," Cancer Res., 67(6):2840-2848 Mar. 2007.
Ebert et al., "Systemic therapy of experimental breast cancer metastases by mutant vesicular stomatitis virus in immune-competent mice," Cancer Gene Ther., 12(4):350-358, Apr. 2005.
Fernandez et al., "Genetically engineered vesicular stomatitis virus in gene therapy: application for treatment of malignant disease," J. Virol., 76(2):895-904, Jan. 2002.
Ferrone, "Immunotherapy dispenses with tumor antigens," Nature Biotech., 2004, 22(9):1096-1098.
Francisco et al., "Chapter 4: Melanoma Genetics: From Susceptibility to Progression," Melanoma—From Early Detection to Treatment, Dr. Ht Duc (Ed.), pp. 83-136. Retrieved from the Internet: <http://www.intechopen.com/books/melanoma-from-early-detection-to-treatment/melanoma-genetics-from-susceptibility-to-progression> Jan. 2013.
Galivo et al., "Interference of CD40L-mediated tumor immunotherapy by oncolytic vesicular stomatitis virus," Human Gene Ther., 21(4):439-450, Apr. 2010.
Galivo et al., "Single-cycle viral gene expression, rather than progressive replication and oncolysis, is required for VSV therapy of B16 melanoma," Gene Ther., 17(2):158-170, print Feb. 2010, Epub Dec. 2009.
Hall and Brown, "Human N-ras: cDNA cloning and gene structure," Nucleic Acids Res., 13(14):5255-5268, Jul. 1985.
Heim, "Normal high resolution karyotypes in patients with adenomatosis of the colon and rectum," Hereditas., 102(2):171-175, 1985.
Hogquist et al., "T cell receptor antagonist peptides induce positive selection," Cell, 76(1):17-27, Jan. 1994.
Jenks et al., "Safety studies on intrahepatic or intratumoral injection of oncolytic vesicular stomatitis virus expressing interferon-beta in rodents and nonhuman primates," Hum. Gene Ther., 21(4):451-462, Apr. 2010.
Joseph et al., "Association of the autoimmune disease scleroderma with an immunologic response to cancer," Science, 343(6167):152-157, Epub Dec. 5, 2013.
Kaluza et al., "Adoptive transfer of cytotoxic T lymphocytes targeting two different antigens limits antigen loss and tumor escape," Hum Gene Ther., 23(10):1054-1064, Epub Aug. 13, 2012.
Kottke et al, "Broad antigenic coverage induced by vaccination with virus-based cDNA libraries cures established tumors," Nat Med., 17(7):854-859, Jun. 2011.
Kottke et al., "Antitumor immunity can be uncoupled from autoimmunity following heat shock protein 70-mediated inflammatory killing of normal pancreas," Cancer Res., 69(19):7767-1774, Oct. 2009.
Kottke et al., "Induction of hsp70-mediated Th17 autoimmunity can be exploited as immunotherapy for metastatic prostate cancer," Cancer Res., 67(24):11970-11979, Dec. 2007.
Lawson et al., "Recombinant vesicular stomatitis viruses from DNA," PNAS, 92(10):4477-4481, May 9, 1995.
Linardakis et al., "Enhancing the efficacy of a weak allogeneic melanoma vaccine by viral fusogenic membrane glycoprotein-mediated tumor cell-tumor cell fusion," Cancer Res., 62(19): 5495-5504, Oct. 2002.
Obuchi et al., "Development of recombinant vesicular stomatitis viruses that exploit defects in host defense to augment specific oncolytic activity," J. Virol., 77(16):8843-8856, Aug. 2003.
Overwijk et al., "Tumor regression and autoimmunity after reversal of a functionally tolerant state of self-reactive CD8+ T cells," J. Exp. Med., 198(4):569-580, Aug. 2003.
Pulido et al., "Using virally expressed melanoma cDNA libraries to identify tumor-associated antigens that cure melanoma," Nat Biotechnol., 30(4):337-343, Mar. 18, 2012.
Radvanyi, "Immunotherapy Exposes Cancer Stem Cell Resistance and a New Synthetic Lethality," Mol. Ther. 21:1472-1474, Aug. 2013.
Ramsburg et al., "A vesicular stomatitis virus recombinant expressing granulocyte-macrophage colony-stimulating factor induces enhanced T-cell responses and is highly attenuated for replication in animals," J. Virol., 79(24):15043-15053, Dec. 2005.
Roda et al., "Stabilization of HIF-2α induces sVEGFR-1 production from tumor-associated macrophages and decreases tumor growth in a murine melanoma model," J. Immunol., 189(6):3168-3177, Sep. 15, 2012.
Rommelfanger et al., "Systemic combination virotherapy for melanoma with tumor antigen-expressing vesicular stomatitis virus and adoptive T-cell transfer," Cancer Res., 72(18):4753-4764, Sep. 15, 2012.
Sausville and Burger, "Contributions of human tumor xenografts to anticancer drug development," Cancer Res, 66(7): 3351-3354, Apr. 2006.
Shakhova et al., "Sox10 promotes the formation and maintenance of giant congenital naevi and melanoma," Nat. Cell Biol., 14(8):882-890, Aug. 2012.
Shibata et al., "Downstream region of the human tyrosinase-related protein gene enhances its promoter activity," Biochem. Biophys. Res. Commun., 184(2):568-575, Apr. 1992.
Srivastava, "Immunotherapy of human cancer: lessons from mice," Nat Immunol., 1(5):363-366, Nov. 2000.
Suzuki et al., "Structural organization of the human mitochondrial cytochrome c1 gene," J. Biol. Chem., 264(3):1368-1374, Jan. 1989.
Thomas and Massagué, "TGF-beta directly targets cytotoxic T cell functions during tumor evasion of immune surveillance.," Cancer Cell, 8(5):369-380, Nov. 2005.
Van Belle et al., "Melanoma-associated expression of transforming growth factor-beta isoforms," Am J Pathol., 148(6):1887-1894, Jun. 1996.
Vinals et al., "Using in silico transcriptomics to search for tumor-associated antigens for immunotherapy," Vaccine, 19(17-19):2607-2614, Mar. 21, 2001.
Wagner et al., "Targeted nucleic acid delivery into tumors: new avenues for cancer therapy," Biomed Pharmacother., 58(3):152-161, Apr. 2004.
Willmon et al., "Vesicular stomatitis virus-induced immune suppressor cells generate antagonism between intratumoral oncolytic virus and cyclophosphamide," Mol. Ther., 19(1):140-149, Jan. 2010.
Wongthida et al., "VSV oncolytic virotherapy in the B16 model depends upon intact MyD88 signaling," Mol. Ther., 19(1):150-158, Jan. 2011.
Yoshida et al., "Development of gene therapy to target pancreatic cancer," Cancer Sci., 95(4): 283-289, Apr. 2002.
Zhuang et al., "C-MYC overexpression is required for continuous suppression of oncogene-induced senescence in melanoma cells," Oncogene, 27(52):6623-6634, Nov. 6, 2008.
European Search Report for Application No. 11742816.9 dated Jul. 10, 2013, 8 pages.

(56) References Cited

OTHER PUBLICATIONS

European Search Report for Application No. 13760532.5, dated Oct. 20, 2015, 14 pages.
Office Action for European Application No. 11742816.9, dated Apr. 14, 2016, 5 pages.
Office Action for U.S. Appl. No. 13/578,224 dated May 8, 2013, 14 pages.
Office Action for U.S. Appl. No. 13/578,224 dated Dec. 27, 2013, 17 pages.
Office Action for U.S. Appl. No. 13/578,224 dated Dec. 4, 2014, 14 pages.
Office Action for U.S. Appl. No. 13/578,224 dated Jun. 5, 2015, 14 pages.
Office Action for U.S. Appl. No. 13/578,224 dated Sep. 24, 2015, 16 pages.
Office Action for U.S. Appl. No. 14/385,240, dated Mar. 18, 2016, 14 pages.
Office Action for U.S. Appl. No. 13/578,224, dated Jun. 3, 2016, 14 pages.
International Search Report and Written Opinion in Application No. PCT/US2011/024397, dated Oct. 25, 2011, 10 pages.
International Preliminary Report on Patentability in Application No. PCT/US2011/024397, dated Aug. 23, 2012, 6 pages.
International Search Report and Written Opinion for Application No. PCT/US2013/031953, dated Jul. 4, 2013, 8 pages.
International Preliminary Report on Patentability for PCT/US2013/031953 dated Sep. 25, 2014, 6 pages.
International Search Report and Written Opinion in Application No. PCT/US2015/021574, dated Jul. 8, 2015, 23 pages.
International Search Report and Written Opinion in Application No. PCT/US2015/021576, dated Jul. 10, 2015, 13 pages.
International Preliminary Report on Patentability for PCT/US2015/021574, dated Sep. 29, 2016, 14 pages.
International Preliminary Report on Patentability for PCT/US2015/021576, dated Sep. 29, 2016, 10 pages.
Extended European Search Report in International Application No. EP15765220.7, dated Jan. 29, 2018, 22 pages.

\* cited by examiner

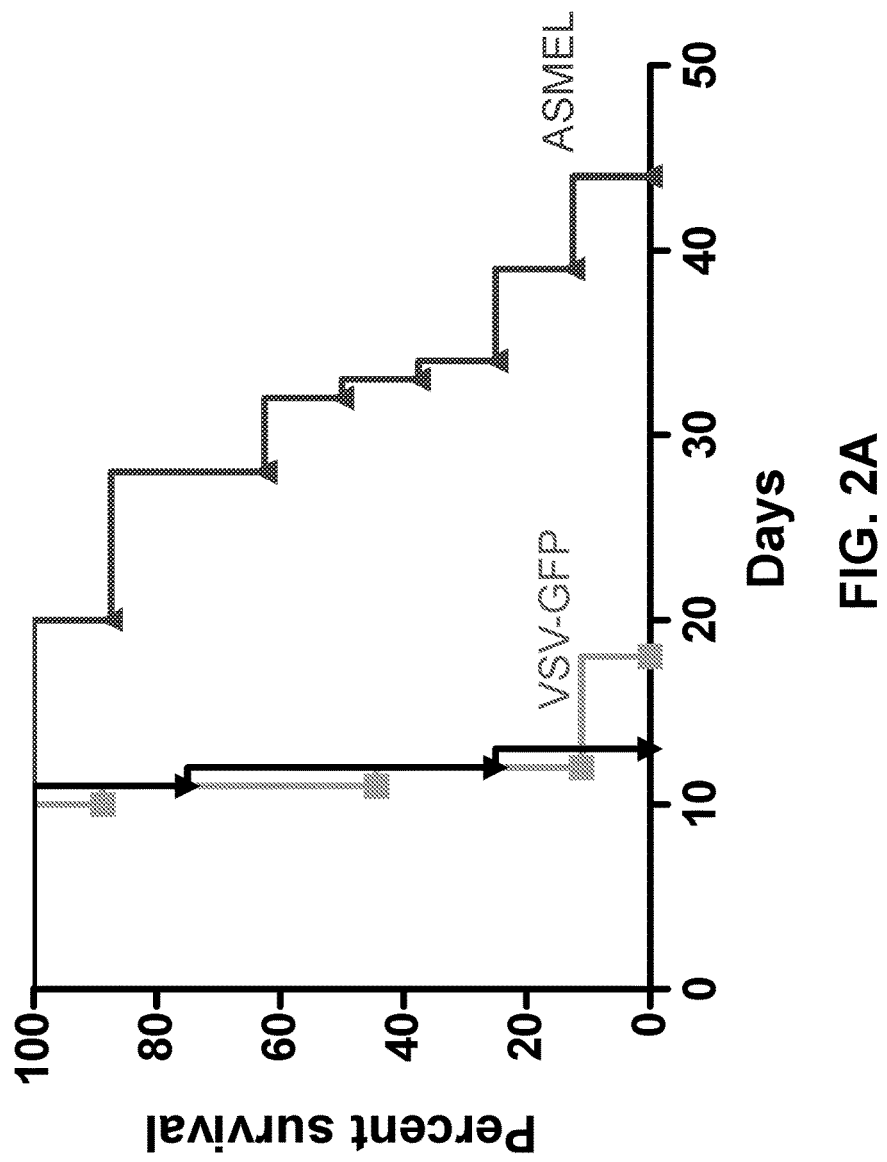

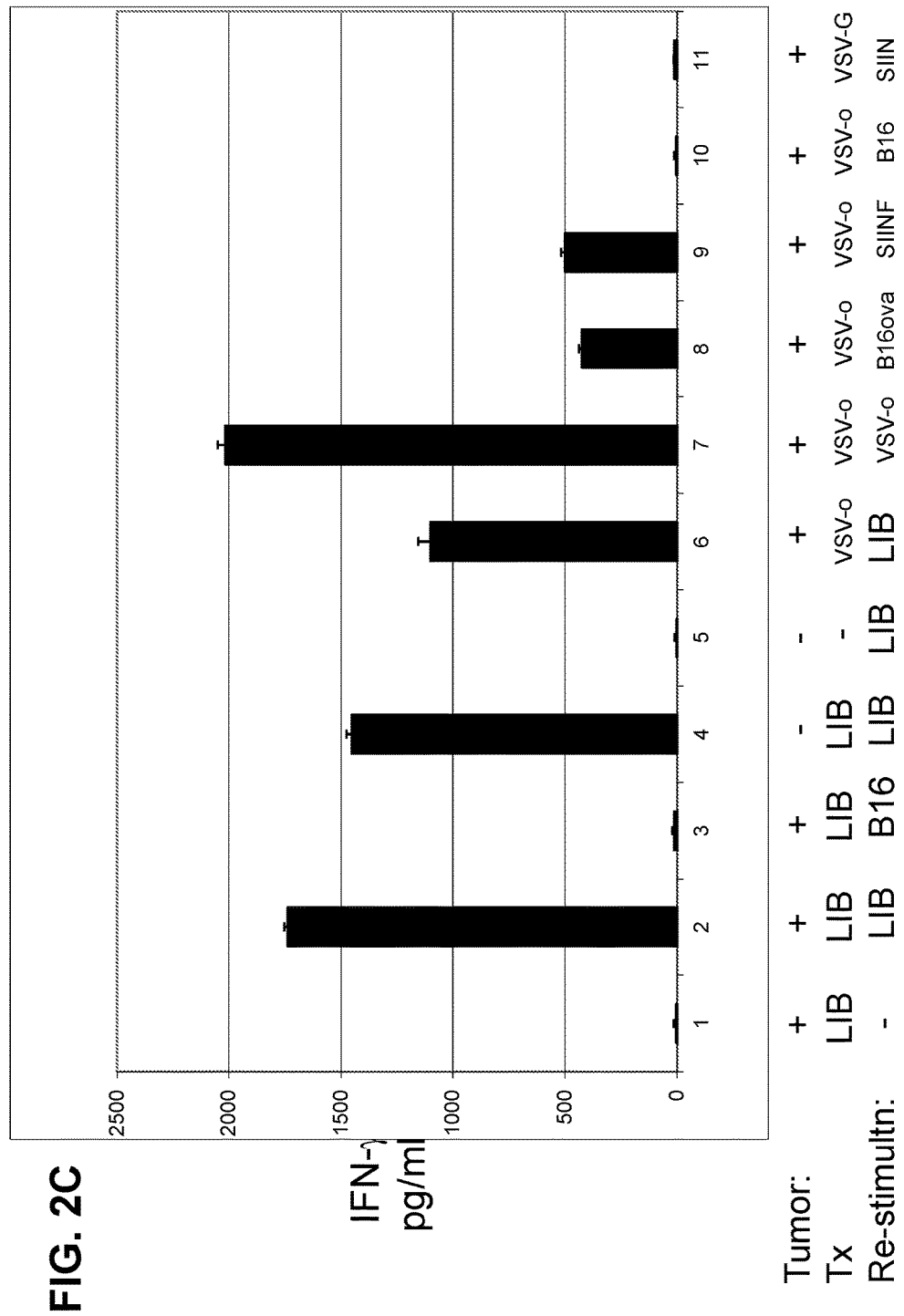

FIG. 6B (i.c. tumors)

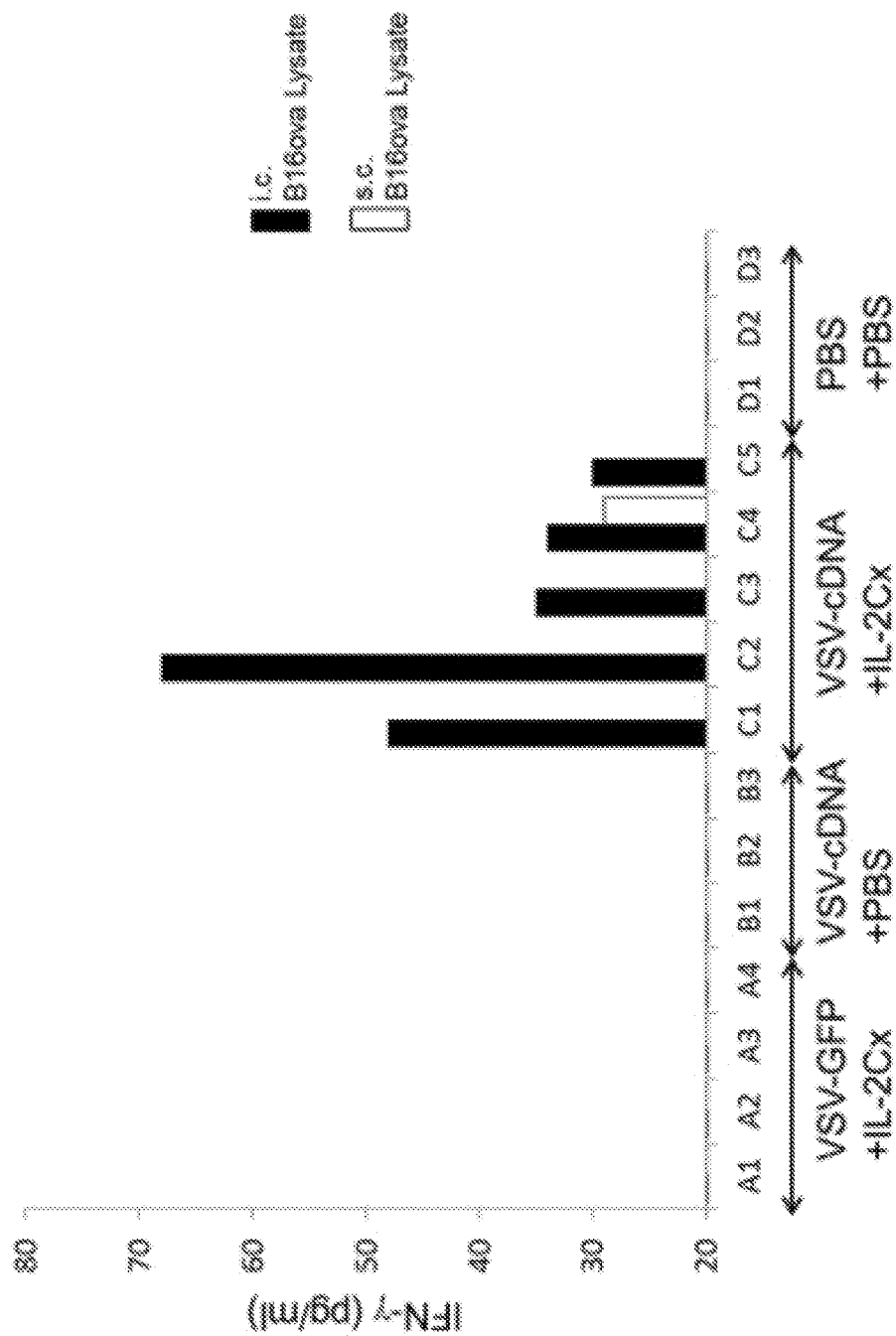

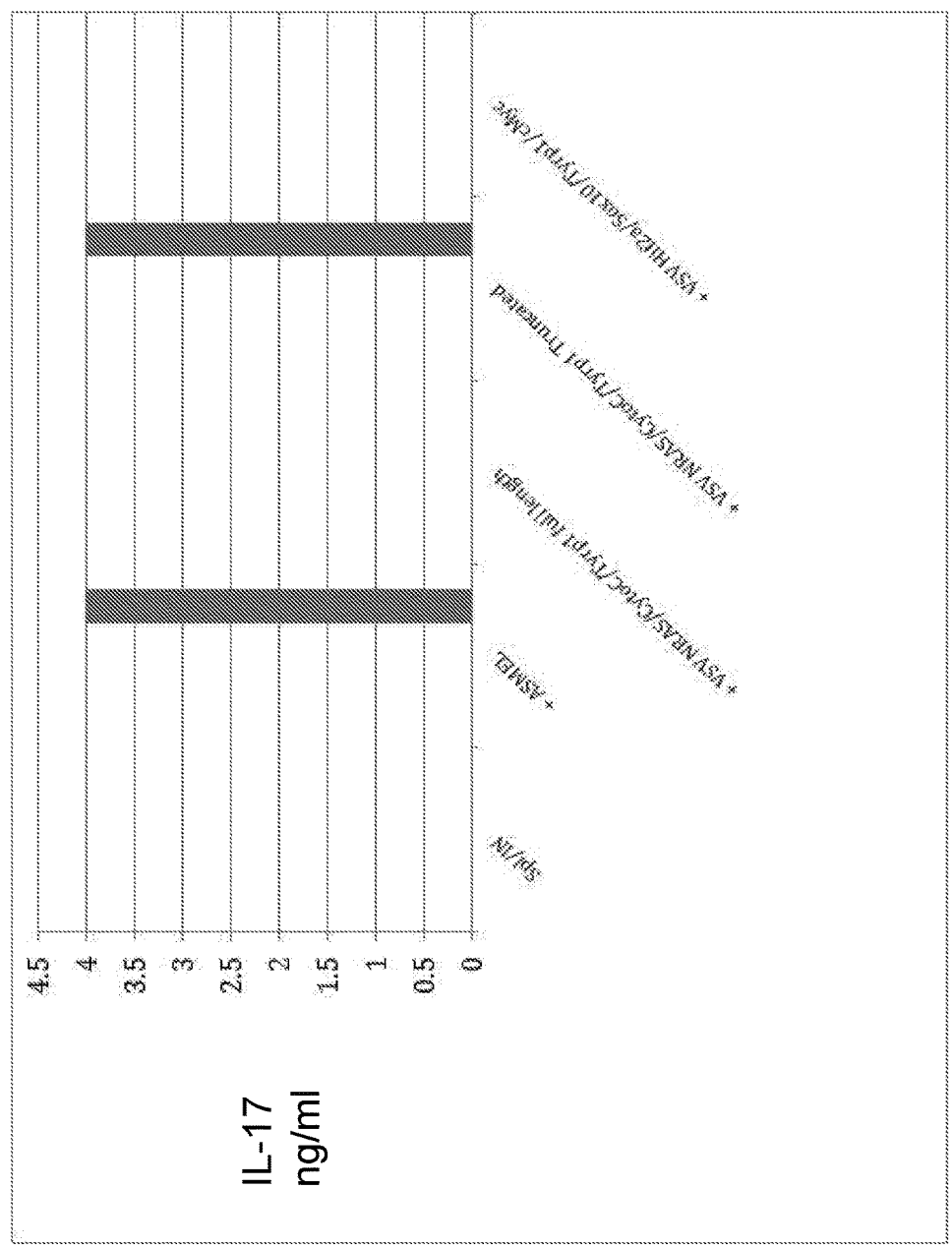

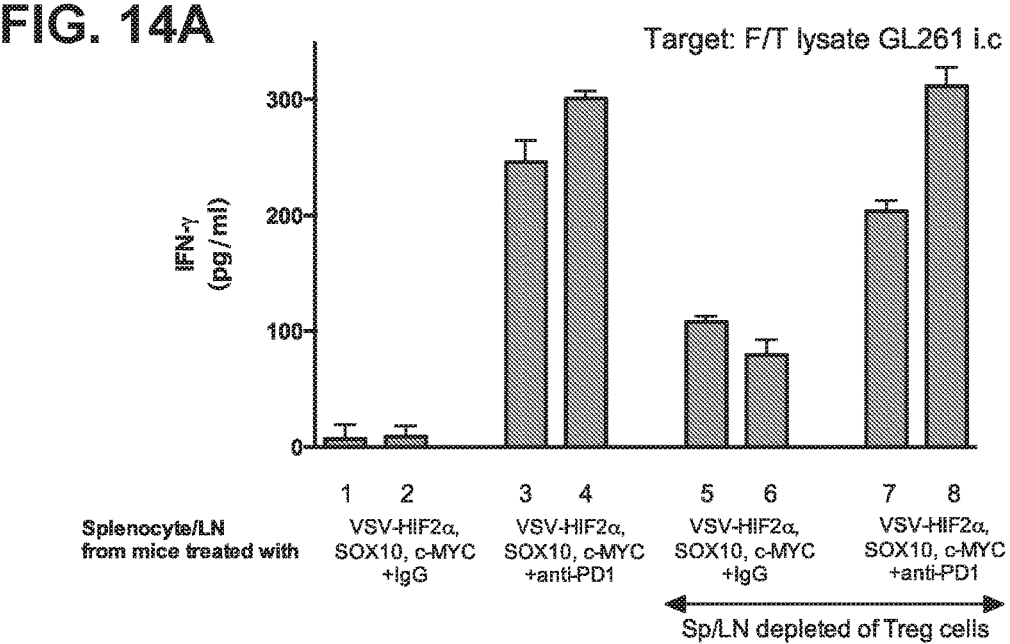
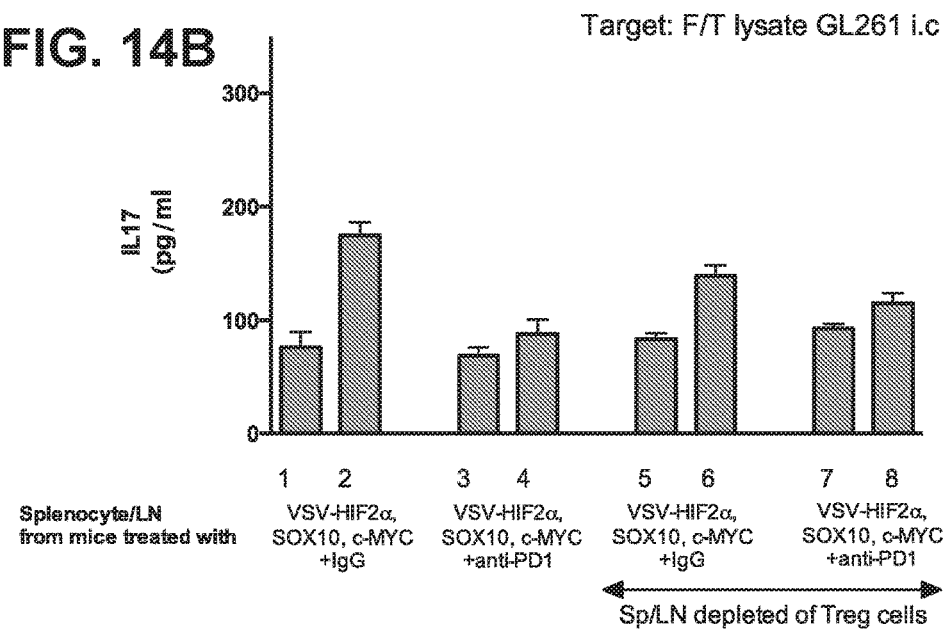

VSV-CYT-C Virus Recovered from the ASMEL Is Truncated at the 3' End in the CYT-C Sequences 3'—CYT-C cDNA ACCATCGAAAACGCATGGGGCTCAAGATGTTGATGATGATGGCTCTGCTGGT
GCCCCTGGTC-                INTERGENIC VSV SEQUENCE
Nhe1

TG|A- GCTAGCCAGATTCTTCATGTTTGGACCAAATCAACTTGTGATACCATGCTCAAGA-
   Y-STOP
DEL

Intergenic
                              Dinucleotide          L Gene

GGCCTCAATTATATTTGAGTTTTTAATTTTTATGAAAAAACTAACAGC
AATCATG

INTERGENIC VSV       INTERGENIC VSV
                    Poly A               Transcription
                    SEQUENCE             START
                                         SEQUENCE DEL = DELETED:
3'coding end of cDNA:
(c)YTIKRHKWSVLKSRKLAYRPPK;
(SEQ ID NO:13)
3'untranslated region;
Cellular poly A;
3' primer from pSPORT used to
amplify cDNA and linked to Nhe1 site.

FIG. 17

VSV-TYRP-1 Virus Recovered from the ASMEL Is Truncated at the 3' End in the TYRP-1 Sequences

3'–

VSV-mIFNbeta-mTYRP-1

N — P — M — mIFN-beta — G — mTYRP-1 — L

VSV-mIFN-beta

N — P — M — mIFN-beta — G — L

VSV-mTYRP-1

N — P — M — G — mTYRP-1 — L

METHODS AND MATERIALS FOR TREATING CANCER

CROSS REFERENCE TO RELATED APPLICATIONS

This application is a National Stage application under 35 U.S.C. § 371 of International Application No. PCT/US2015/021576, having an International Filing Date of Mar. 19, 2015, which claims the benefit of U.S. Provisional Ser. No. 61/955,677 filed Mar. 19, 2014. This disclosure of the prior application is considered part of (and is incorporated by reference in) the disclosure of this application.

STATEMENT AS TO FEDERALLY SPONSORED RESEARCH

This invention was made with government support under CA107082, CA130878, and CA132734, awarded by the National Institutes of Health. The government has certain rights in the invention.

BACKGROUND

1. Technical Field

This document relates to methods and materials for treating cancer. For example, this document relates to methods and materials for identifying antigens and combinations of antigens that can be used to treat cancer. This document also relates to methods and materials for using combinations of antigens to treat cancer (e.g., melanoma, subcutaneous cancers, gliomas, and intracranial cancers).

2. Background Information

Cancer is a serious illness that affects many people every year. In general, there are several common methods for treating cancer: surgery, chemotherapy, radiation therapy, immunotherapy, and biologic therapy. When initially diagnosed with cancer, a cancer specialist such as an oncologist can provide a patient with various cancer treatment options. Typically, an oncologist will recommend the best treatment plan based on the type of cancer, how far it has spread, and other important factors like the age and general health of the patient.

SUMMARY

This document provides methods and materials for treating cancer. For example, this document provides combinations of antigens having the ability to reduce the presence of cancer (e.g., reduce established tumors) within a mammal (e.g., a human). As described herein, combinations of antigens (e.g., a combination of an N-RAS antigen, a TYRP1 antigen, and a CYT-C antigen) can be used to treat cancer (e.g., melanoma or a subcutaneous cancer). For example, VSV vectors designed to express an N-RAS antigen, a TYRP1 antigen, and a CYT-C antigen can be used to treat established tumors (e.g., melanomas or subcutaneous cancers). As also described herein, combinations of antigens (e.g., a combination of an HIF-2α antigen, a SOX-10 antigen, a C-MYC antigen, and a TYRP-1 antigen) can be used to treat cancer (e.g., intracranial cancers or gliomas). For example, VSV vectors designed to express an HIF-2α antigen, a SOX-10 antigen, a C-MYC antigen, and a TYRP-1 antigen can be used to treat established tumors (e.g., intracranial cancers or gliomas).

In general, one aspect of this document features a composition comprising, or consisting essentially of, nucleic acid encoding HIF-2α, SOX-10, C-MYC, and TYRP-1, wherein the composition comprises less than 100 separate nucleic acid molecules. The composition can comprise a nucleic acid molecule encoding the HIF-2α, a nucleic acid molecule encoding the SOX-10, a nucleic acid molecule encoding the C-MYC, and a nucleic acid molecule encoding the TYRP-1. The composition can comprise less than 50 separate nucleic acid molecules. The composition can comprise less than 10 separate nucleic acid molecules.

In another aspect, this document features a composition comprising, or consisting essentially of, nucleic acid encoding an HIF-2α antigen, a SOX-10 antigen, a C-MYC antigen, and a TYRP-1 antigen, wherein the composition comprises less than 100 separate nucleic acid molecules. The composition can comprise a nucleic acid molecule encoding the HIF-2α antigen, a nucleic acid molecule encoding the SOX-10 antigen, a nucleic acid molecule encoding the C-MYC antigen, and a nucleic acid molecule encoding the TYRP-1 antigen. The composition can comprise less than 50 separate nucleic acid molecules. The composition can comprise less than 10 separate nucleic acid molecules.

In another aspect, this document features a method of treating an intracranial cancer within a mammal. The method comprises, or consists essentially of, administering to the mammal a composition comprising, or consisting essentially of, nucleic acid encoding an HIF-2α antigen, a SOX-10 antigen, a C-MYC antigen, and a TYRP-1 antigen, wherein the composition comprises less than 100 separate nucleic acid molecules. The intracranial cancer can be a glioma. The HIF-2α antigen, the SOX-10 antigen, the C-MYC antigen, and the TYRP-1 antigen can be VSV-expressed.

In another aspect, this document features a composition comprising, or consisting essentially of, nucleic acid encoding an HIF-2α antigen, a SOX-10 antigen, and a C-MYC antigen, wherein the composition comprises less than 100 separate nucleic acid molecules. The composition can comprise a nucleic acid molecule encoding the HIF-2α antigen, a nucleic acid molecule encoding the SOX-10 antigen, and a nucleic acid molecule encoding the C-MYC antigen. The composition can comprise less than 50 separate nucleic acid molecules. The composition can comprise less than 10 separate nucleic acid molecules.

In another aspect, this document features a method of treating cancer within a mammal. The method comprises, consists essentially of, administering to the mammal a composition comprising nucleic acid encoding an HIF-2α antigen, a SOX-10 antigen, and a C-MYC antigen, wherein the composition comprises less than 100 separate nucleic acid molecules. The cancer can be a melanoma. The HIF-2α antigen, the SOX-10 antigen, and the C-MYC antigen can be VSV-expressed.

In another aspect, this document features a composition of any one of above paragraphs, wherein the composition comprises an immune checkpoint inhibitor. The immune checkpoint inhibitor can be an anti-PD-1 antibody or an anti-CTLA4 antibody.

In another aspect, this document features a method of any one of the above paragraphs, wherein the method comprises administering an immune checkpoint inhibitor to the mammal. The immune checkpoint inhibitor can be an anti-PD-1 antibody or an anti-CTLA4 antibody.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A. C57BL/6 mice bearing 5 day established intra-cranial B16ova tumors were treated intravenously with PBS or $5 \times 10^6$ pfu of VSV-GFP or VSV-ova on days 6, 8, and 10. Survival time is shown in days. FIG. 1B. C57BL/6 mice bearing 5 day established i.c. tumors (7-8/group) were treated with naïve Pmel T cells ($1 \times 10^6$ cells/100 µL) or PBS (100 µL) on day 6. Three doses of VSV-hgp100 or VSV-ova ($2.5 \times 10^6$ pfu/100 µL) or PBS (100 µL) were given intravenously every other day starting one day after adoptive T cell transfer.

FIGS. 2A-D. Systemic treatment with the ASMEL. FIG. 2A. C57BL/6 mice bearing 5 day established intra-cranial B16ova tumors were treated intravenously with $10^7$ pfu of VSV-GFP or the ASMEL on days 6, 8, 10, 13, 15, 17, 20, 22, 24, 27, 19, and 31. Survival time is shown in days. FIGS. 2B and 2C. Pooled splenocytes and lymph node cells ($10^6$/well) from mice that had either never had a tumor (Tumor; –) or which had been treated (Tx) for established tumors (Tumor; +) with either the ASMEL (nine i.v. injections) (LIB), PBS (–), VSV-ova (VSV-o), or VSV-GFP (VSV-G) were re-stimulated (Re-stimultn) in vitro with nothing (–), about $10^4$ pfu of the parental ASMEL virus stock (LIB), freeze/thaw lysate of B16 cells (B16), about $10^4$ pfu of VSV-ova (VSV-o), freeze thaw lysate of B16ova cells (B16ova), or with the ova-specific SIINFEKL peptide (SIIN). 24 hours later, the cultures were replenished with an additional $10^6$ LN/splenocytes with a further round of virus infection/re-stimulation 24 after that. 48 hours following the final infection with virus, supernatants were assayed for IL-17 (B) or IFN-γ (C) by ELISA. FIG. 2D. LN/splenocyte cultures ($10^4$/well) from C57BL/6 mice bearing i.c. B16 tumors and treated with the ASMEL were screened for secretion of IL-17 induced by infection with aliquots of about $10^4$ pfu of the parental ASMEL virus stock in the presence of recombinant hsp70 (10 µg/mL). Aliquots that contained virus competent for inducing the IL-17 recall response were pooled and expanded in BHK cells (24-36 hours). New LN/splenocyte cultures from ASMEL-treated mice were infected with serial dilutions of this expanded stock in the presence of recombinant hsp70, and assayed for IL-17 production. The highest dilution of the virus stock (about $10^1$ pfu), which induced IL-17 at levels significantly above background (>100 pg/mL), was amplified by passaging through BHK cells for 24-36 hours. Serial dilutions of this expanded stock were screened for their ability to induce IL-17. 10 µL aliquots of the highest dilution of the virus, which induced IL-17 ('$10^2$ pfu') were used as the starting point for limiting dilution cloning on BHK cells to identify the dilution at which a single virus particle generated cytopathic effect (+). Of 18 individual viruses screened from this experiment, five viruses encoded part of the human HIF-2α gene (Genbank® Accession No. NM_001430 (GI No. 262527236), five viruses encoded part of the human SOX-10 gene (Genbank® Accession No. BT020029 (GI No. 54696919), three viruses encoded part of the human TYRP1 gene (Genbank® Accession Nos. NM_000550 (GI No. 169881242) and NW_004078038.1), and four viruses encoded sequence of the human C-MYC gene (Genbank® Accession No. V00568 (GI No. 34815)).

FIG. 3A. LN/splenocyte cultures from mice treated for i.c. B16ova tumors with the ASMEL mice were screened for IL-17 secretion following re-stimulation in vitro with a total of $10^7$ pfu of combinations of the viruses selected from the screen of FIG. 3D, including VSV-HIF-2α+VSV-SOX-10+VSV-GFP (Lane 1); VSV-C-MYC+VSV-TYRP-1+VSV-GFP (Lane 2); VSV-C-MYC+VSV-TYRP-1+VSV-HIF-2α+VSV-SOX-10 (Lane 3); the melanoma derived ASMEL (Lane 4), or the control ASEL VSV-cDNA library from human prostate cDNA (Lane 5). In addition, re-stimulation also was performed with freeze-thaw lysates from long term in vitro cultured B16ova cells (Lane 6); B16ova cells freshly resected from s.c. tumors (Lane 7); B16ova cells freshly resected from three pooled i.c. tumors (Lane 8), or from long term in vitro cultured TC2 murine prostate cells (Lane 9). FIG. 3B. LN/splenocyte cultures from mice treated for s.c. B16ova tumors with the ASMEL were screened for IL-17 secretion following re-stimulation in vitro with $10^7$ pfu of the melanoma derived ASMEL (Lane 1) or the control ASEL VSV-cDNA library from human prostate cDNA (Lane 2); or with freeze-thaw lysates from long term in vitro cultured B16ova cells (Lane 3); B16ova cells freshly resected from s.c. tumors (Lane 4); or B16ova cells freshly resected from three pooled i.c. tumors (Lane 5). FIG. 3C. LN/splenocyte cultures from mice treated for either i.c. (Lanes 1-12) or s.c. (Lanes 13-24) B16ova tumors with the ASMEL were screened for IL-17 secretion following re-stimulation in vitro with $10^7$ pfu of the melanoma derived ASMEL (Lanes 1 and 13); PBS (Lanes 2 and 14); VSV-GFP (Lanes 3 and 15); or with a total of $10^7$ pfu of combinations of viruses VSV-CYT-C+VSV-N-RAS+VSV-TYRP-1 (Lanes 4 and 16); VSV-HIF-2α+VSV-SOX-10+VSV-C-MYC (Lanes 5 and 17); VSV-C-MYC+VSV-TYRP-1+VSV-HIF-2α+VSV-SOX-10 (Lanes 6 and 18); VSV-CYT-C+VSV-N-RAS (Lanes 7 and 19); VSV-CYT-C+VSV-TYRP-1 (Lanes 8 and 20); VSV-TYRP-1+VSV-N-RAS (Lanes 9 and 21); VSV-HIF-2α+VSV-SOX-10 (Lanes 10 and 22); VSV-C-MYC+VSV-SOX-10 (Lanes 11 and 23); or VSV-HIF-2α+VSV-C-MYC (Lanes 12 and 24).

FIG. 4A. cDNA prepared from B16ova cells freshly resected from s.c. tumors (Lanes 1-5), B16ova cells freshly resected from three pooled i.c. tumors (Lanes 6-10), B16ova cells resected from three pooled i.c. tumors and maintained in culture for three weeks (Lanes 11-15), or long term in vitro cultured B16ova cells (Lanes 16-20) were screened by qrtPCR for expression of HIF-2α (Lanes 1, 6, 11, and 16), C-MYC (Lanes 2, 7, 12, and 17), TYRP-1 (Lanes 3, 8, 13, and 18), N-RAS (Lanes 4, 9, 14, and 19), and CYT-C (Lanes 5, 10, 15, and 20). The difference in cycle threshold for expression of the control GAPDH gene and the target gene (CT(GAPDH)-CT(Target gene)) is shown. Results are representative of at least two different tumor samples per treatment. FIG. 4B. HIF-2α polypeptide expression from B16ova cells freshly resected from s.c. tumors (Lane 1), B16ova cells freshly resected from three pooled i.c. tumors (Lane 2), B16ova cells resected from three pooled i.c. tumors and maintained in culture for three weeks (Lane 3), or long term in vitro cultured B16ova cells (Lane 4) was measured by ELISA with samples standardized for equal protein loading. FIG. 4C. The experiment of FIG. 4B was repeated using glioma GL261 cells freshly resected from i.c. tumors (Lane 1) or long term in vitro cultured GL261 cells (Lane 2); prostate TC2 cells freshly resected from s.c. tumors (Lane 3), or long term in vitro cultured TC2 cells (Lane 4).

FIGS. 6A-B. Differential immunotherapy for s.c. and i.c. tumors. C57BL/6 mice bearing 5 day established subcutaneous (FIG. 6A) or intra-cranial (FIG. 6B) B16ova tumors were treated intravenously with a total of $10^7$ pfu of the ASMEL; VSV-N-RAS+VSV-TYRP-1+VSV-CYT-C; (VSV-HIF2α+VSV-SOX-10+VSV-C-MYC+VSV-TYRP-1; or VSV-GFP on days 6, 8, 10, 13, 15, 17, 20, 22, 24, 27, 29, and 31. Survival time is shown in days.

FIGS. 7A-F. T cell co-stimulation enhances VSV-cDNA therapy of i.c. tumors. FIG. 7A. C57BL/6 mice bearing 5 day established intra-cranial B16ova tumors were treated intravenously with PBS+PBS, or with a total of $10^7$ pfu of VSV-HIF2α+VSV-SOX-10+VSV-C-MYC+VSV-TYRP-1+ PBS; or with VSV-HIF2α+VSV-SOX-10+VSV-CMYC+ VSV-TYRP-1+IL-2Cx; or with $10^7$ pfu of VSV-GFP+IL-2Cx, with virus on days 6, 8, 10, 13, 15, and 17 and with IL-2Cx on days 13, 15, and 17. Survival time is shown in days. FIGS. 7B-D. Pooled splenocytes and lymph node cells ($10^6$/well) from mice bearing i.c. B16ova tumors treated with VSV-GFP+IL-2Cx (A1-A4); VSV-HIF2α+VSV-SOX-10+VSV-C-MYC+VSV-TYRP-1+PBS (B1-B3); VSV-HIF2α+VSV-SOX-10+VSV-CMYC+VSV-TYRP-1+IL-2Cx (C1-05); or PBS/PBS (D1-D3) were re-stimulated in vitro with (FIG. 7B) freeze/thaw lysates of TC2 cells (open bars), or TC2 cells pre-infected for 24 hours with VSV-GFP (moi 0.1) (filled bars); (FIG. 7C) freeze/thaw lysates of B16ova cells freshly resected from s.c. (black bars) or i.c. (grey bars) tumors; or (FIG. 7D) with freeze/thaw lysates of GL261 cells freshly resected from i.c. tumors (black bars) or cultured long term in vitro (grey bars) 24 hours later. The cultures were replenished with an additional $10^6$ LN/splenocytes with a further round of re-stimulation 24 after that. 48 hours following the final re-stimulation, supernatants were assayed for IFN-γ by ELISA. FIGS. 7E and 7F. The same supernatants from FIGS. 7B-D also were assayed for IL-17 secretion following re-stimulation as shown.

FIG. 8. Pooled splenocyte/LN cells ($10^5$/well) from mice with B16 tumors that were treated with nine intravenous injections of the ASMEL were infected and re-stimulated 24 hours later in vitro with ASMEL or full length VSV combinations, or truncated cDNA combinations at an MOI of 10. Supernatants were assayed for IL-17 by ELISA 48 hours later.

Figure 1A:
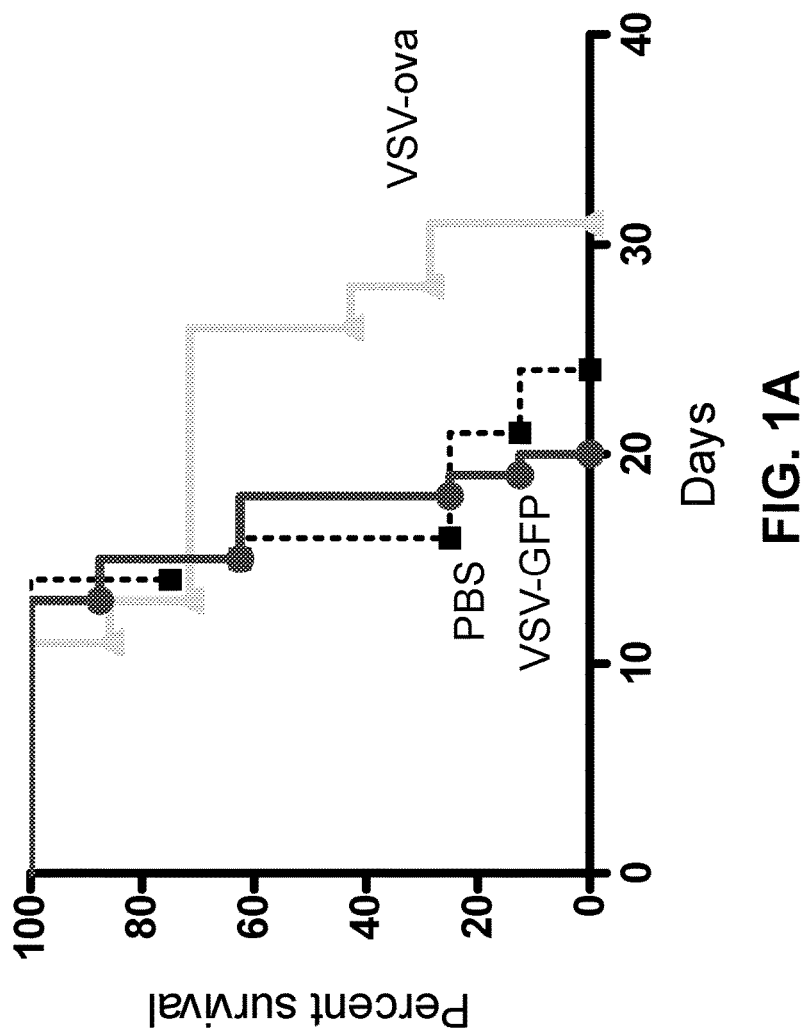
FIGS. 1A-B. Systemic VSV expressing a tumor antigen to treat brain tumors.

IgG), or (VSV-HIF-2α, VSV-SOX-10, and VSV-c-MYC+ anti-PD1 antibody). Cells were plated at 1×10⁶ cells per well and re-stimulated in vitro 3 times at 24 hour intervals with 1×10⁵ cells of freeze thaw lysates of GL261 tumors recovered from mice bearing i.c. GL261 tumors (B and D) or with freeze thaw lysates of in vitro cultured GL261 (C and E). 48 hours later, supernatants were assayed for IFN-γ (B and C) or IL-17 (D and E) by ELISA. F. Splenocytes and lymph nodes also were re-stimulated with the VSV-N protein derived epitope at 5 μg/mL, 3 times for 24 hours. 48 hours later, supernatants were assayed for IFN-γ. Each result is representative of 3 separate measurements. Error bars are expressed as standard deviation (SD).

FIG. 14. Anti-PD1 checkpoint inhibition uncovers a Th1 IFN-γ anti-tumor response. A. Splenocytes and lymph nodes were pooled from 3 C57BL/6 mice per group bearing 5 day established i.c. GL261 tumors treated with either (VSV-HIF-2α, VSV-SOX-10, and VSV-c-MYC+IgG) or (VSV-HIF-2α, VSV-SOX-10, and VSV-c-MYC+anti-PD1 antibody). Cells were plated at 1×10⁶ cells per well and re-stimulated in vitro 3 times at 24 hour intervals with 1×10⁵ cells of freeze thaw lysates of GL261 tumors recovered from mice bearing i.c. GL261 tumors (lanes 1 and 2, and 3 and 4). The same experiment also was carried out with splenocytes and lymph node cells depleted of Treg cells (lanes 5 and 6, and 7 and 8). Following 48 hours of culture, supernatants were assayed for IFN-γ (A) or IL-17 (B) by ELISA. Results are representative of 3 separate measurements. Error bars are expressed as standard deviation (SD).

FIG. 15. Double checkpoint inhibition therapy enhances treatment with VSV-antigens. A. C57BL/6 mice bearing 5 day established i.c. GL261 tumors were treated intravenously with a total dose of 5×10⁶ pfu of (VSV-GFP); (VSV-HIF-2α, VSV-SOX-10, and VSV-c-MYC) or PBS on days 6, 8, 10, 13, 15, and 17. On days 13, 15, and 17, these groups also were treated with either anti-PD1 antibody, anti-CTLA4 antibody, anti-PD1 antibody plus anti-CTLA4 antibody, or PBS as shown. Survival with time is shown. B-D. Splenocytes and lymph nodes were pooled from 3 C57BL/6 mice per group bearing 5 day established i.c. GL261 tumors treated with either (VSV-GFP+anti-PD1+ anti-CTLA4); (VSV-HIF-2α, VSV-SOX-10, and VSV-c-MYC+anti-PD1 antibody+anti-CTLA4 antibody); (VSV-HIF-2α, VSV-SOX-10, and VSV-c-MYC+PBS); (PBS+ PBS); (VSV-HIF-2α, VSV-SOX-10, and VSV-c-MYC+anti-PD1 antibody); or (VSV-HIF-2α, VSV-SOX-10, and VSV-c-MYC+anti-CTLA4 antibody). Cells were plated at 1×10⁶ cells per well and re-stimulated in vitro 3 times at 24 hour intervals with 1×10⁵ cells of freeze thaw lysates of GL261 tumors recovered from mice bearing i.c. GL261 tumors (B and D) or with freeze thaw lysates of in vitro cultured GL261 (C and E). 48 hours later, supernatants were assayed for IFN-γ (B and C) or IL-17 (D and E) by ELISA.

Figure 16:
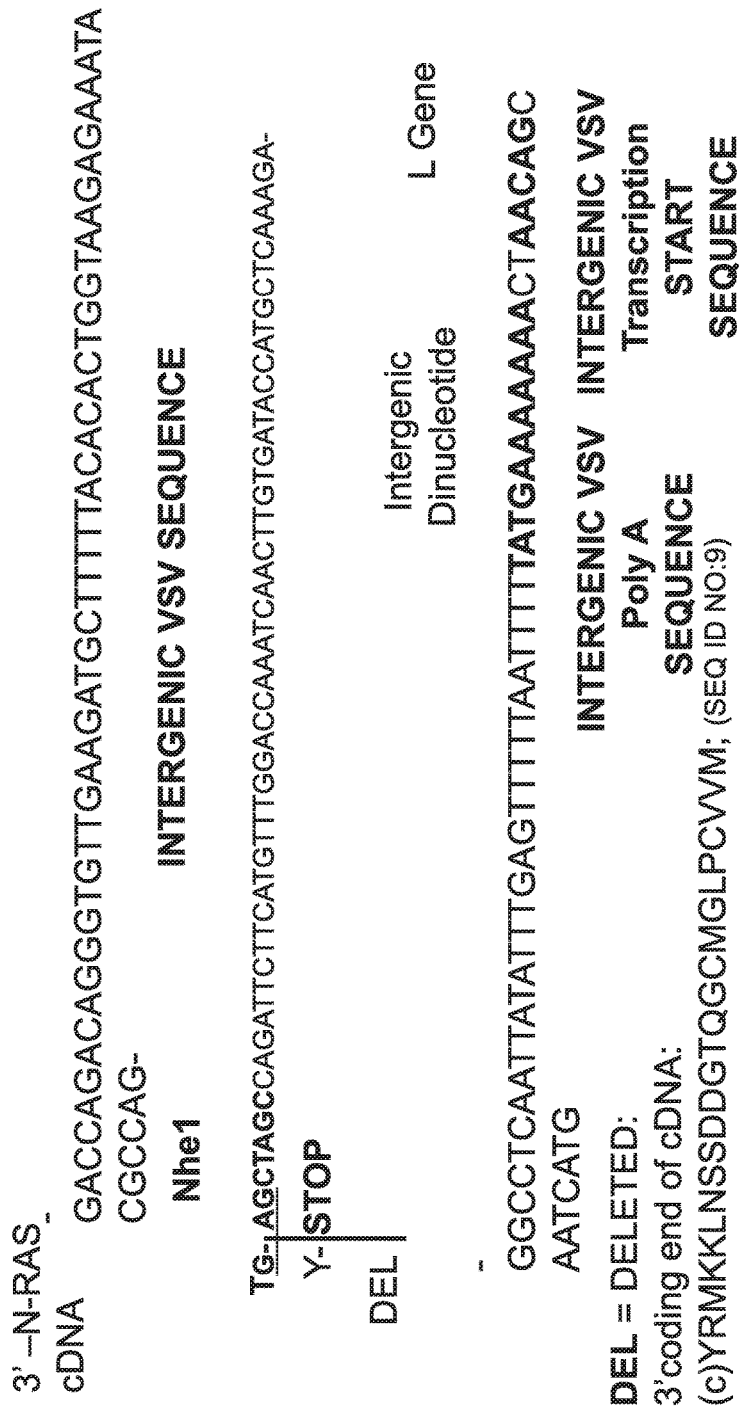

FIG. 16 is contains sequence information for a truncated VSV-N-RAS virus recovered from an ASMEL.

FIG. 17 is contains sequence information for a truncated VSV-CYT-C virus recovered from an ASMEL.

FIG. 18 is contains sequence information for a truncated VSV-TYRP-1 virus recovered from an ASMEL.

Figure 19:
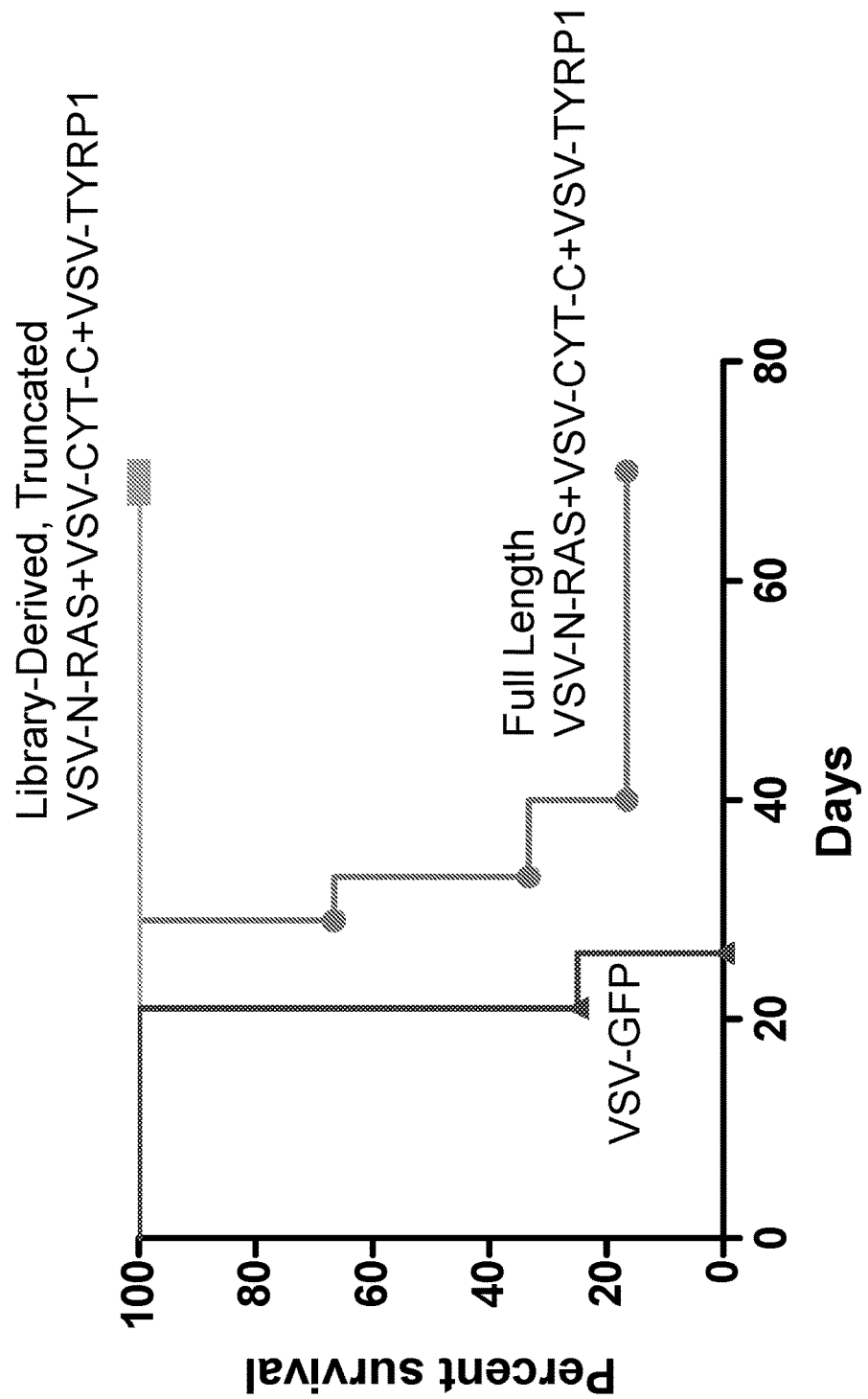

FIG. 19 is a graph plotting the percent survival of mice having s.c. B16 tumors and treated with the indicated VSV vectors.

FIG. 20 is a schematic of the indicated VSV vectors.

Figure 21:
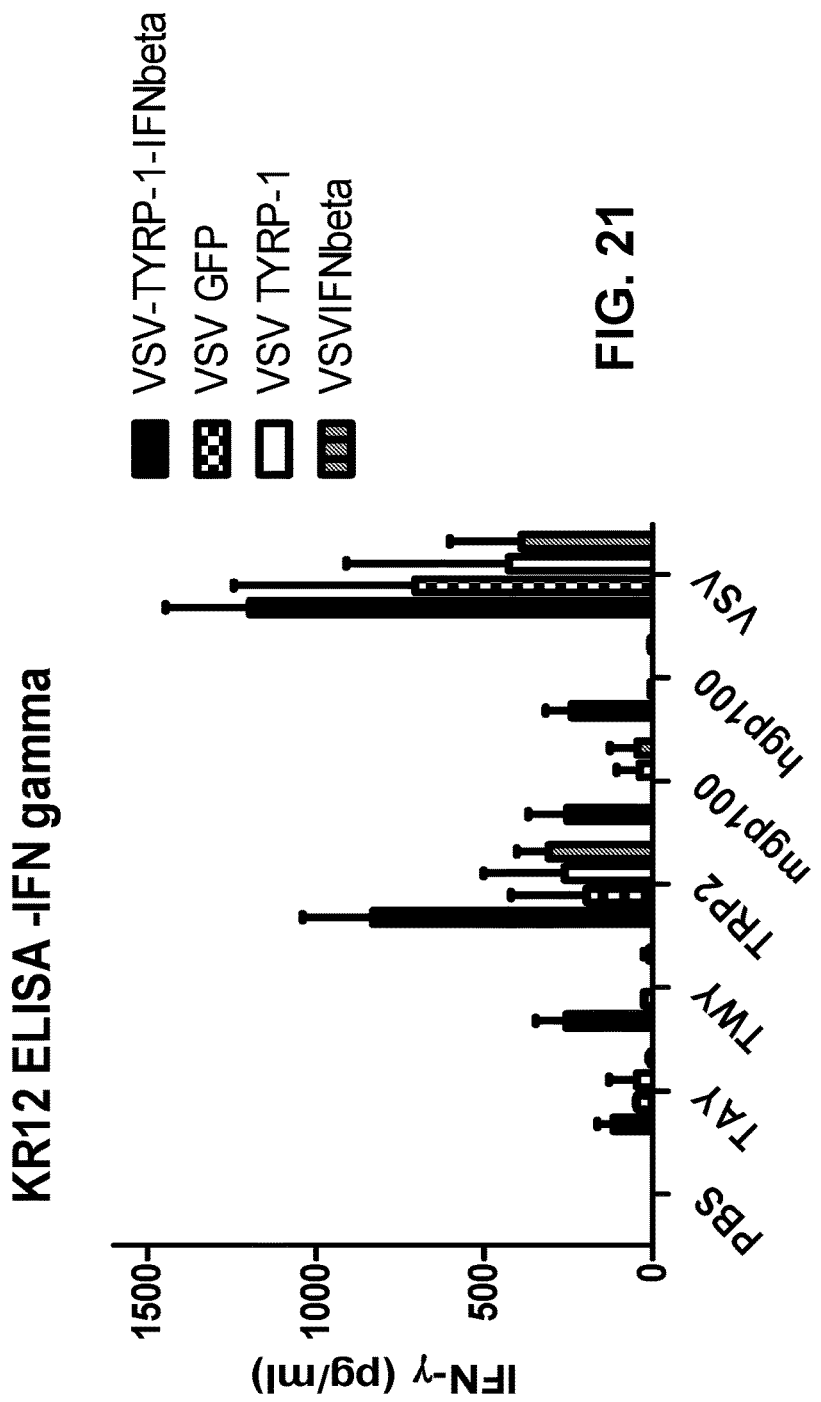

FIG. 21 is a bar graph plotting IFN-γ levels (pg/mL) for cells obtained from mice treated as indicated and stimulated with the indicated polypeptides.

Figure 22:
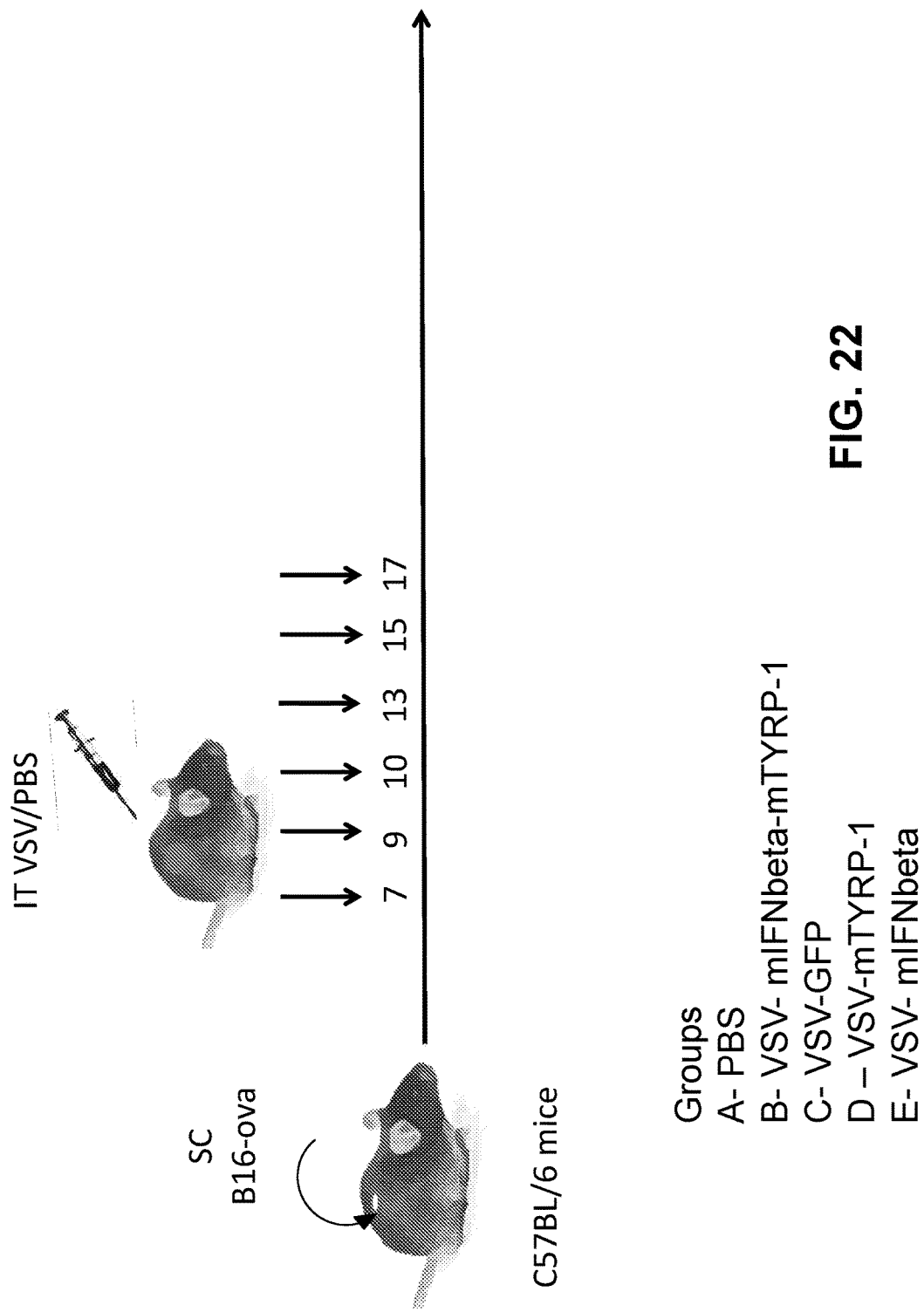

FIG. 22 is a schematic of an in vivo assay for assessing VSV vectors expressing IFN-β polypeptides.

Figure 23:
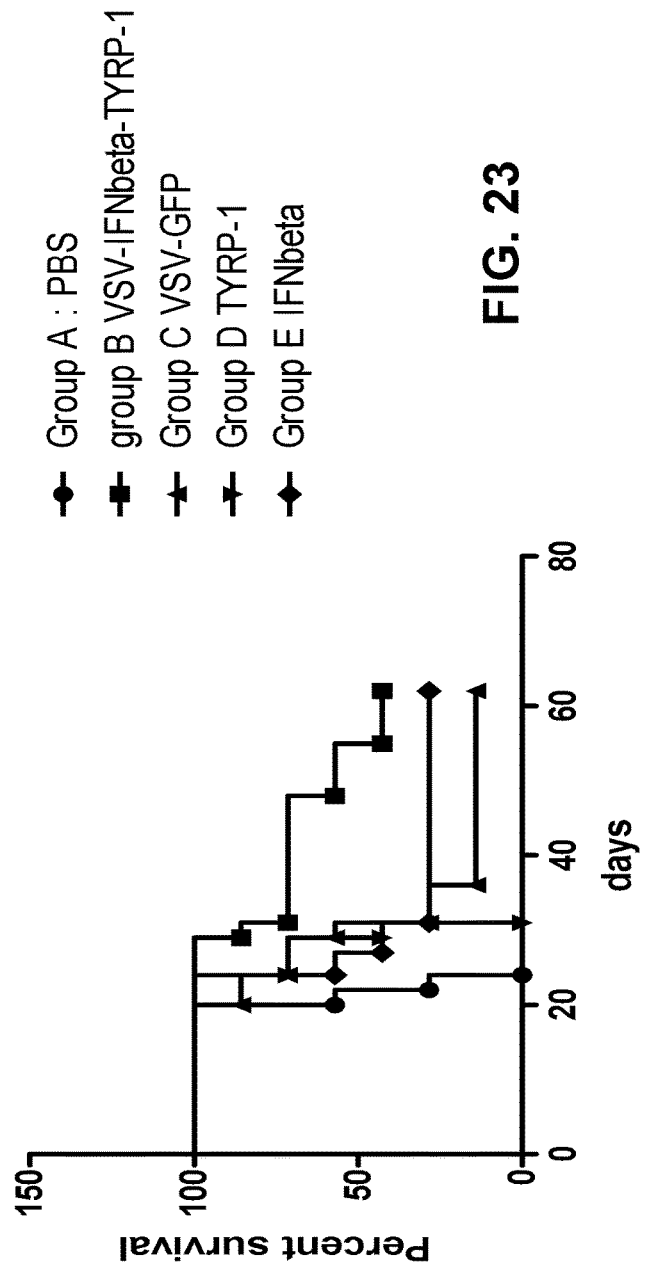

FIG. 23 is a graph plotting the percent survival of mice having B16 tumors and treated with the indicated VSV vectors.

DETAILED DESCRIPTION

This document provides methods and materials for treating cancer. For example, this document provides combinations of antigens having the ability to reduce the number of cancer cells within a mammal (e.g., a human). As described herein, combinations of antigens that include an N-RAS antigen, a TYRP1 antigen, and a CYT-C antigen, that include an HIF-2α antigen, a SOX-10 antigen, and a C-MYC antigen, or that include an HIF-2α antigen, a SOX-10 antigen, a C-MYC antigen, and a TYRP-1 antigen can be used to treat cancer. In some cases, combinations of antigens that include an N-RAS antigen, a TYRP1 antigen, and a CYT-C antigen, that include an HIF-2α antigen, a SOX-10 antigen, and a C-MYC antigen, or that include an HIF-2α antigen, a SOX-10 antigen, a C-MYC antigen, and a TYRP-1 antigen can be used to reduce the number of cancer cells present within a mammal.

The methods and materials provided herein can be used to treat cancer or to reduce the number of cancer cells present within any appropriate mammal such as humans, monkeys, horses, cows, sheep, dogs, cats, mice, or rats. In addition, the methods and materials provided herein can be used to treat any appropriate cancer or to reduce the number of appropriate type of cancer cells present within a mammal. For example, the methods and materials provided herein can be used to treat melanoma (e.g., skin melanoma or uveal melanoma), non-Hodgkin lymphoma, colorectal cancer, brain tumors, papillary thyroid carcinoma, non-small-cell lung carcinoma, or adenocarcinoma of the lung or can be used to reduce the number of melanoma (e.g., skin melanoma or uveal melanoma), non-Hodgkin lymphoma, colorectal cancer, brain tumor, papillary thyroid carcinoma, non-small-cell lung carcinoma, or adenocarcinoma of the lung cancer cells present within a mammal.

In some cases, a combination of an N-RAS antigen, a TYRP1 antigen, and a CYT-C antigen can be used to treat cancer (e.g., melanoma or a subcutaneous cancer). In some cases, one or more viral vectors (e.g., vesicular stomatitis virus (VSV) vectors) designed to express an N-RAS antigen, a TYRP1 antigen, and a CYT-C antigen can be used to treat cancer (e.g., melanoma or a subcutaneous cancer). For example, VSV vectors designed to express an N-RAS antigen, a TYRP1 antigen, and a CYT-C antigen can be administered to a mammal (e.g., a human) with melanoma to reduce the size or to prevent the additional growth of that melanoma.

In some cases, a combination of an HIF-2α antigen, a SOX-10 antigen, a C-MYC antigen, and a TYRP-1 antigen can be used to treat cancer (e.g., intracranial cancers or gliomas). In some cases, one or more viral vectors (e.g., VSV vectors) designed to express an HIF-2α antigen, a SOX-10 antigen, a C-MYC antigen, and a TYRP-1 antigen can be used to treat cancer (e.g., intracranial cancers or gliomas). For example, VSV vectors designed to express an HIF-2α antigen, a SOX-10 antigen, a C-MYC antigen, and a TYRP-1 antigen can be administered to a mammal (e.g., a human) with glioma to reduce the size or to prevent the additional growth of that glioma.

In some cases, a combination of an HIF-2α antigen, a SOX-10 antigen, and a C-MYC antigen can be used to treat cancer (e.g., melanomas). In some cases, one or more viral vectors (e.g., VSV vectors) designed to express an HIF-2α antigen, a SOX-10 antigen, and a C-MYC antigen can be used to treat cancer (e.g., melanomas). For example, VSV vectors designed to express an HIF-2α antigen, a SOX-10 antigen, and a C-MYC antigen can be administered to a mammal (e.g., a human) with melanoma to reduce the size or to prevent the additional growth of that melanoma.

An N-RAS antigen can have the amino acid sequence set forth in GenBank® Accession No. AAB29640 (GI No. 544859), or a fragment of such an amino acid sequence that is between about 7 and 400 amino acid residues (e.g., between about 10 and 400 amino acid residues, between about 15 and 400 amino acid residues, between about 20 and 400 amino acid residues, between about 25 and 400 amino acid residues, between about 30 and 400 amino acid residues, or between about 30 and 200 amino acid residues) in length. In some cases, a N-RAS antigen can have the amino acid sequence set forth in GenBank® Accession No. AAB29640 (GI No. 544859) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

A TYRP1 (tyrosinase-related protein 1) antigen can have the amino acid sequence set forth in GenBank® Accession No. CAG28611 (GI No. 47115303), NM_000550.2 (GI No. 169881242), CR407683.1 (GI No. 47115302), XM_005251574.1 (GI No. 530390132), or X51420.1 (GI No. 37512), or a fragment of such an amino acid sequence that is between about 7 and 527 amino acid residues (e.g., between about 10 and 527 amino acid residues, between about 15 and 527 amino acid residues, between about 20 and 527 amino acid residues, between about 25 and 527 amino acid residues, between about 30 and 527 amino acid residues, or between about 30 and 200 amino acid residues) in length. In some cases, a TYRP1 antigen can have the amino acid sequence set forth in GenBank® Accession No. CAG28611 (GI No. 47115303), NM_000550.2 (GI No. 169881242), CR407683.1 (GI No. 47115302), XM_005251574.1 (GI No. 530390132), or X51420.1 (GI No. 37512) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

A CYT-C antigen can have the amino acid sequence set forth in GenBank® Accession No. NP_061820 (GI No. 11128019), or a fragment of such an amino acid sequence that is between about 7 and 200 amino acid residues (e.g., between about 10 and 200 amino acid residues, between about 15 and 200 amino acid residues, between about 20 and 200 amino acid residues, between about 25 and 200 amino acid residues, between about 30 and 200 amino acid residues, or between about 30 and 150 amino acid residues) in length. In some cases, a CYT-C antigen can have the amino acid sequence set forth in GenBank® Accession No. NP_061820 (GI No. 11128019) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

An HIF-2α antigen can have the amino acid sequence set forth in GenBank® Accession No. NM_001430 (GI No. 262527236), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length. In some cases, a HIF-2α antigen can have the amino acid sequence set forth in GenBank® Accession No. NM_001430 (GI No. 262527236) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

A SOX-10 antigen can have the amino acid sequence set forth in GenBank® Accession No. BT020029 (GI No. 54696919), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length. In some cases, a SOX-10 antigen can have the amino acid sequence set forth in GenBank® Accession No. BT020029 (GI No. 54696919) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

A C-MYC antigen can have the amino acid sequence set forth in GenBank® Accession No. V00568 (GI No. 34815), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length. In some cases, a C-MYC antigen can have the amino acid sequence set forth in GenBank® Accession No. V00568 (GI No. 34815) or a fragment of such an amino acid sequence that is immunogenic and induces a robust IL-17 response. In some cases, such an antigen can include one or more mutations within the sequence provided in GenBank® provided that the mutant antigen induces a robust IL-17 response.

In some cases, an N-RAS, TYRP1, CYT-C, HIF-2α, SOX-10, or C-MYC antigen can have the amino acid sequence (or a fragment thereof) as found in a naturally-occurring mutated form. For example, an N-RAS antigen having the amino acid sequence (or a fragment thereof) as found in a naturally-occurring mutated form can have one or more of the following mutations: Q61R, Q61K, Q61 (dbSNP: rs11554290), GLY13ASP (dbSNP: rs121434596), GLY13ARG (dbSNP: rs121434595), THR50ILE, GLY60GLU (in Noonen syndrome 6), PRO34LEU, or GLY12ASP (condition: epidermal nevus, somatic). A TYRP1 antigen having the amino acid sequence (or a fragment thereof) as found in a naturally-occurring mutated form can have one or more of the following mutations: 1-BP DEL of 368A (condition: albinism, oculocutaneous, type III), SER166TER (dbSNP: rs104894130), ARG373TER, ARG356GLU, 1-BP DEL of 106T, 4-BP DEL of 1057AACA, or ARG93CYS (condition: albinism, oculocutaneous, type III). A HIF-2α antigen having the amino acid sequence (or a fragment thereof) as found in a naturally-occurring mutated form can have the following mutation: HIF-2α (530). A SOX-10 antigen having the amino acid sequence (or a fragment thereof) as found in a naturally-occurring mutated form can have one or more of the following mutations: Q125K, R43Q, A361V, G413S, G413D, H414Y, A424V, GLU189TER (dbSNP: rs74315514), TYR83TER (dbSNP: rs73415876), 6-BP INS at NT482, 2-BP DEL of 1076GA (condition: waardenburg syndrome, type 4c), SER135THR (dbSNP: rs74315515; condition: waardenburg syndrome, type 2e, without neurologic involvement), TYR313TER (dbSNP: rs74315516), SER251TER (dbSNP: rs74315518), 12-BP DEL in exon 5, GLN250TER (dbSNP: rs74315521), 1-BP DEL of 795G, 1-BP DEL of 915G (condition: peripheral demyelinating neuropathy, central dysmyelination, waardenburg syndrome, and hirschsprung disease), TYR207TER (dbSNP: rs74315519), GLN377TER (dbSNP: rs74315520), 1128-BP DEL/3-BP INS, ALA157VAL (dbSNP: rs121909117; condition: waardenburg syndrome, type 4c), 253-BP DEL, 1,777-BP DEL, 1-BP DEL of 506C, 2-BP DEL of 743AG, 1-BP DEL of 113G, 2T-G (condition: waardenburg syndrome, type 2e, without neurologic involvement), IVS4AS, A-C, −2, or GLN174PRO (condition: waardenburg syndrome, type 2e, with neurologic involvement). A C-MYC antigen having the amino acid sequence (or a fragment thereof) as found in a naturally-occurring mutated form can have one or more of the following mutations: PRO57SER (dbSNP: rs28933407), ASN86THR (dbSNP: rs121918683), GLU39ASP (dbSNP: rs121918684), or PRO59ALA (dbSNP: rs121918685).

In some cases, an N-RAS, TYRP1, CYT-C, HIF-2α, SOX-10, or C-MYC antigen can have an amino acid sequence that is truncated at the C terminus. For example, an N-RAS antigen can include the N-terminal sequence of a full length N-RAS polypeptide, while lacking a portion of the C-terminal sequence of a full length N-RAS polypeptide. In some cases, the length of the missing C-terminal sequence of a truncated antigen (e.g., a truncated N-RAS, TYRP1, CYT-C, HIF-2α, SOX-10, or C-MYC antigen) can be from 1 to about 300 (e.g., 1 to 275, 1 to 250, 1 to 225, 1 to 200, 1 to 175, 1 to 150, 1 to 125, 1 to 100, 1 to 75, 1 to 50, 1 to 25, 1 to 20, 1 to 15, 1 to 10, 5 to 275, 5 to 250, 5 to 225, 5 to 200, 5 to 175, 5 to 150, 5 to 125, 5 to 100, 5 to 75, 5 to 50, 5 to 25, 5 to 20, 5 to 15, 5 to 10, 10 to 275, 10 to 250, 10 to 225, 10 to 200, 10 to 175, 10 to 150, 10 to 125, 10 to 100, 10 to 75, 10 to 50, 10 to 25, 10 to 20, or 10 to 15) amino acid residues. In some cases, the length of the missing C-terminal sequence of a truncated antigen (e.g., a truncated N-RAS, TYRP1, CYT-C, HIF-2α, SOX-10, or C-MYC antigen) can be between about 0.01 percent to about 85 percent (e.g., about 0.01 percent to about 85 percent, about 0.01 percent to about 75 percent, about 0.01 percent to about 65 percent, about 0.01 percent to about 55 percent, about 0.01 percent to about 45 percent, about 0.01 percent to about 35 percent, about 0.01 percent to about 25 percent, about 0.01 percent to about 15 percent, about 0.01 percent to about 10 percent, about 0.01 percent to about 5 percent, about 0.1 percent to about 85 percent, about 1 percent to about 85 percent, about 5 percent to about 85 percent, about 5 percent to about 85 percent, about 5 percent to about 75 percent, about 5 percent to about 65 percent, about 5 percent to about 55 percent, about 5 percent to about 45 percent, about 5 percent to about 35 percent, about 5 percent to about 25 percent, about 5 percent to about 15 percent, about 5 percent to about 10 percent) of the length of the full length polypeptide.

In some cases, the combination of antigens used to treat cancer or reduce the number of cancer cells within a mammal (e.g., a human) can be antigens of another species (e.g., mouse, rat, pig, monkey, sheep, cow, dog, or cat). For example, a combination of mouse, rat, or monkey antigens can be used to treat cancer or reduce the number of cancer cells within a human. An example of a SOX-10 sequence from mouse is set forth in GenBank® Accession No. AF047043.1. Examples of C-MYC sequences from mouse are set forth in GenBank® Accession Nos. NM_001177354.1 (GI No. 293629269), NM_001177353.1 (GI No. 293629266), NM_001177352.1 (GI No. 293629263), and NM_010849.4 (GI No. 100913213). Examples of TYRP-1 sequences from mouse are set forth in GenBank® Accession Nos. NM_001282014.1 (GI No. 530537243), NM_031202.3 (GI No. 530537240), NM_001282015.1 (GI No. 530537245), and BC076598.1 (GI No. 49903295).

Any appropriate vector (e.g. a viral vector) can be used to deliver nucleic acid encoding an N-RAS, TYRP1, CYT-C, HIF-2α, SOX-10, C-MYC, or TYRP-1 antigen (or combination thereof) to cells of a mammal to treat cancer as described herein. For example, viral vectors for administering nucleic acids (e.g., a nucleic acid encoding an N-RAS, TYRP1, CYT-C, HIF-2α, SOX-10, C-MYC, or TYRP-1 antigen (or combination thereof)) to a mammal can be prepared using standard materials (e.g., packaging cell lines, helper viruses, and vector constructs). See, for example, *Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). A viral vector for delivering nucleic acid encoding an N-RAS, TYRP1, CYT-C, HIF-2α, SOX-10, C-MYC, or TYRP-1 antigen (or combination thereof) can be derived from, for example, animal viruses such as adenoviruses, adeno-associated viruses, retroviruses, lentiviruses, vaccinia viruses, vesicular stomatitis virus, herpes viruses, maraba virus, or papilloma viruses. In some cases, lentiviral vectors, vesicular stomatitis viral vectors, adenoviral vectors, adeno-associated viral vectors, or maraba viral vectors can be used to deliver nucleic acid encoding an N-RAS, TYRP1, CYT-C, HIF-2α, SOX-10, C-MYC, or TYRP-1 antigen (or combination thereof) to cells of a mammal to treat cancer as described herein. In some cases, VSV-IFNβ (e.g., human interferon) viral vectors such as those described elsewhere (Obuchi et al., *J. Virol.*, 77(16): 8843-56 (2003) and Jenks et al., *Hum. Gene Ther.*, 21(4): 451-62 (2010)) can be used to deliver nucleic acid encoding an N-RAS, TYRP1, CYT-C, HIF-2α, SOX-10, C-MYC, or TYRP-1 antigen (or combination thereof) to cells of a mammal to treat cancer.

Any appropriate method can be used to insert nucleic acid encoding an N-RAS, TYRP1, CYT-C, HIF-2α, SOX-10, C-MYC, or TYRP-1 antigen into a viral vector (e.g., a VSV vector). For example, the methods and materials described elsewhere (Kottke et al., *Nature Med.*, 17:854-9 (2011); and Pulido et al., *Nat. Biotechnol.*, 30:337-43 (2012)) can be used to insert nucleic acid encoding an N-RAS, TYRP1, CYT-C, HIF-2α, SOX-10, C-MYC, or TYRP-1 antigen into a VSV vector such that the antigen (e.g., the N-RAS, TYRP1, CYT-C, HIF-2α, SOX-10, C-MYC, or TYRP-1 antigen) is expressed in mammalian cells. Once obtained, a combination of VSV vectors having the ability to express an N-RAS antigen, a TYRP1 antigen, and a CYT-C antigen, an HIF-2α antigen, a SOX-10 antigen, and a C-MYC antigen, or an HIF-2α antigen, a SOX-10 antigen, a C-MYC antigen, and a TYRP-1 antigen (e.g., a combination of VSV-N-RAS, VSV-TYRP1, and VSV-CYT-C vectors, a combination of VSV-HIF-2α, VSV-SOX-10, and VSV-C-MYC vectors, or a combination of VSV-HIF-2α, VSV-SOX-10, VSV-C-MYC, and VSV-TYRP-1 vectors) can be administered to a mammal to treat cancer (e.g., melanoma such as uveal melanoma or a brain cancer such as glioma) or to reduce the number of cancer cells (e.g., melanoma cells such as uveal melanoma cells or a brain cancer cells such as glioma cells) present within a mammal. For example, once obtained, a combination of VSV vectors having the ability to express an HIF-2α antigen, a SOX-10 antigen, a C-MYC antigen, and a TYRP-1 antigen (e.g., a combination of VSV-HIF-2α, VSV-SOX-10, VSV-C-MYC, and VSV-TYRP-1 vectors) can be administered to a mammal to treat cancer (e.g., glioma) or to reduce the number of cancer cells (e.g., glioma cells) present within a mammal.

Any appropriate method can be used to administer viral vectors (e.g., VSV vectors) designed to express an N-RAS antigen, a TYRP1 antigen, and a CYT-C antigen, an HIF-2α antigen, a SOX-10 antigen, and a C-MYC antigen, or an HIF-2α antigen, a SOX-10 antigen, a C-MYC antigen, and a TYRP-1 antigen to a mammal having cancer. For example, intratumoral, subcutaneous, intravenous, intracranial, sub dermal, and intraperitoneal administrations can be used to administer viral vectors (e.g., VSV vectors) designed to express an N-RAS antigen, a TYRP1 antigen, and a CYT-C antigen, an HIF-2α antigen, a SOX-10 antigen, and a C-MYC antigen, or an HIF-2α antigen, a SOX-10 antigen, a C-MYC antigen, and a TYRP-1 antigen to a mammal having cancer (e.g., uveal melanoma or a brain cancer such as glioma). Once the viral vectors are administered to a mammal, the mammal can be monitored to confirm a reduction in the number of cancer cells present within the mammal. For example, imaging techniques such as MRI and CT scans can be used to confirm that the number of cancer cells present within the mammal is reduced following administration of the viral vectors. In some cases, the following examination criteria can be used. A non-nodal lesion is considered measurable if its longest diameter can be accurately measured as 2.0 cm with chest x-ray, or as =1.0 cm with CT scan or MRI. A superficial non-nodal lesion is measurable if its longest diameter is =1.0 cm in diameter as assessed using calipers (e.g., skin nodules) or imaging. In the case of skin lesions, documentation by color photography, including a ruler to estimate the size of the lesion, can be used. A malignant lymph node is considered measurable if its short axis is >1.5 cm when assessed by CT scan (CT scan slice thickness recommended to be no greater than 5 mm). In physical examinations for superficial non-nodal lesions, physical examination is acceptable, but imaging is preferable. In the case of skin lesions, documentation by color photography, including a ruler to estimate the size of the lesion, can be used.

In some cases, an N-RAS antigen, a TYRP1 antigen, and a CYT-C antigen, an HIF-2α antigen, a SOX-10 antigen, and a C-MYC antigen, or an HIF-2α antigen, a SOX-10 antigen, a C-MYC antigen, and a TYRP-1 antigen can be administered as a combination in the form of polypeptides. For example, an N-RAS antigen, a TYRP1 antigen, and a CYT-C antigen (each in the form of polypeptides) can be formulated with an adjuvant such as such as alum, monophosphoryl lipid A, liposomes, QS21, MF-59, or immunostimulating complexes (ISCOMS) and administered to a mammal having cancer (e.g., melanoma). Following this administration, the number of cancer cells present within the mammal can be reduced. In some cases, an HIF-2α antigen, a SOX-10 antigen, a C-MYC antigen, and a TYRP-1 antigen can be administered as a combination in the form of polypeptides to a mammal having cancer (e.g., a brain cancer such as glioma). In some cases, an HIF-2α antigen, a SOX-10 antigen, and a C-MYC antigen can be administered as a combination in the form of polypeptides to a mammal having cancer (e.g., melanoma). Following this administration, the number of cancer cells present within the mammal can be reduced.

In some cases, therapy with a combination of antigens provided herein can include the use of radiation. For example, when treating cutaneous melanoma or a brain cancer such as glioma, a patient can be treated with both radiation and a combination of antigens provided herein.

In some cases, therapy with a combination of antigens provided herein can include the administration of one or more immune checkpoint inhibitors. For example, a combination of viral vectors (e.g., VSV vectors) designed to express an N-RAS antigen, a TYRP1 antigen, and a CYT-C antigen, an HIF-2α antigen, a SOX-10 antigen, and a C-MYC antigen, or an HIF-2α antigen, a SOX-10 antigen, a C-MYC antigen, and a TYRP-1 antigen can be administered in combination with one or more immune checkpoint inhibitors to treat a mammal having cancer. Examples of immune checkpoint inhibitors include, without limitation, anti-PD1 antibodies, anti-CTLA4 antibodies, anti-PDL1 antibodies, anti-PDL2 antibodies, anti-CD40 ligand antibodies, and anti KIR antibodies.

The invention will be further described in the following examples, which do not limit the scope of the invention described in the claims.

EXAMPLES

Example 1—Local Microenvironment Determines the Combination of Tumor Antigens that can be Used Successfully as Immunotherapy Agents Against Brain Cancer Cell Lines Murine B16ova melanoma cells (H2-K$^b$) were derived from B16 cells transduced with a cDNA encoding the chicken ovalbumin gene (Linardakis et al., *Cancer Res.*, 62:5495-504 (2002)). Cell lines were grown in Dulbecco's Modified Eagle's Medium (DMEM; Life Technologies, Carlsbad, Calif.) supplemented with 10% (v/v) fetal calf serum (FCS; Life Technologies, Carlsbad, Calif.), L-glutamine (Life Technologies, Carlsbad, Calif.), and 5 mg/mL G418 (Mediatech, Manassas, Va.) to select for retention of the ova gene. All cell lines were routinely monitored and found to be free of *Mycoplasma* infection. TRAMP-C2 (TC2) cells are derived from a prostate tumor that arose in a TRAMP mouse (H-2k$^b$) and were characterized by Dr Esteban Celis. TC2 cells grow in an androgen-independent manner and are routinely grown as tumors in C57BL/6 male mice (Kottke et al., *Cancer Res.*, 67:11970-9 (2007)).

Mice

C57BL/6 mice (Thy 1.2$^+$) were purchased from The Jackson Laboratory (Bar Harbor, Me.) at 6-8 weeks of age. The OT-I mouse strain is on a C57BL/6 background (H2-K$^b$) and expresses a transgenic T cell receptor Vα2 specific for the SIINFEKL peptide of ovalbumin in the context of MHC class I, H-2K$^b$ (Hogquist et al., *Cell*, 76:17-27 (1994)). OT-I breeding pairs were obtained from Dr. Larry Pease (Mayo Clinic, Rochester, Minn.). Pmel-1 transgenic mice (C57BL/6 background) express the Vα1/Vβ13 T cell receptor that recognizes amino acids 25-33 of gp100 of pmel-17 presented by H2-D$^b$ MHC class I molecules (Overwijk et al., *J. Exp. Med.*, 198:569-80 (2003)). Pmel-1 breeding colonies were purchased from The Jackson Laboratory at 6-8 weeks of age.

Viruses

The ASMEL VSV-cDNA library was generated as described herein and elsewhere (Kottke et al., *Nature Med.*, 17:854-9 (2011); and Pulido et al., *Nat. Biotechnol.*, 30:337-43 (2012)). Briefly, cDNA from two human melanoma cell lines, Mel624 and Mel888, was pooled, cloned into the pCMV.SPORT6 cloning vector (Invitrogen, CA) and amplified by PCR. The PCR amplified cDNA molecules were size fractionated to below 4 kbp for ligation into the parental VSV genomic plasmid pVSV-XN2 (Fernandes et al., *J Virol.*, 76:895-904 (2002)) between the G and L genes. The complexity of the ASMEL cDNA library cloned into the VSV backbone plasmid between the Xho1-Nhe1-sites was $7.0 \times 10^6$ colony forming units. Virus was generated from BHK cells by co-transfection of pVSV-XN2-cDNA library DNA along with plasmids encoding viral genes as described elsewhere (Fernandes et al., *J. Virol.*, 76:895-904 (2002)). Virus was expanded by a single round of infection of BHK cells and purified by sucrose gradient centrifugation.

VSV-GFP and VSV-ova (Indiana serotype) were generated by cloning the cDNA for green fluorescence protein (GFP) or chicken ovalbumin, respectively, into the plasmid pVSV-XN2 as described elsewhere (Fernandes et al., *J. Virol.*, 76:895-904 (2002)). pVSV-hgp100 was constructed by PCR amplifying the human gp100 cDNA, which was prepared from Mel88 cells using forward (5'-ATCTCGA-GATGGATCTGGTGCTAAAAAGATGC-3' (SEQ ID NO:1)) and reverse (5'-ATGCTAG-CTCAGACCTGCTGC-CCACT-3'(SEQ ID NO:2)) primers. The PCR product was then digested and inserted into the XhoI and NheI site of the VSV-XN2 vector, which is a genomic plasmid of VSV Indiana serotype (provided by Dr. John Rose, Yale University) to yield the pVSV-hgp100 plasmid. Recombinant VSV-hgp100 was recovered based on a method described elsewhere (Lawson et al., *PNAS*, 92:4477-4481 (1995); and Ramsburg et al., *J. Virol.*, 79:15043-15053 (2005)). Bulk amplification of plaque-purified VSV was performed by infecting BHK-21 cells (MOI=0.01) for 24 hours. Filtered supernatants were harvested and subjected to two rounds of 10% sucrose (10% w/v) in 1×PBS (Mediatech, Herndon, Va., USA) cushion centrifugation at 27,000 r.p.m. for 1 hour at 4° C. The pelleted virus was resuspended in 1× phosphate buffered saline (PBS), aliquoted, and stored at −80° C. Viral titers were measured by standard plaque assay on BHK-21 cells (Diaz et al., *Cancer Res.*, 67:2840-8 (2007)).

In Vivo Studies

To establish subcutaneous (s.c.) tumors, $5 \times 10^5$ B16ova tumor cells in 100 μL of PBS were injected into the flanks of C57BL/6 mice. To establish intracranial (i.c.) brain tumors, $10^4$ cells were injected stereotactically (1 mm anterior and 2 mm lateral to the bregma) using a syringe bearing a 26G needle 2.5 mm into the brains of C57BL/6 mice.

Virus or PBS control (100 μL) was administered intravenously following tumor establishment (day 5 post cell implantation) and occurred every other day as dictated by the specific study (see results and figure descriptions for specifics).

Naive Pmel-1 T cells were isolated from the spleens and lymph nodes of OT-I and pmel-1 transgenic mice, respectively. Single cell suspensions were prepared by crushing tissues through a 100 μm filter, and red blood cells were removed by incubation in ACK buffer (sterile distilled $H_2O$ containing 0.15 mol/L $NH_4Cl$, 1.0 mmol/L $KHCO_3$, and 0.1 mmol/L EDTA adjusted to pH 7.2-7.4) for 2 minutes. CD8$^+$ T cells were isolated using the MACS CD8a (Ly-2) microbead magnetic cell sorting system (Miltenyi Biotec, Auburn, Calif.). For adoptive transfer experiments, mice were intravenously administered naïve ($1 \times 10^6$ total cells in 100 μL PBS) Pmel-1 cells after tumor establishment. Mice were examined daily for overall health as well as changes in whisker and coat pigmentation. For s.c. tumors, tumor sizes were measured three times weekly using calipers, and mice were euthanized when tumor size was approximately 1.0 cm×1.0 cm in two perpendicular directions.

IL-2Cx, a conjugate of murine IL-2 (2 μg/mouse) preincubated in vitro with anti-mouse IL-2 Ab (10 μg per mouse) at 4° C. for 18 hours, was injected intravenously in 100 μL PBS to enhance T cell co-stimulation in vivo.

Quantitative rtPCR

Tumors were immediately excised from euthanized mice and dissociated in vitro to achieve single-cell suspensions. RNA was extracted from cells using the Qiagen RNeasy kit (Qiagen, Valencia, Calif.). cDNA was made from 1 μg total cellular RNA using the First Strand cDNA Synthesis Kit (Roche, Indianapolis, Ind.). A cDNA equivalent of 1 ng RNA was amplified by PCR with gene-specific primers. Expression of mGAPDH was used as a positive control/reference gene for expression of genes being quantified by qrtPCR. mGAPDH sense: TCATGACCACAGTC-CAT-GCC (SEQ ID NO:3), mGAPDH antisense: TCA-GCTCTGGGATGACCTTG (SEQ ID NO:4).

qrtPCR was carried out using a LightCycler480 SYBR-GreenI Master kit and a LightCycler480 instrument (Roche) according to the manufacturer's instructions. Typically, RNA was prepared from equal numbers of cells from each sample (usually 5000 cells) and reverse transcribed as described herein. PCR (primers at 0.5 μM, annealing=58° C.) was run with diluted cDNA samples (neat, 1:10, 1:100, 1:1000). GAPDH amplification was used as a control for equal loading of target cDNAs. The threshold cycle (Ct) at which amplification of the target sequence was detected was used to compare the relative levels of mRNA between samples. Relative quantities of the target gene mRNA were normalized with Ct of GAPDH amplification.

In vitro splenic T cell reactivation and enzyme-linked immunosorbent assay (ELISA) for IFN-γ/IL-17/HIF-2α. Spleens and lymph nodes were immediately excised from euthanized mice and dissociated in vitro to achieve single-cell suspensions. Red blood cells were lysed with ACK lysis buffer for 2 minutes as described herein. Cells were resuspended at $1 \times 10^6$ cells/mL in Iscove's Modified Dulbecco's Medium (IMDM; Gibco, Grand Island, N.Y.)+5% FBS+1% Pen-Strep+40 μM 2-ME. Supernatants were harvested from $10^6$ LN/splenocytes previously stimulated with virus stocks as described herein, with the H-2K$^b$-restricted peptide ova$_{257-264}$ (SIINFEKL peptide (SEQ ID NO:5); 2.5 μg/mL) and/or with freeze thaw lysates from tumor cells in triplicate, every 24 hours for 3 days. 48 hours later, cell-free supernatants were collected and tested by ELISA for IL-17 (R&D Systems) or IFN-γ (BD Biosciences). HIF-2α polypeptide was measured using a sandwich enzyme immunoassay as per the manufacturer's instructions (USCN Life Sciences Inc., Houston, Tx).

In Vitro Tumor Cell/Brain Homogenate Co-Cultures

B16ova cells ($10^5$/well) were co-cultured with PBS, lysate from dissociated brain cells, freeze/thawed ×3 (equivalent of $10^7$ cells per well), or with $10^7$ cells/well from dissociated mouse brains. 24 and 48 hours later further PBS, F/T lysate or brain homogenates were added to the wells. 24 hours later, cultures were washed 3 times with PBS, and cDNA was prepared and screened by qrtPCR for expression of HIF-2α relative to GAPDH. Brain homogenates were depleted for immune cell types by 24 hour incubation with depleting antibodies. CD11b+ cells were purified from brain homogenates using CD11b microbeads (Miltenyi Biotech, Auburn, Calif.) as directed by the manufacturer.

Statistics

Survival data from the animal studies were analyzed by the log-rank test using GraphPad Prism 5 (GraphPad Software, La Jolla, Calif.). Two-sample, unequal variance Student's t-test analysis was applied for in vitro data. Statistical significance was determined at the level of P<0.05.

VSV-Expressing a Foreign Model TAA Treats Intra-Cranial Tumors

Systemic delivery of VSV expressing OVA, a defined tumor associated antigen of B16ova tumors, significantly prolonged survival of mice with established intra-cranial B16ova tumors (p=0.0259 compared to VSV-GFP), but was unable to generate any cures (FIG. 1A). As determined for subcutaneous B16ova tumors, which escaped from adoptive T cell transfer therapy with ova-specific OT-I T cells (KALUZA), i.c. tumors, which developed following VSV-ova treatment, lost expression of the target OVA antigen.

Figure 1B:
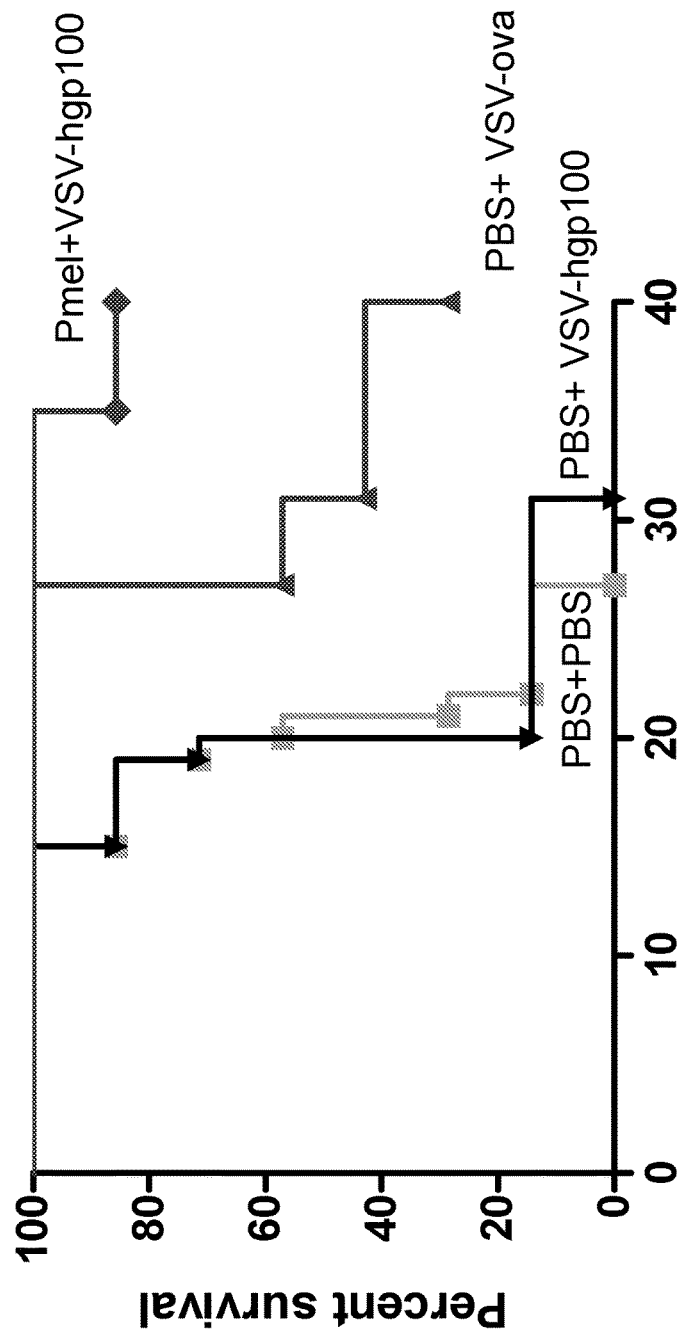

VSV-Expressing a Single Endogenous, Self TAA is Ineffective Against Intra-Cranial Tumors OVA is a foreign, non-self TAA, against which no tolerance exists in C57BL/6 mice. Therefore, the same treatment of i.c. B16ova tumors was tested using VSV-hgp100, targeting an endogenous self TAA, against which tolerance is intact in C57BL/6 mice. Although i.v. VSV-hgp100 generated weak T cell responses against the gp100 antigen, no significant therapy against i.c. B16ova tumors was generated in vivo (FIG. 1B), and all the tumors recovered from these mice retained unchanged levels of gp100 expression. Although adoptive transfer of naïve Pmel hgp100 antigen-specific T cells has no therapeutic effect compared to PBS (Kaluza et al., *Hum. Gene Ther.*, 23:1054-64 (2012); and Rommelfanger et al., *Cancer Res.*, 72:4753-64 (2012)), it was possible to cure >80% of mice bearing i.c. B16ova tumors by combining i.v. VSV-hgp100 with adoptive transfer of naïve PMEL antigen-specific T cells (FIG. 1B).

VSV-cDNA Library Treats Brain Tumors

Intravenous treatment of mice with the ASMEL VSV-cDNA library, constructed from cDNA of human melanoma cells (Pulido et al., *Nat. Biotechnol.*, 30:337-43 (2012)) significantly extended survival of mice bearing 5 day established i.c. B16ova tumors (p<0.0001 compared to VSV-GFP) (FIG. 2A). Although the ASMEL VSV-cDNA did not generate any long term cures, it was significantly more effective than VSV-mediated expression of either a truly self TAA (gp100, no therapy, (FIG. 1B)) or a non-tolerized, foreign TAA (VSV-ova, (FIG. 1A)) in two separate experiments.

ASMEL Boosts a Tumor-Primed Th17 Memory Response

Figure 2B:
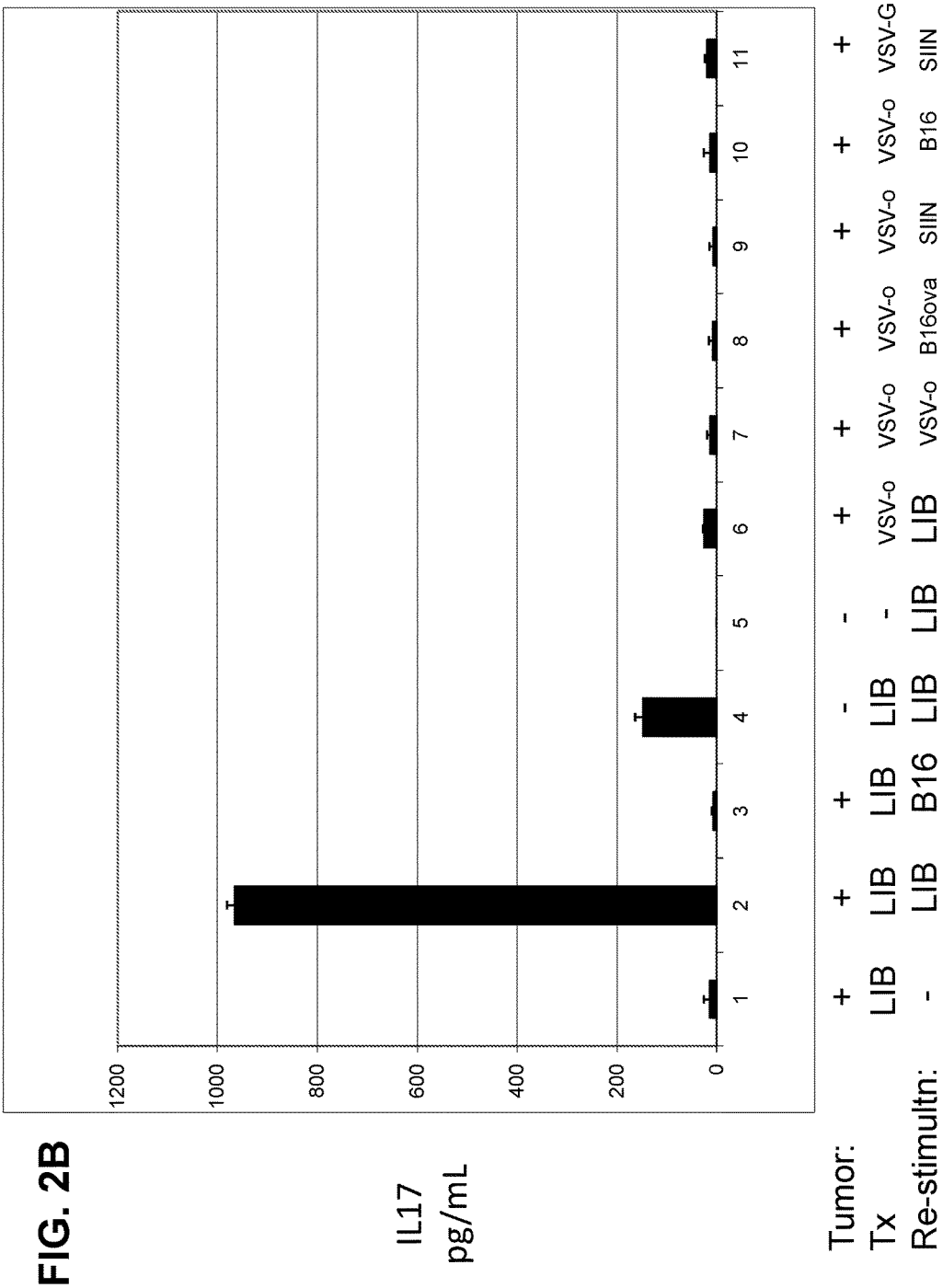

Anti-tumor efficacy of VSV-cDNA libraries can correlate with the ability of splenocyte/LN cells from VSV-cDNA library treated, tumor-cured mice to mount an IL-17 (Kottke et al., *Nature Med.*, 17:854-9 (2011); and Pulido et al., *Nat. Biotechnol.*, 30:337-43 (2012)) or IFN-γ (Boisgerault et al., *Mol. Ther.*, 21:1507-16 (2013)) recall response in vitro upon re-stimulation with either tumor targets or the library itself. Splenocyte/lymph node (Splen/LN) cells from C57BL/6 mice bearing intra-cranial B16ova tumors, and which had been treated with the ASMEL, secreted IL-17 and IFN-γ in response to re-stimulation in vitro with the ASMEL (FIGS. 2B and 2C). Interestingly, Splen/LN from mice which had no primary tumor, but were treated with ASMEL, secreted significantly reduced amounts of IL-17 upon in vitro re-stimulation with the ASMEL (FIG. 2B), but exhibited a similar memory IFN-γ recall response (FIG. 2C). This IFN-γ response was predominantly directed against VSV antigens because, although tumor bearing mice treated with the ASMEL did not have an IL-17 recall response to VSV-ova, VSV-gp100, or VSV-GFP, they did have a Th1, IFN-γ memory response in all cases (FIG. 2B). This Th1, IFN-γ response was absent when re-stimulation was with cells or peptide, and not VSV, unless an antigen specific response was stimulated (such as an ova-specific response in B16ova cells or SIINFEKL peptide following VSV-ova treatment) (FIG. 2C).

Despite having shown significant therapy against i.c. B16 tumors, splen/lymph node cells from C57BL/6 mice bearing intra-cranial B16ova tumors, which were treated with the ASMEL, did not secrete IL-17 (or IFN-γ) when re-stimulated in vitro with lysates of cultured B16ova cells (FIGS. 2B and 2C). This was in contrast to other findings where spleen/LN from mice in which subcutaneous B16 tumors were cured by treatment with the ASMEL had a memory response against both the ASMEL and cultured B16 cells (Pulido et al., *Nat. Biotechnol.*, 30:337-43 (2012)), and in mice treated with VSV-ova which had a demonstrable recall response (although Th1 not Th17) against tumor targets expressing OVA or against the SIINFEKL peptide epitope of OVA (FIG. 2C).

Identification of Brain Tumor Antigens

Figure 2D:
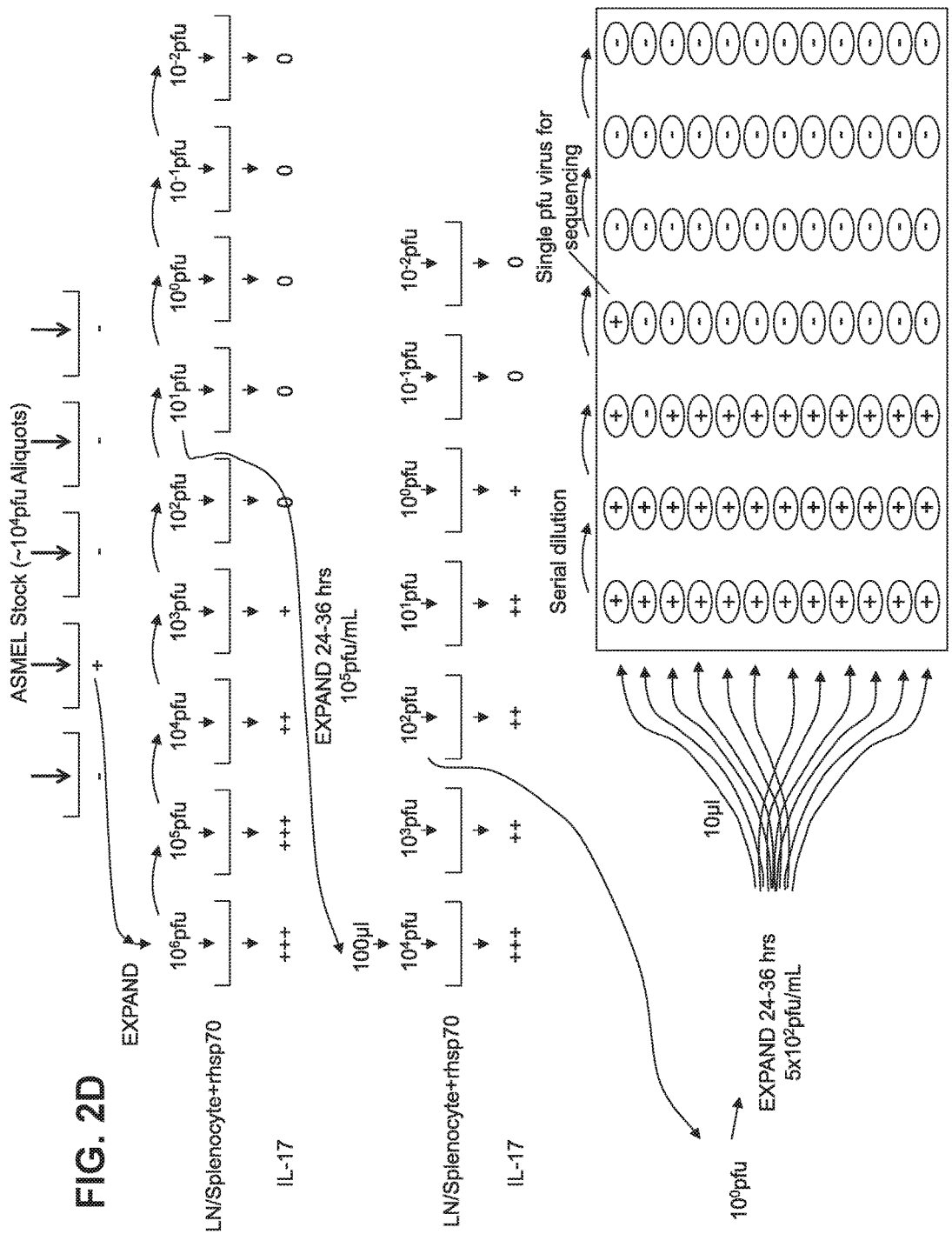

The ability of Splen/LN cells from tumor-bearing, ASMEL-treated mice to secrete IL-17 upon in vitro re-stimulation with the ASMEL was exploited to identify individual VSV-cDNA viruses that encode polypeptides that are immunogenic targets of this IL-17 memory response. Using an assay previously validated to clone immunogenic polypeptides from VSV-cDNA libraries (Kottke et al., *Nature Med.*, 17:854-9 (2011); and Boisgerault et al., *Mol. Ther.*, 21:1507-16 (2013)), including the ASMEL (Pulido et al., *Nat. Biotechnol.*, 30:337-43 (2012)), the highest dilution of the ASMEL that was still active in stimulating an IL-17 recall response was isolated from Splen/LN (FIG. 2D). Limiting dilution cloning from this highly diluted stock identified single VSV encoding 5' cDNA sequences from human Hypoxia-Inducible Factor 2α (Rode et al., *J. Immunol.*, 189:3168-77 (2012)), SOX-10 (Shakhova et al., *Nat. Cell Biol.*, 14:882-90 (2012)), C-MYC (Zhuang et al., *Oncogene*, 27:6623-34 (2008)), and TYRP-1 (Pulido et al., *Nat. Biotechnol.*, 30:337-43 (2012); and Shibata et al., *Biochem Biophy Res. Commun.*, 184:568-75 (1992)).

Anatomical Location of Tumor Affects Antigen Expression

Figure 3A:
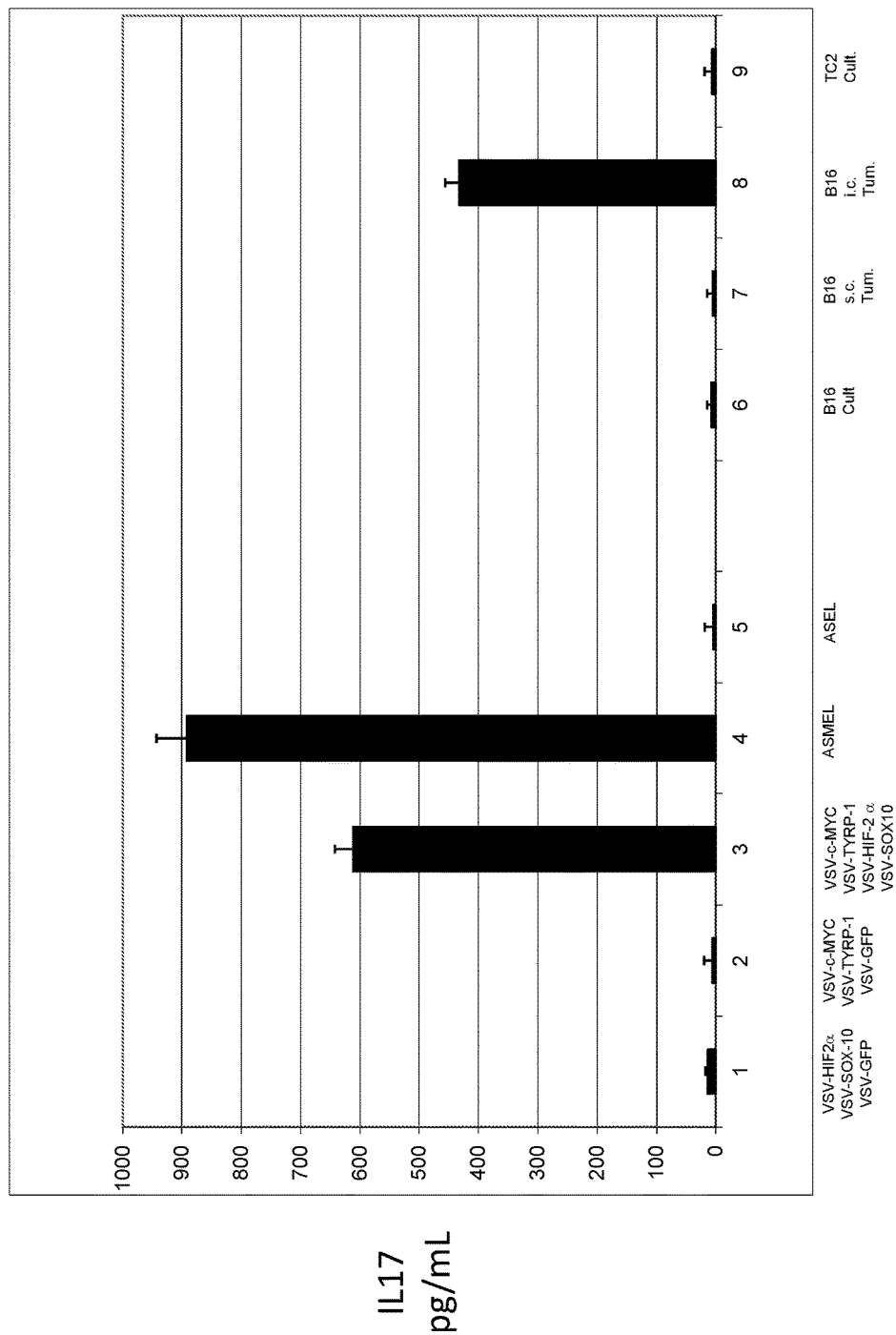
FIGS. 3A-C. Tumor associated antigen (TAA) expression is determined by anatomical location of the tumor.

Consistent with the observations in the s.c. model of B16 tumors (Pulido et al., *Nat. Biotechnol.*, 30:337-43 (2012)), re-stimulation of Splen/LN from tumor bearing, ASMEL-treated mice with any of these VSV-cDNA individually, in pairs or triple combinations, did not induce significant IL-17 (FIG. 3A). However, when all four were combined, at the same total dose of virus, an IL-17 recall response was induced in vitro at similar levels to that induced by re-stimulation with the intact, unfractionated ASMEL itself (FIG. 3A).

Figure 3B:
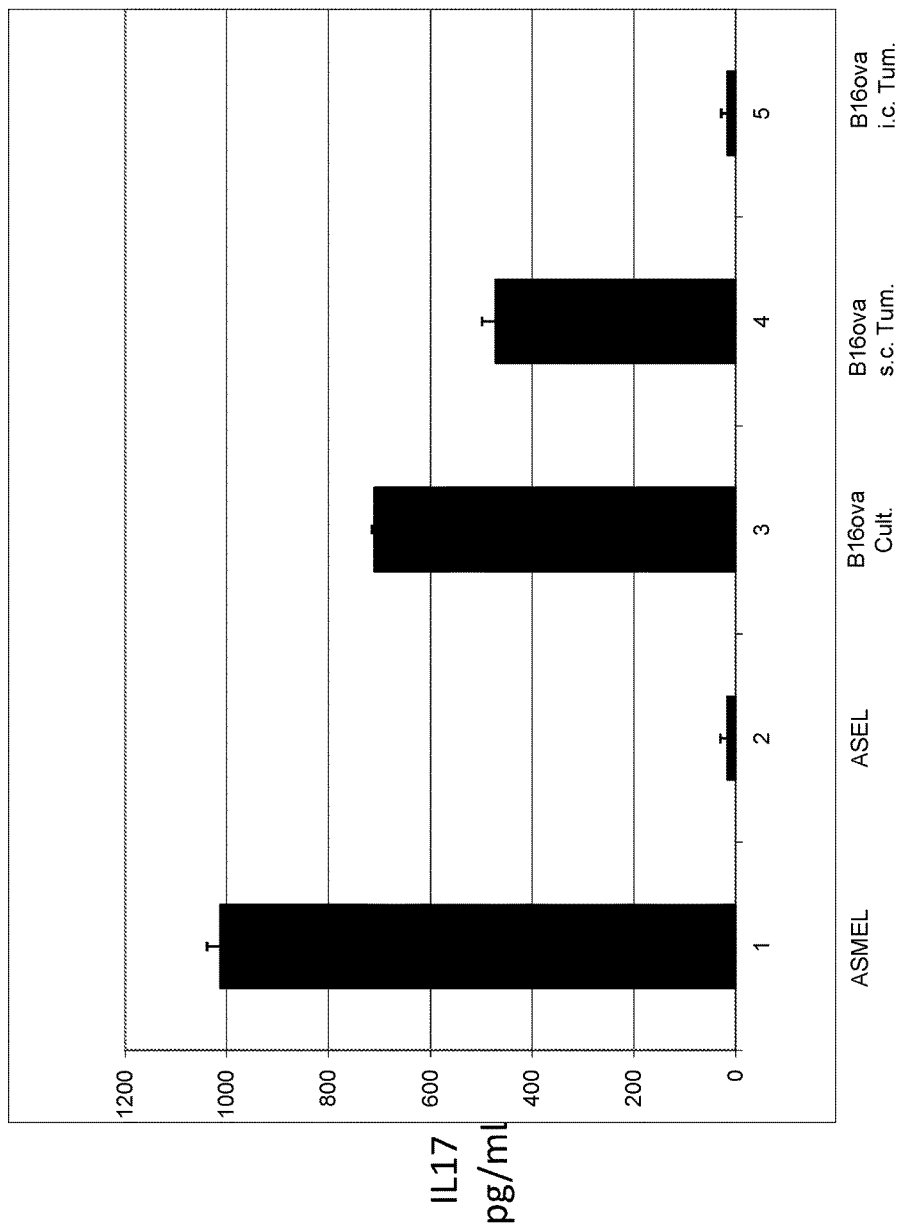

As before (FIG. 2B), the IL-17 recall response was not evoked from Splen/LN of mice treated for i.c. B16 tumors with the ASMEL upon re-stimulation with cultured B16ova targets (FIG. 3A). This contrasts with a strong IL-17 recall response from Splen/LN of mice treated successfully for s.c. B16ova tumors with the ASMEL when re-stimulated with cultured B16ova tumor targets (FIG. 3B). However, the IL-17 recall response was effectively induced from Splen/

LN of mice with i.c. B16ova tumors, treated with the ASMEL, upon re-stimulation with B16 cells recovered directly from B16ova brain tumors (FIG. 3A). Splen/LN from mice treated for s.c. B16ova tumors with the ASMEL were not re-stimulated with brain tumor-derived B16 targets (FIG. 3B).

Figure 3C:
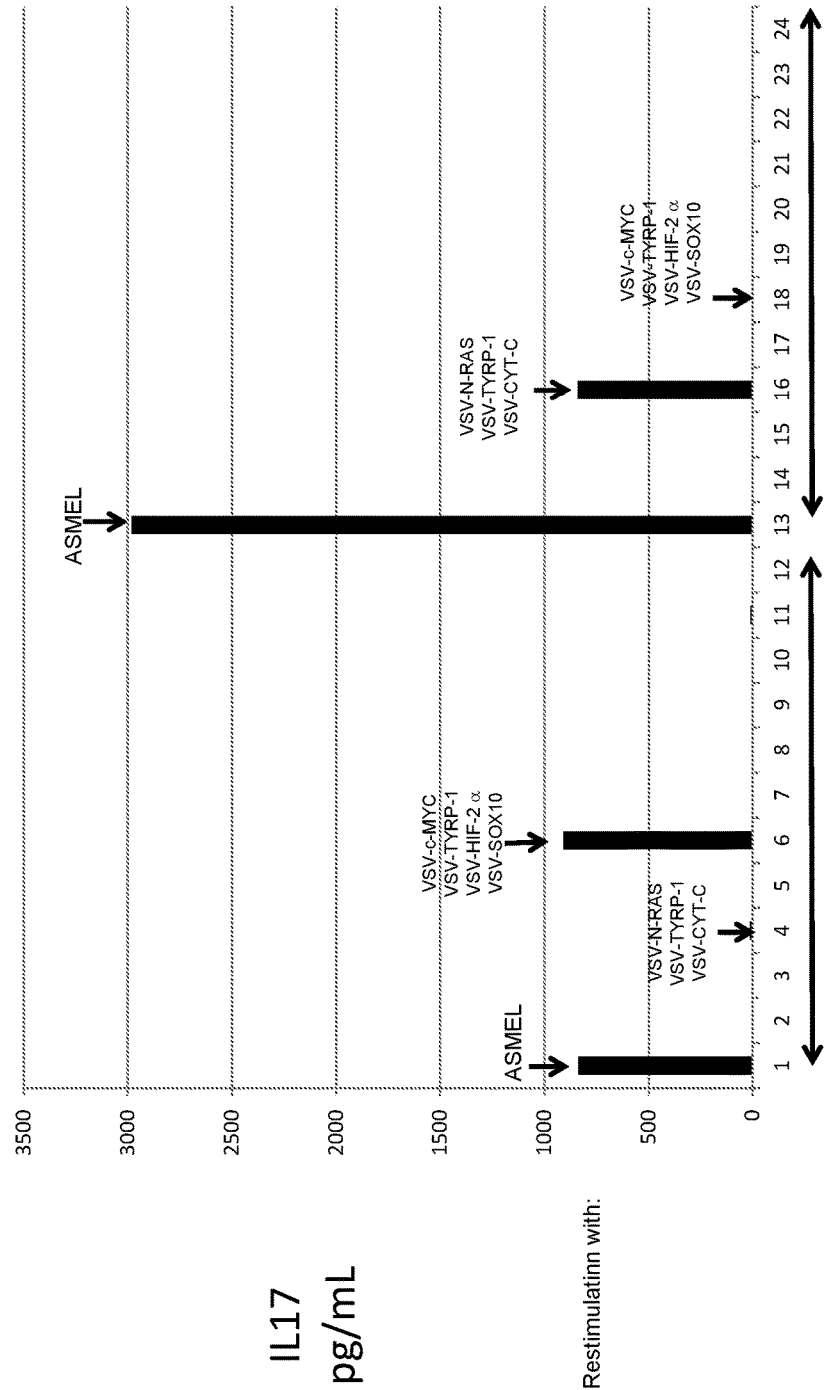

Next, the hypothesis that B16 tumors growing in the brain express a distinct set of potentially immunogenic TAA, compared to B16 tumors growing s.c., against which a Th17 response can be raised by the presence of the tumor and which can then be boosted by i.v. treatment with the ASMEL, was tested. Consistent with this hypothesis, Splen/LN from mice bearing i.c. B16 tumors, treated with the ASMEL, secreted high levels of IL-17 upon re-stimulation with either the unfractionated ASMEL or the combination of VSV-HIF-2α+VSV-SOX-10+VSV-c-myc+VSV-TYRP-1, but not with other combinations of VSV-cDNA, including VSV-N-RAS+VSV-CYT-C+VSV-TYRP-1 (FIG. 3C). In contrast, Splen/LN from mice bearing s.c. B16 tumors, treated with the ASMEL, also secreted high levels of IL-17 upon re-stimulation with the unfractionated ASMEL, but not with the combination of VSV-HIF-2α+VSV-SOX-10+VSV-c-myc+VSV-TYRP-1; however, re-stimulation with VSV-N-RAS+VSV-CYT-C+VSV-TYRP-1, which was therapeutically active against s.c. B16 tumors, generated high levels of IL-17 (FIG. 3C).

Brain Tumors Express a Specific Profile of Potential Tumor Antigens

Figure 4A:
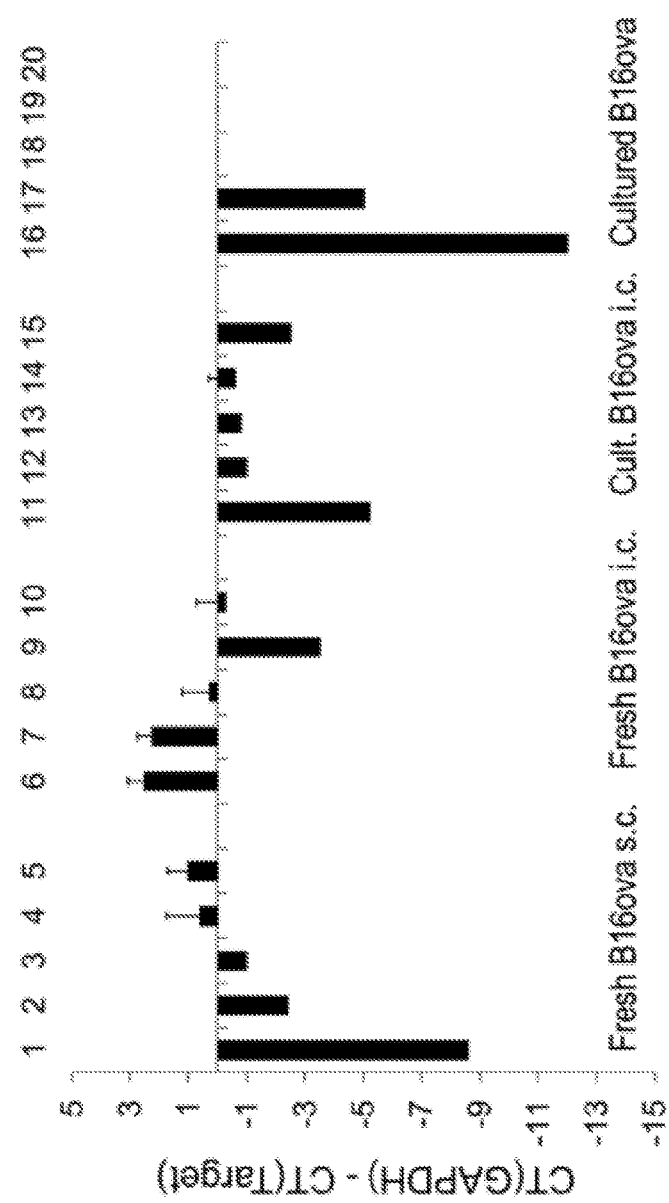
FIGS. 4A-C. Intra-cranial and subcutaneous tumor phenotypes are very distinct.

B16 cells recovered from different environments were tested for the expression of the antigens identified as immunogenic from either s.c. or i.c. tumors. B16 cells maintained in vitro, and the source for implantation of both s.c. and i.c. tumors, expressed low (CT GAPDH-gene <0) levels of both HIF-2α and c-myc and moderate levels of TYRP-1, N-RAS, and CYT-C mRNA (FIG. 4A). The critical threshold cycle (CT) is defined as the cycle at which the fluorescence becomes detectable above background and is inversely proportional to the logarithm of the initial number of template molecules. A standard curve was plotted for each primer-probe set with CT values obtained from amplification of known quantities of plasmid DNA coding for either GAPDH. The standard curves were used to transform CT values of the experimental samples to the relative number of DNA molecules. A negative CT value indicates that there are less copies of that particular gene compared to reference gene, and a positive CT value indicates that there are more copies of that particular gene compared to the reference gene.

Figure 4B:
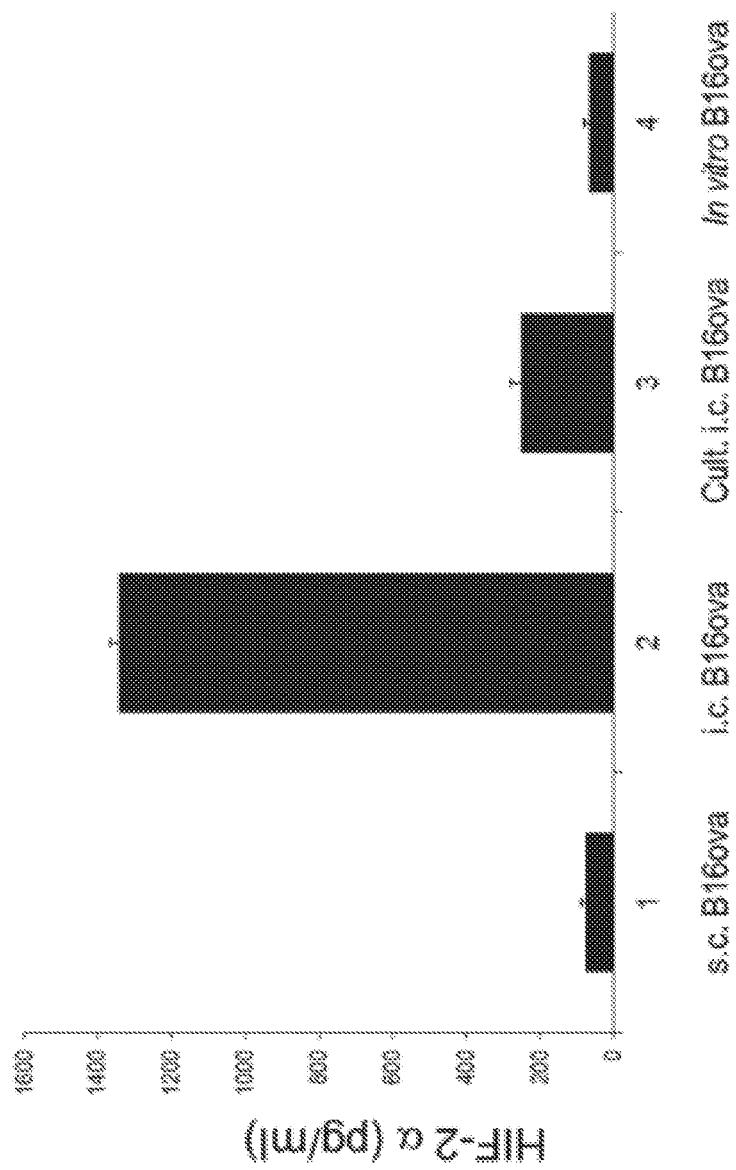

Consistent with the identification of N-RAS, CYT-C, and TYRP-1 as immunogens expressed by s.c. B16 tumors, freshly explanted s.c. B16 tumors had a very similar HIF-2α$^{Lo}$, c-myc$^{Lo}$ profile of antigen expression, and a slightly higher expression of both N-RAS and CYT-C mRNA (FIG. 4A). In contrast, and consistent with identification of HIF-2α and c-MYC as immunogens from the ASMEL used to treat i.c. tumors, freshly explanted B16 tumors from the brain had a very different HIF-2α$^{Hi}$, c-myc$^{Hi}$ profile as well as significantly lower levels of expression of N-RAS and CYT-C mRNAs (FIG. 4A). Expression levels of TYRP-1 were similar across B16 cells recovered from in vitro passage, s.c. or i.c sites. Expression of SOX-10 between i.c. and s.c. B16 tumor explants closely mirrored changes in HIF-2α. Finally, upon prolonged in vitro culture, B16 cells recovered from i.c. tumors gradually reverted from a HIF-2α$^{Hi}$, SOX-10$^{Hi}$, c-myc$^{Hi}$ profile to a more B16 in vitro/s.c.-like HIF-2α$^{Lo}$, SOX-10$^{lo}$, c-myc$^{Lo}$ profile with a gradual increase of N-RAS expression (FIG. 4A). The qrtPCR data was validated at the protein expression level for HIF-2α using an ELISA assay (FIG. 4B).

Figure 4C:
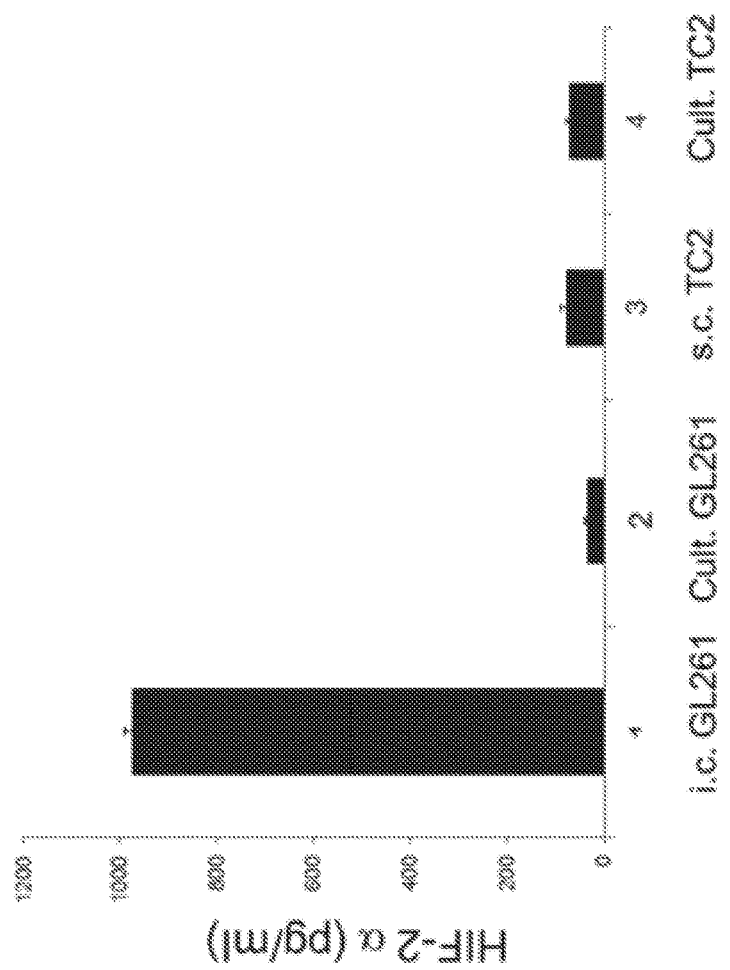

Freshly resected GL261 glioma cells also expressed a HIF-2α$^{Hi}$ phenotype at the level of protein expression, which was significantly different from the cultured cells from which those tumors were derived (FIG. 4C). In addition, as for s.c. B16 tumors, freshly resected s.c. TC2 prostate tumors had a very similar level of HIF-2α as their in vitro cultured counterparts (FIG. 4C).

Intra-Cranial CD11b+ Cells Mediate the HIF-2α$^{Hi}$ Phenotype

Figure 5A:
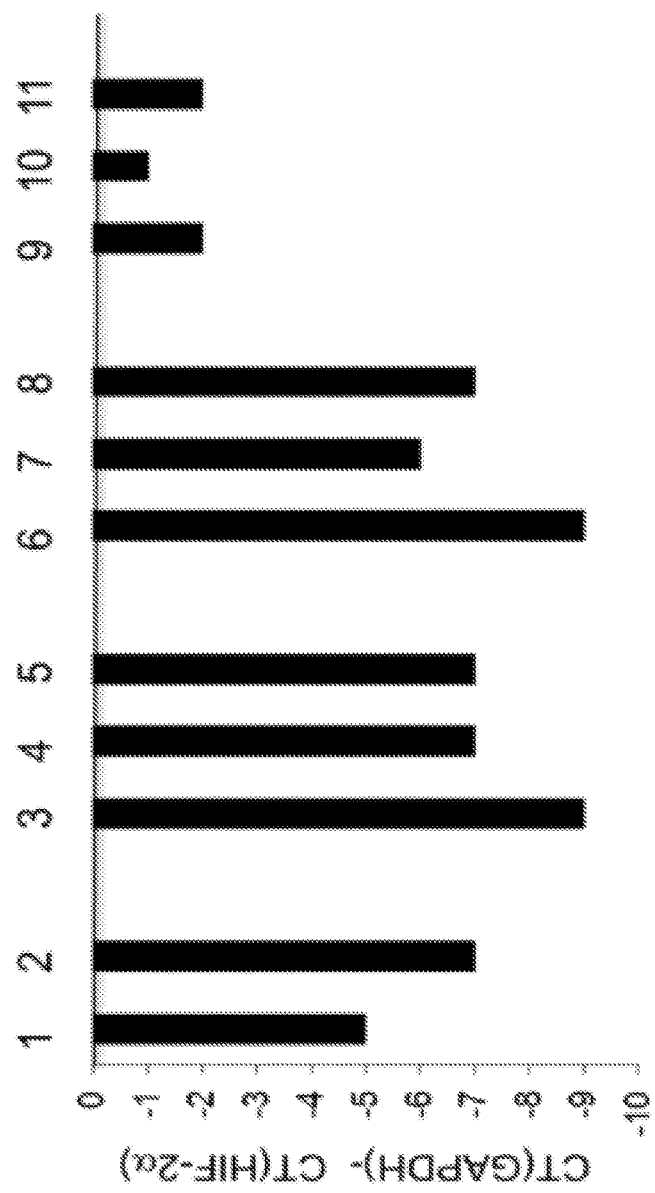
FIG. 5. The i.c. phenotype is imposed by brain associated immune cells. A. cDNA from two different brain cell suspensions (dissociated, intact brain cells) (Lanes 1 and 2); B16ova cells from three different freshly resected s.c. tumors (Lanes 3, 4, 5); co-cultures of B16ova cells from freshly resected s.c. tumors with freeze/thaw lysates of mouse brain cells (Lanes 6, 7, 8), or co-cultures of B16ova cells from freshly resected s.c. tumors with dissociated brain cell suspensions (Lanes 9, 10, 11) were screened by qRT-PCR for expression of HIF-2α relative to GAPDH. The difference in cycle threshold for expression of the control GAPDH gene and HIF-2α [CT(GAPDH)-CT(HIF-2α)] is shown. B. cDNA from B16ova cells from a freshly resected s.c. tumor with no added brain cell suspension (Lane 1); co-cultured with dissociated brain cell suspension (Lane 2); or co-cultured with dissociated brain cell suspensions depleted of CD8 (Lane 3); CD4 (Lane 4); NK (Lane 5); CD11b (Lane 6); Ly-6G+ neutrophils (using the IA8 depleting antibody) (Lane 7); or GR1+ cells (neutrophils, some DC, some monocytes, using the RB6-8C5 depleting antibody) (Lane 8); were screened by qRT-PCR for expression of HIF-2α relative to GAPDH. C. cDNA from B16ova cells from a freshly resected s.c. tumor were co-cultured with no added cells (Lane 1); with dissociated brain cell suspension (Lane 2); or with CD11b+ cells purified from spleens (Lane 3) or brains (Lane 4) of C57BL/6 mice were screened by qRT-PCR for expression of HIF-2α relative to GAPDH.
Figure 5B:
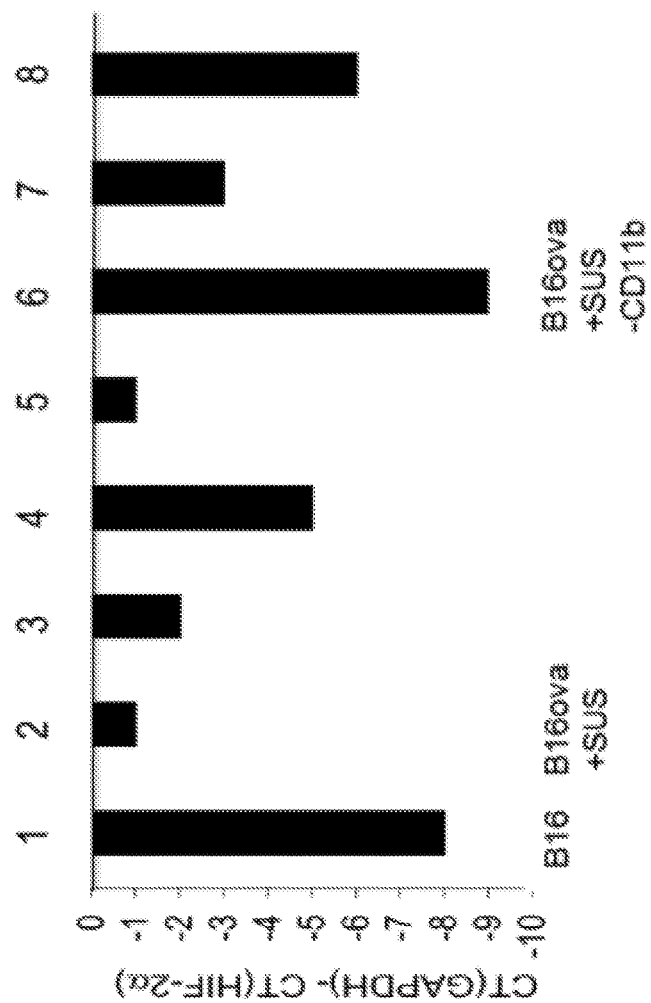
Figure 5C:
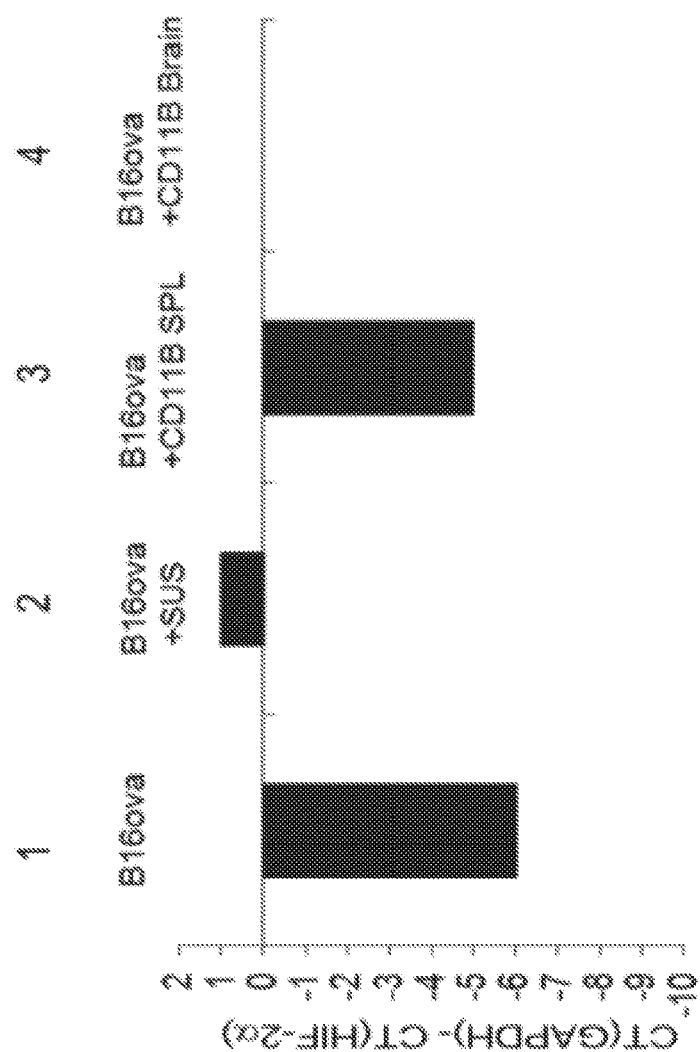

Next, the mechanisms by which the HIF-2α$^{Hi}$, SOX-10$^{Hi}$, c-myc$^{Hi}$, TYRP1, N-RAS$^{lo}$ CYT-C$^{lo}$ i.c. phenotype of i.c. B16 tumors was imposed upon the B16 cells by the in vivo environment in which the tumors were growing were investigated. In vitro culture of B16 cells with cell free lysates of mouse brain did not change the HIF-2α$^{lo}$ phenotype of cultured B16 cells (FIG. 5A, lanes 6-8). In contrast, co-culture with cell intact brain homogenates significantly increased levels of HIF-2α expression by qrtPCR (FIG. 5A, lanes 9-11), this was confirmed at the protein level by ELISA. Whilst depletion of neither CD8+ T cells, NK cells, nor neutrophils significantly prevented induction of the HIF-2α$^{Hi}$ phenotype by brain homogenates (FIG. 5B), depletion of CD11b+ cells completely abrogated the effects (FIG. 5B). Depletion of CD4+ T cells had a significant, but incomplete, effect on preventing the HIF-2α$^{lo}$ to HIF-2α$^{Hi}$ high transition (FIG. 5B). Finally, co-culture of B16 cells with purified CD11b+ cells from mouse brains was able to mimic almost entirely the effects of brain homogenates on inducing the HIF-2α$^{lo}$ to HIF-2α$^{Hi}$ transition of B16 cells in culture (FIG. 5C); an effect that was specific to brain derived CD11b+ cells as opposed to splenic CD11b+ cells (FIG. 5C).

i.c. Tumors are Treated by Different Immunogens than s.c. Tumors

Figure 6A:
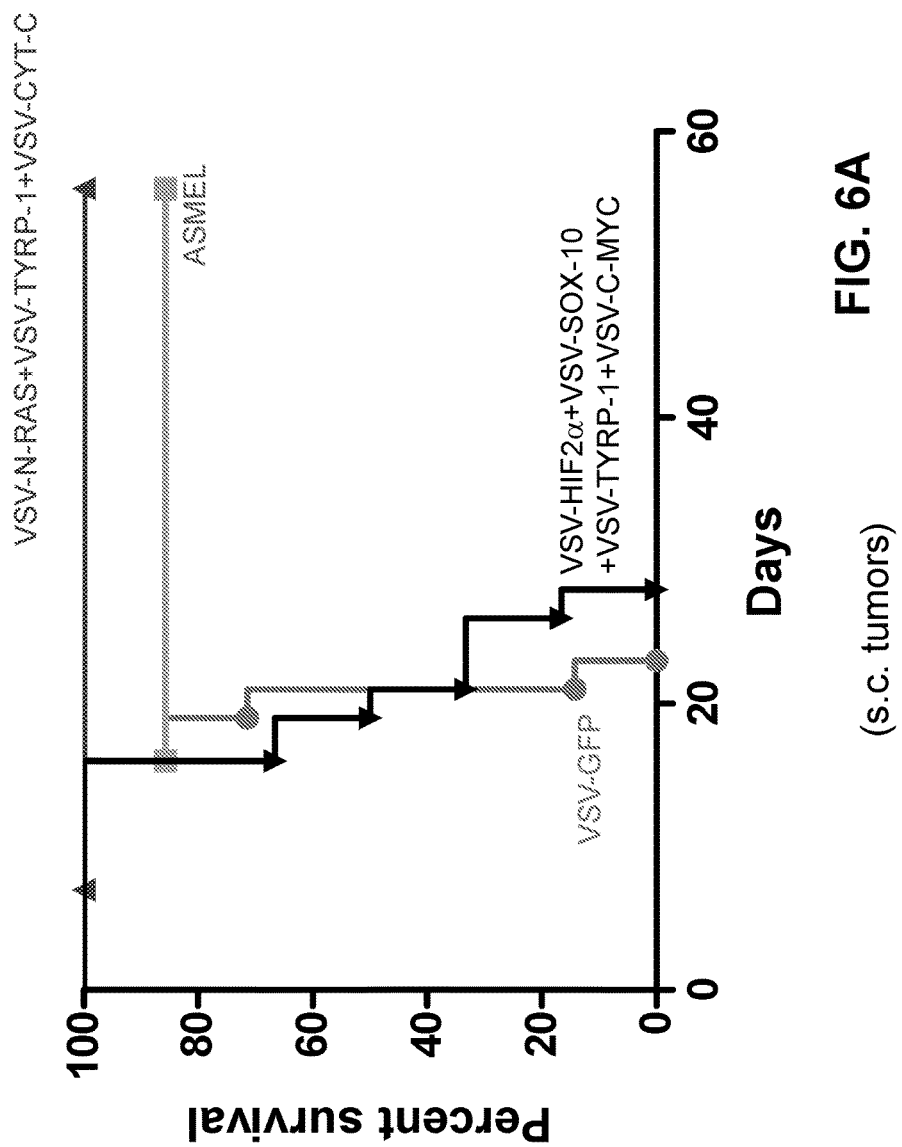
Figure 6B:
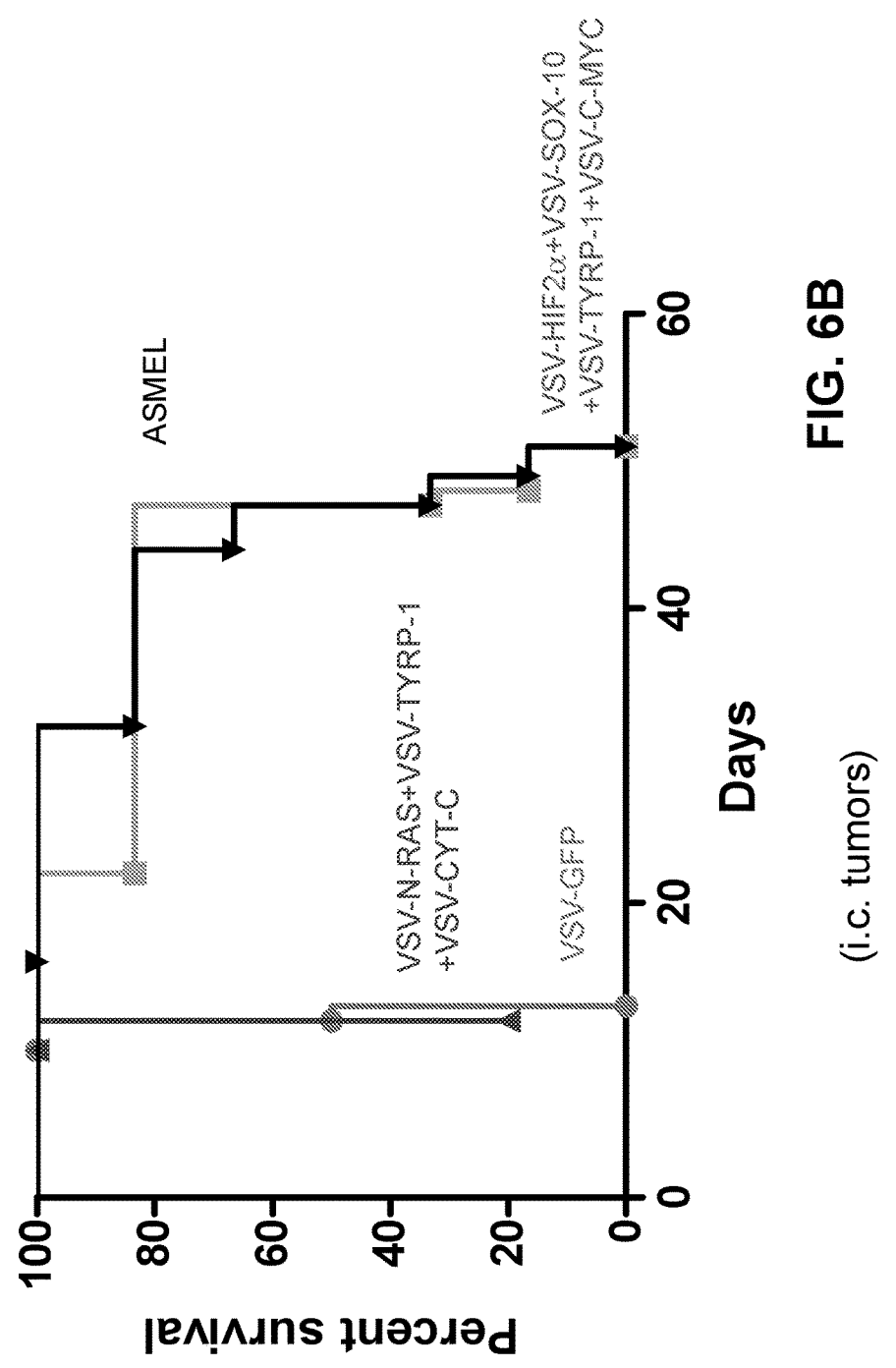

Experiments were performed to test whether the HIF-2α$^{Hi}$, SOX-10$^{Hi}$, c-myc$^{Hi}$, TYRP1, N-RAS$^{lo}$, CYT-C$^{lo}$ phenotype of i.c. B16ova tumors was the target of the T cell responses induced in vivo by systemic treatment with the ASMEL (FIG. 2A). Intravenous treatment of s.c. B16ova tumors with a combination of VSV-expressing HIF-2α, SOX-10, c-myc, and TYRP1 was completely ineffective at controlling tumor growth or overall survival (FIG. 6A). However, a combination of VSV expressing N-RAS, CYT-C, and TYRP-1 was very effective at treating s.c. B16ova tumors (p<0.001 compared to controls; FIG. 6A). For mice bearing i.c. B16ova tumors, the converse was true. While a combination of VSV expressing N-RAS, CYT-C, and TYRP-1 had no significant therapeutic effect on survival, the combination of VSV expressing HIF-2α, SOX-10, c-myc, and TYRP1 generated highly significant survival benefits over controls (P<0.0001) (FIG. 6B), which were similar to those produced by the intact ASMEL (FIG. 2A). The combination of (VSV-HIF-2α+VSV-TRP-1) had a significant, but very modest, benefit on survival compared to controls (p=0.02) in one experiment, while VSV-c-MYC+VSV-TYRP-1 was no better than controls in treating i.c. B16ova tumors. These results demonstrate that multiple combinations of immunogens are optimal for VSV-mediated immunotherapy of B16.

Additional T Cell Stimulation Improves Therapy and Lowers the Dose of Virus

Figure 7A:
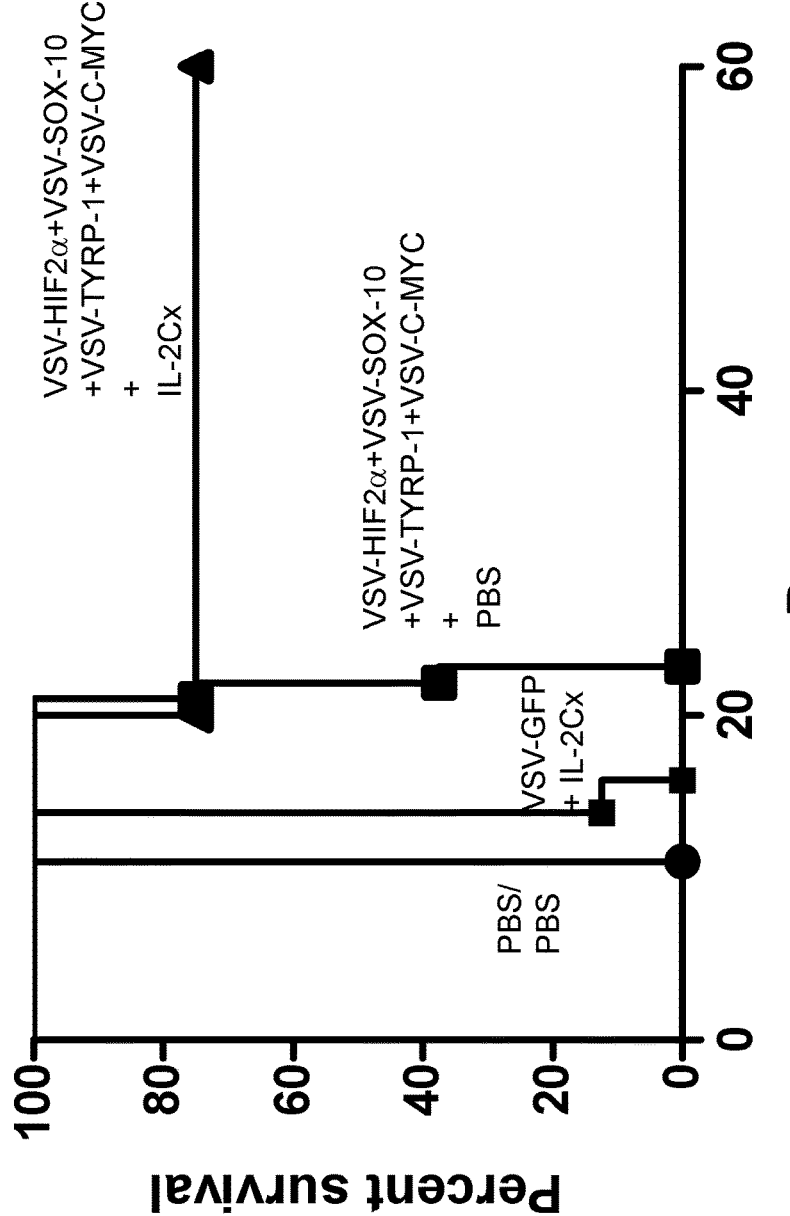
Figure 7B:
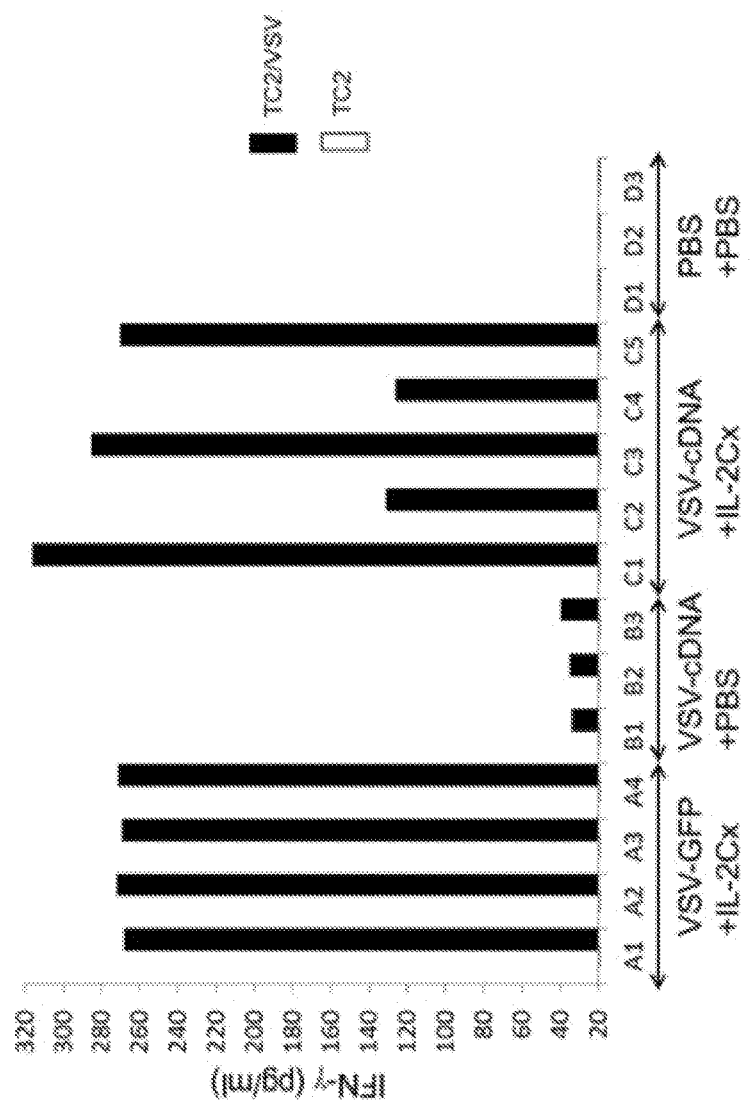
Figure 7D:
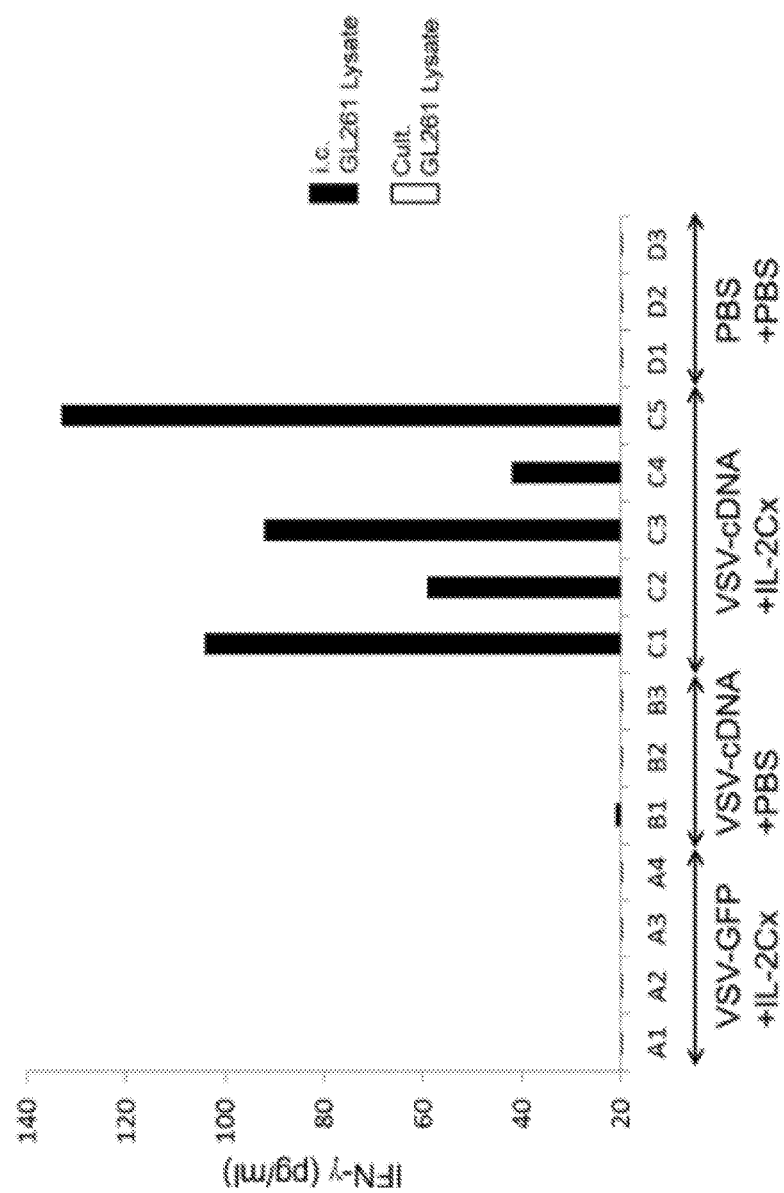

Because mice treated with the ASMEL, or combination of VSV expressing HIF-2α, SOX-10, c-myc, and TYRP1 eventually succumbed to tumor growth despite 12 injections (FIG. 6B), the ability to improve anti-tumor efficacy by supplying additional T cell stimulation along with the VSVcDNA antigenic stimulus was tested. A reduced number of i.v. injections (6 instead of 12 of FIG. 6B) of the combination of either the unfractionated ASMEL, or of VSV expressing HIF-2α, SOX-10, c-myc, and TYRP1, resulted in significant (p<0.01 compared to controls), but very moderate, survival benefits (FIG. 7A). In the presence of additional T cell stimulation with IL-2 immune complexes (IL-2 Cx; Cho et al., Cancer Res., 72:1986-95 (2012)), this dose of VSV-cDNA was converted into a highly effective immunotherapy that cured over 75% of mice with i.c. B16 tumors (FIG. 7A). Splen/LN from mice treated with VSV (either VSV-GFP or VSV-cDNA) and IL-2 Cx had significantly enhanced memory recall responses against VSV (re-stimulation in vitro with a VSV-infected, non B16 cell line) (FIG. 7B). As before, (FIG. 3C), mice treated with the VSV-cDNA combination alone did not have a Th1 IFN-γ response against i.c. or s.c. derived B16 cell targets (FIG. 7C). However, treatment with VSV-cDNA (but not VSV-GFP) in the presence of IL-2 Cx, induced weak, but significant, Th1 responses in all five mice tested against re-stimulating targets from B16 i.c. tumor growth, but only one mouse had a detectable Th1 response against s.c. B16 tumor targets (FIG. 7C). Interestingly, although treatment with VSV-cDNA alone did not generate any reactivity against glioma GL261 cells freshly explanted from the brain, IL-2 Cx co-treatment uncovered IFN-γ recall responses of similar magnitude to those against i.c. B16 targets (FIG. 7D).

Figure 7E:
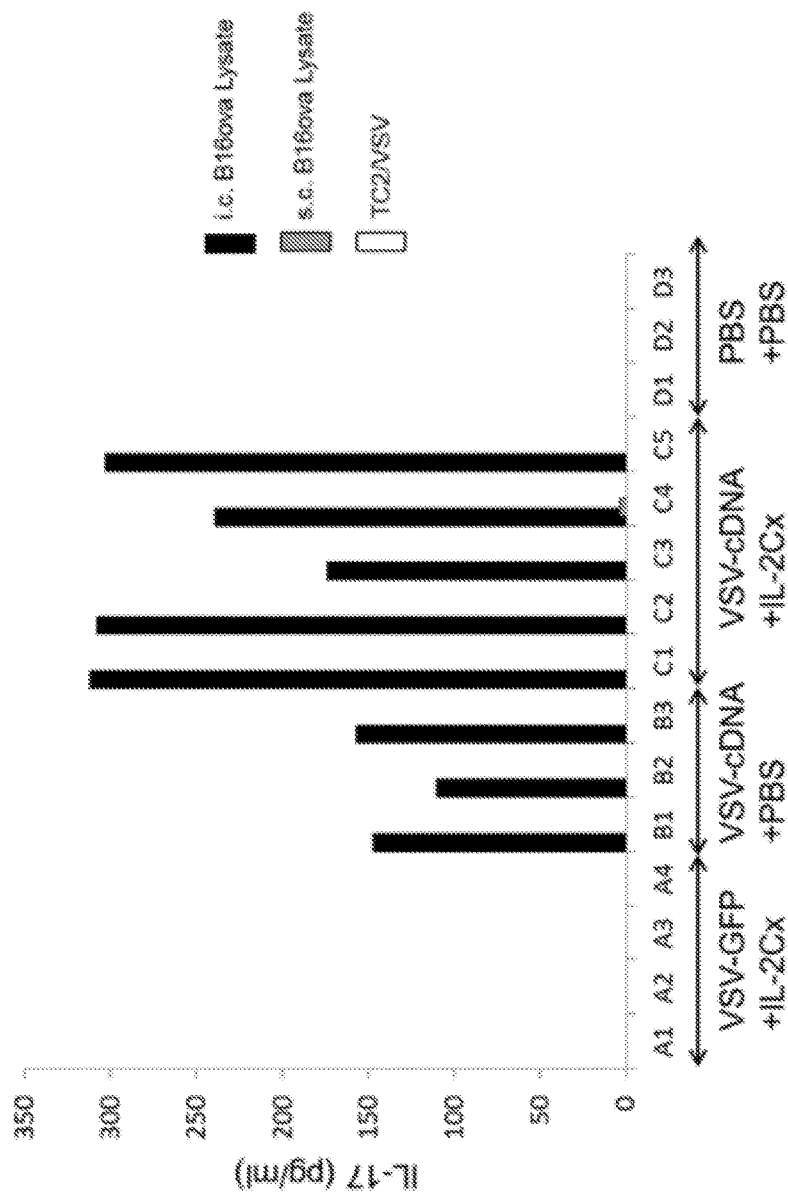
Figure 7F:
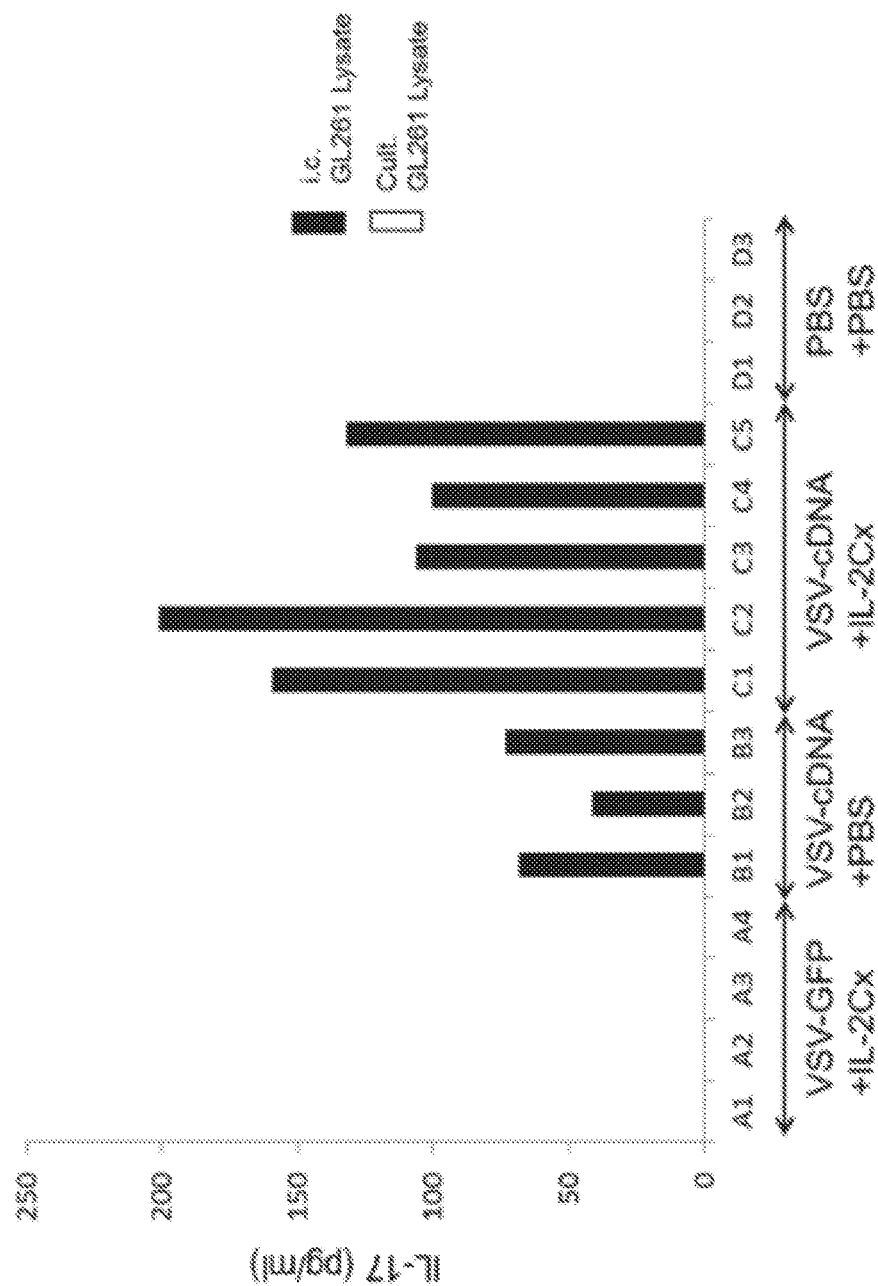
Figure 13A:
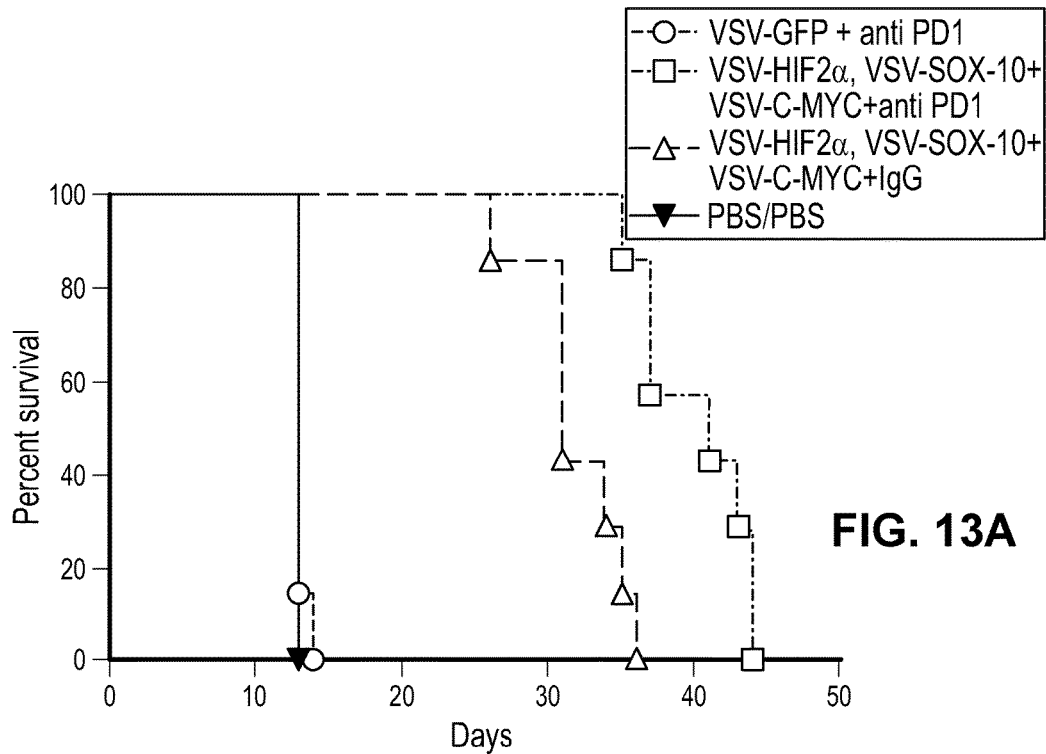
FIG. 13. Checkpoint inhibition uncovers a repressed anti-tumor Th1 IFN-γ response. A. C57BL/6 mice bearing 5 day established i.c. GL261 tumors were treated intravenously with a total of $5 \times 10^6$ pfu of (VSV-GFP); (VSV-HIF-2α, VSV-SOX-10, and VSV-c-MYC), or PBS on days 6, 8, 10, 13, 15, 17, 20, 22, and 24. On days 13, 15, 17, 20, 22, and 24, these groups were treated intravenously with either PBS, control IgG antibody, or anti-PD1 antibody at 10 mg/kg/mouse as shown. Survival with time is shown. B-D. Splenocytes and lymph nodes were pooled from 3 C57BL/6 mice per group bearing 5 day established i.c. GL261 tumors treated with either (PBS/PBS); (VSV-GFP+anti-PD1 antibody); (VSV-HIF-2α, VSV-SOX-10, and VSV-c-MYC+
Figure 13B:
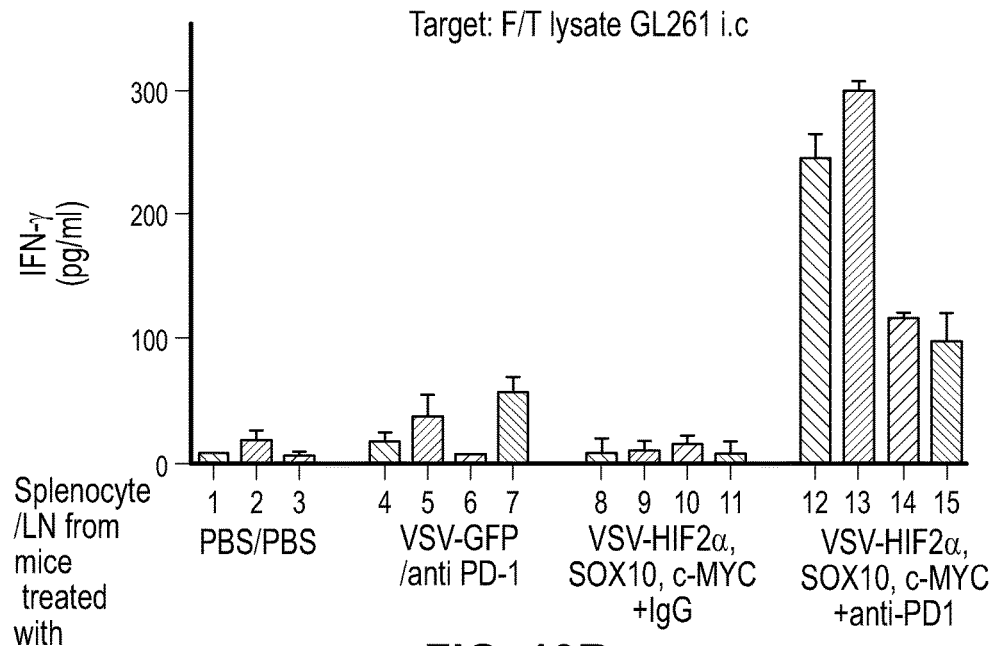
Figure 13C:
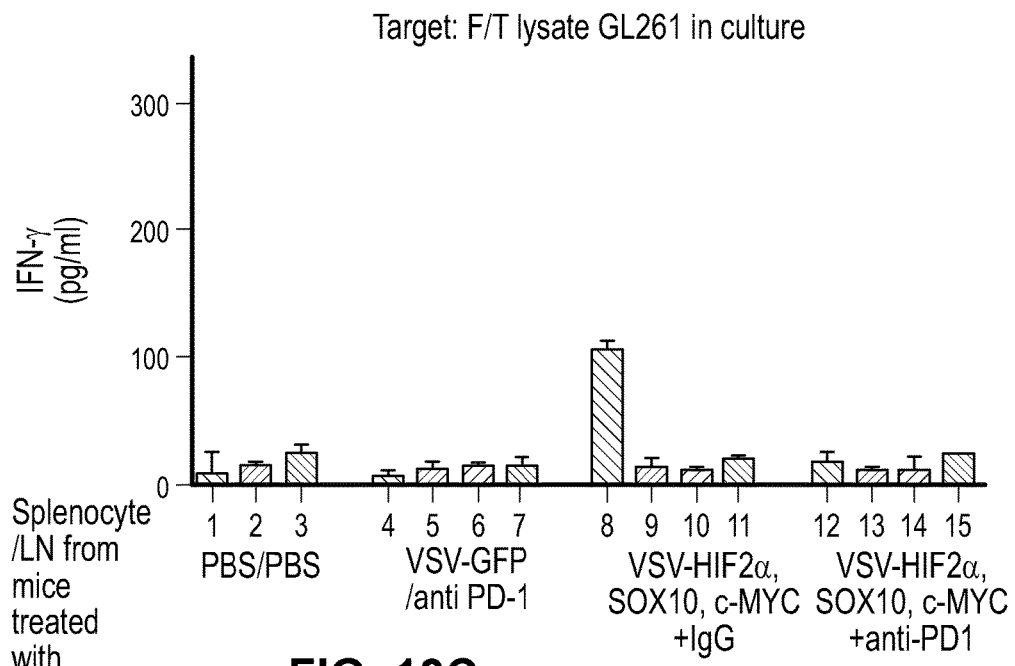
Figure 13D:
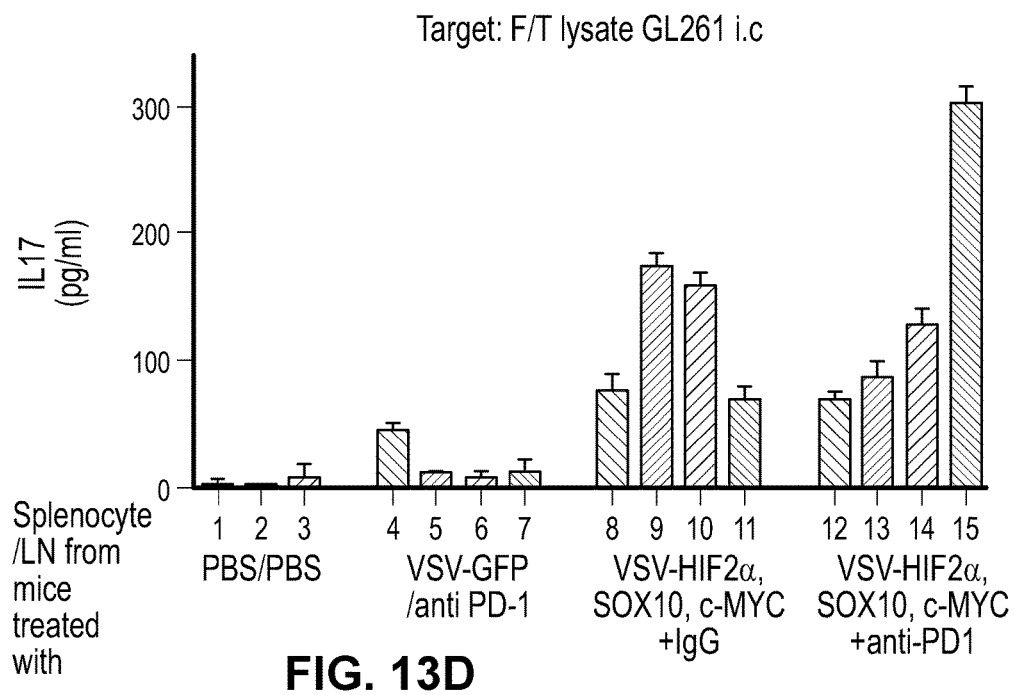
Figure 13E:
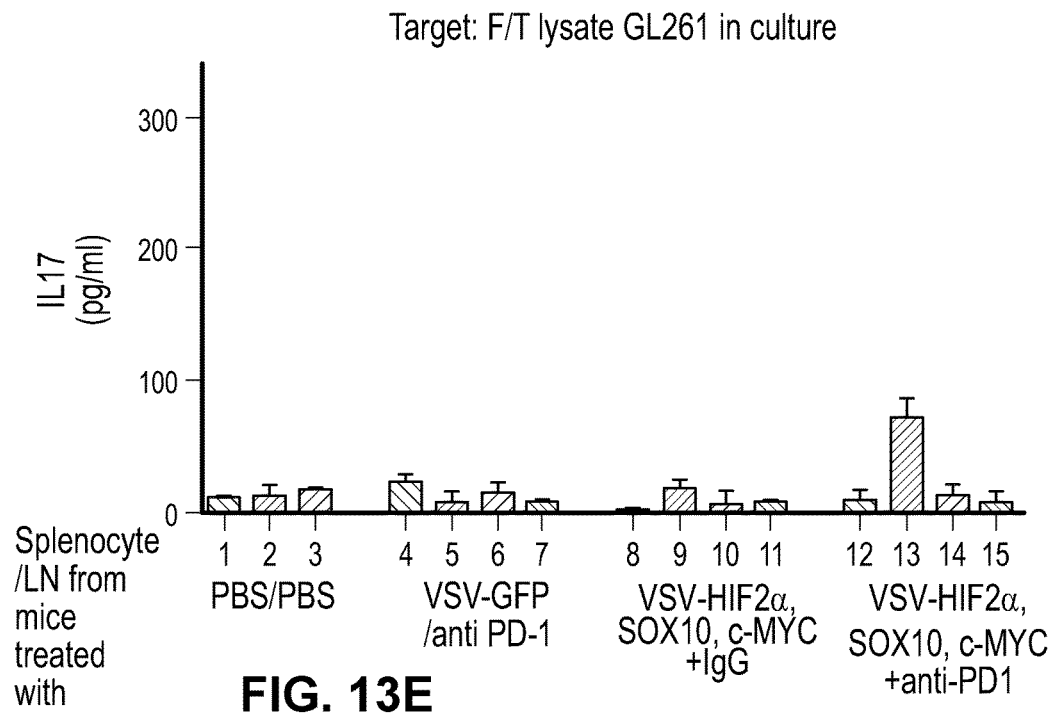
Figure 13F:
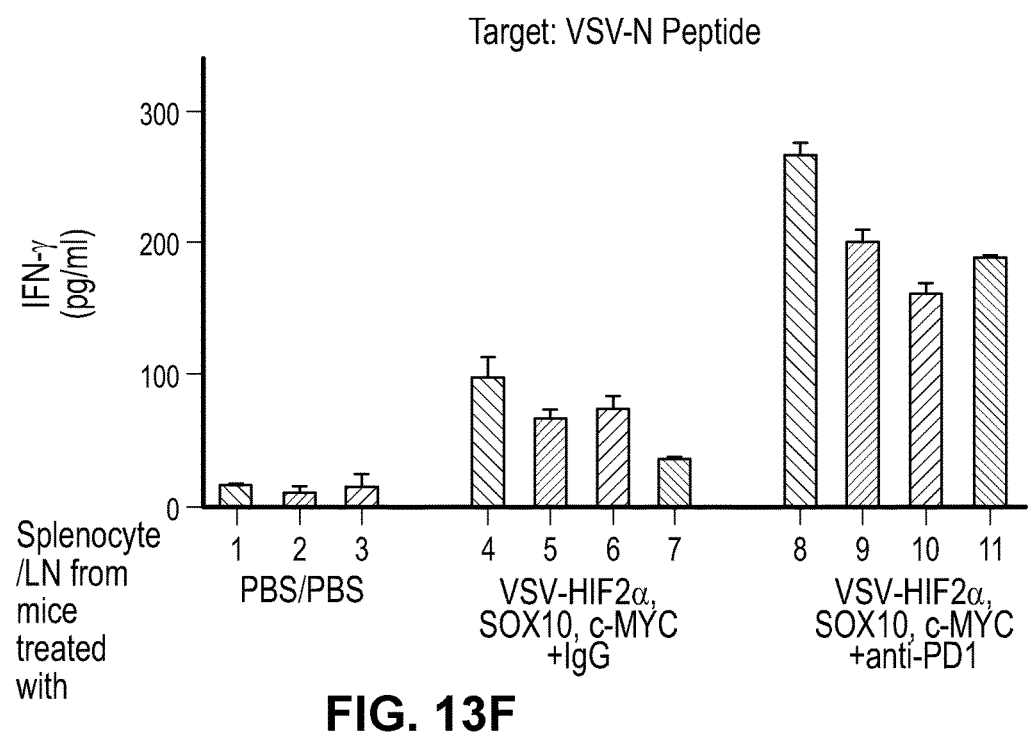

In addition, treatment with VSV-GFP or VSV-cDNA did not induce a Th17 response against the VSV with or without IL-2 Cx (FIG. 7E). However, the VSV-cDNA combination generated a strong Th17 response against i.c.-derived, but not s.c.-derived, B16, consistent with the results of FIG. 3A. Co-administration of IL-2 Cx significantly enhanced the magnitude of these Th17 responses against i.c.-derived B16 targets (FIG. 7E). Interestingly, although the Th1 responses induced by co-treatment of VSV-cDNA with IL-2Cx were of comparable magnitude against i.c. B16 and i.c. GL261 targets (FIG. 7D), the Th17 responses against i.c. B16 targets were generally higher than those against i.c-derived GL261 glioma targets (FIGS. 7E and 13F). As for the B16 targets, Splen/LN from mice treated with VSV-cDNA, either with or without IL-2Cx, did not generate recall responses to GL261 cells maintained in culture (FIG. 7F).

VSV-cDNA libraries engineered to express a cDNA library from human melanoma tumor cells were very effective as a systemic therapy to treat subcutaneous (s.c.) murine B16 melanomas. In addition, three VSV-cDNA viruses (VSV-N-RAS+VSV-CYTC-C+VSV-TYRP-1) from the VSV-cDNA library where identified as having the ability, in combination, but not alone, to induce s.c. B16 tumor rejection by priming a Th17 anti-tumor response. The results provided herein demonstrate that intravenous treatment with a VSV-cDNA library is a highly effective treatment for established intra-cranial melanoma brain tumors. Surprisingly, the combination of immunogenic antigens identified from the ASMEL as being successful for treating s.c. B16 tumors (VSV-N-RAS+VSV-CYTC-C+VSV-TYRP-1) was ineffective against i.c. B16 brain tumors; while the combination of VSV-HIF-2α, VSV-SOX-10, VSV-C-MYC, and VSV-TYRP1 from the ASMEL was identified as being highly effective against i.c. B16 brain tumors, but had no efficacy against the same tumors growing subcutaneously. Correspondingly, i.c. B16 tumors expressed a HIF-2α$^{Hi}$, SOX-10$^{Hi}$, c-myc$^{Hi}$, TYRP1, N-RAS$^{lo}$ CYT-C$^{lo}$ antigen profile, which differed significantly from the HIF-2α$^{lo}$, SOX-10$^{lo}$, c-myc$^{lo}$, TYRP1, N-RAS$^{Hi}$ CYT-C$^{Hi}$ phenotype of s.c. B16 tumors, and which was imposed upon the tumor cells by CD11b+ cells of the local tumor microenvironment in the brain. By identifying these differences in expression of these particular polypeptides between the i.c. and s.c. sites of tumor growth, VSV-mediated antigen expression can be differentially used to treat either s.c. tumors (with, for example, VSV-N-RAS+VSV-CYT-C+VSV-TYRP-1) or i.c. tumors (with, for example, VSV-HIF-2α+VSV-SOX-10+VSV-C-MYC+VSV-TYRP-1), but not both. In addition, by supplying additional T cell co-stimulation along with VSV-cDNA treatment, long term treatments, cancer survival rates, and/or cures of mice with established i.c. tumors can be achieved. For example, about 75% of mice tested were cured. These results also demonstrate that the anatomical location of a tumor profoundly affects the profile of antigens/potential immunogens that it expresses. Therefore, therapies based upon profiling of tumor cells outside of the actual local tumor microenvironment that is being treated in the patient may target a set of proteins/antigens/immunogens with little relevance to the 'quasi species' of tumor that is actually being targeted. These findings have important implications for the design of tumor-type, but location-specific, therapies. In addition, they raise the possibility that it may also be feasible to design therapies that are specific for tumors across histological types, but growing in a common location.

Example 2—Use of Truncated cDNAs

The following was performed to determine if VSV expressing truncated cDNA are more immunogenic than VSV expressing the corresponding full length cDNA. Truncated cDNAs may lead to production of a poorly, or incompletely folded polypeptide equivalent of the full length native polypeptide. Such poorly folded polypeptides could lead to an increased presentation of the polypeptide by antigen presenting cells.

VSV expressing full length versions of the N-RAS, CYT-C, and TYRP-1 cDNA were compared to VSV expressing truncated versions of the same polypeptides as recovered from screening of a VSV-cDNA library (ASMEL). The full length VSV combinations were unable to stimulate a Th17 memory recall response from splenocyte/LN cells of mice that had been treated for B16 tumors by the ASMEL. In contrast, the VSV combination expressing the library recovered, truncated cDNA stimulated IL-17 from the splenocyte/LN.

Example 3—Combination Viroimmunotherapy with Checkpoint Inhibition to Treat Glioma Cell Lines Murine B16 cells (American Type Culture Collection, Manassas, Va.) were grown in Dulbecco's modified Eagle's medium (DMEM; Life Technologies, Carlsbad, Calif.) supplemented with 10% fetal calf serum (FCS; Life technologies) and L-glutamine (Life technologies). Murine GL261 cells (American Type Culture Collection, Manassas, Va.) were grown in DMEM supplemented with 10% FCS. TRAMP-C2 (TC2) cells, derived from a prostate tumor that arose in a TRAMP mouse, were characterized as described elsewhere (Kottke et al., Cancer Res., 67:11970-9 (2007)) and were routinely grown as tumors in C57BL/6 mice in an androgen-independent manner. The K1735 melanoma cell line (Chong et al., Hum. Gene Ther., 7:1771-9 (1996)) was derived from H-2k C3H/He mice.

Mice

C57BL/6 and C3H mice were purchased from The Jackson Laboratory (Bar Harbor, Me.) at 6-8 weeks of age.

Virus

The ASMEL VSV-cDNA library was generated as described elsewhere (Kottke et al., Nature Med., 2011:854-9 (2011); Pulido et al., Nat. Biotechnol., 30:337-43 (2012); and Alonso-Camino et al., Mol. Ther., 22:1936-48 (2014)). Individual viral clones (VSV expressing N-RAS, CYT-C, TYRP-1, HIF-2α, SOX-10, or c-MYC) were isolated by limiting dilution as described elsewhere (Pulido et al., Nat. Biotechnol., 30:337-43 (2012); and Alonso-Camino et al., Mol. Ther., 22:1936-48 (2014)). These were expanded in BHK cells and purified by sucrose gradient centrifugation. VSV-GFP was manufactured by cloning the cDNA for GFP into the plasmid pVSV-XN2 as described elsewhere (Fernandez et al., J. Virol., 76:895-904 (2002)). Monoclonal VSV-GFP was obtained by plaque purification on BHK-21 cells and concentrated by sucrose-gradient centrifugation.

Measurement of HIF-2α Polypeptide in i.c. Explants and In Vitro Cultures

To establish i.c. tumors, $1\times10^4$ cells in 2 µL PBS were stereotactically injected into the brain (1 mm anterior, and 2 mm lateral to the bregma) of C57Bl/6 (B16, GL261, or TC2 cells) or C3H (K1735 cells) mice. Mice were sacrificed upon sign of distress, and single-cell suspensions of brain tumor explants or in vitro cultured cells (B16, GL261, TC2 or K1735) were plated at $1\times10^5$ per well in DMEM+10% FCS and 1% penicillin-streptomycin. Cell-free supernatants were harvested, and HIF-2α polypeptide expression was measured by ELISA according to the manufacturer's instructions (USCN Life Sciences, Houston Tex.). $1\times10^5$ cells of each cell line (B16, GL261, TC2, K1735) from in vitro cultures also were plated and measured for HIF-2α polypeptide expression.

Measurement of HIF-2α Polypeptide in Co-Cultures of GL261 and Splenic/Brain-Derived CD11b+ Cells CD11b+ cells were purified from brain-cell suspensions of multiple brains, or from the spleens of C57Bl/6 mice (re-suspended in Iscove's modified Dulbecco's medium (IMDM; Gibco, Grand Island, N.Y.)+5% FCS+1% penicillin-streptomycin+40 µmol/12-ME) using CD11b microbeads according to the manufacturer's instructions (Miltenyi Biotech, Auburn, Calif.). $1\times10^6$ CD11b+ cells were co-cultured in DMEM+10% FCS and 1% penicillin-streptomycin with ($1\times10^5$) GL261 cells. After 24 hours of co-culture, cell-free supernatants were harvested, and HIF-2α polypeptide levels were measured by ELISA. HIF-2α polypeptide also was evaluated following co-culture of GL261 cells with brain- or spleen-derived CD11b+ cells, in the presence of 10 ng/mL recombinant TGF-β RII Fc Chimera 341-BR (R&D systems, MN).

Human Tumor Explants

Human primary glioblastoma brain tumor tissue was obtained following surgery. Within three hours of surgical resection, explants were depleted of CD11b+ cells using CD11b microbeads. Tumor cells were then seeded at $1\times10^4$ cells per well in DMEM+10% FCS+1% penicillin-streptomycin±isolated autologous CD11b+ cells ($5\times10^3$ per well). HIF-2α polypeptide levels in cell-free supernatants were evaluated at 24 hours and again following 2 week's culture. HIF-2α polypeptide also was evaluated in cell-free supernatants from $1\times10^3$ isolated CD11b+ cells, 24 hours after explant.

In Vivo Studies

To establish i.c. tumors, $1\times10^4$ GL261 cells in 2 µL PBS were stereotactically injected using a syringe bearing a 26G needle into the brain (1 mm anterior, and 2 mm lateral to the bregma) of C57BL/6 mice (7-9 mice per treatment group unless otherwise stated). Virus, drug, or PBS control (100 µL) was administered intravenously following 5 days tumor establishment and occurred as dictated by each specific study. Mice were examined daily for overall health and, survival with time was documented.

For the therapeutic study evaluating the effect of anti-PD1 antibody in combination with virus treatment, control ChromPure rat IgG antibody (Jackson Immunochemicals, West Grove, Pa.) or anti-PD1 antibody were injected intravenously at 225 µg/mouse/injection (Clone RMP 1-14, Bioxcell West Lebanon, N.H.). For therapy evaluating the use of two checkpoint inhibitors, intravenous anti-PD1 was administered at 225 µg/mouse/injection and anti-CTLA4 at 0.1 mg/mouse/injection (Bioxcell West Lebanon, N.H.).

In Vitro Splenic/Lymph Node T-Cell Reactivation and ELISA for IFN-γ/IL-17

Spleens and lymph nodes were harvested from euthanized mice and dissociated into single-cell suspensions by crushing through a 100 µm filter. Red blood cells were lysed with ACK lysis buffer (sterile distilled $H_2O$ containing 0.15 M $NH_4Cl$, 1.0 mM $KHCO_3$ and 0.1 mM EDTA adjusted to pH 7.2-7.4) for 2 minutes. Cells were re-suspended at $1\times10^6$ cells/mL in IMDM+5% FCS+1% penicillin-streptomycin+ 40 µmol/l 2-ME. Pooled cells ($1\times10^6$ per well) were stimulated with freeze thaw lysates (equivalent to $1\times10^5$ cells) of either GL261 tumors recovered from mice bearing i.c. GL261 tumors or in vitro cultured GL261 cells, every 24 hours for 3 days. Following 48 hours of culture, cell-free supernatants were collected and assayed by ELISA for IFN-γ (BD Biosciences, San Jose, Calif.) or IL-17 (R&D systems, Minneapolis, Minn.). Re-stimulation also was carried out with splenocytes and lymph node cells depleted of Treg cells using Miltenyi CD4+/CD25+ beads (Miltenyi Biotech, Auburn, Calif.). Splenocyte and lymph node single cell isolates also were stimulated as described herein with the VSV-N protein derived epitope peptide (VSV-N52-59: RGYVYQG at 5 µg/mL) (synthesized at a core facility) and supernatants were evaluated for IFN-γ and IL-17 response by ELISA.

Statistics

Survival data from animal experiments were analyzed using the log rank test with Graph Pad Prism 6 (Graph Pad software, La Jolla, Calif.). A two-sample, unequal variance Students t-test was used to evaluate in vitro data. Statistical significance was determined at the level of $P<0.05$.

Results

Figure 9:
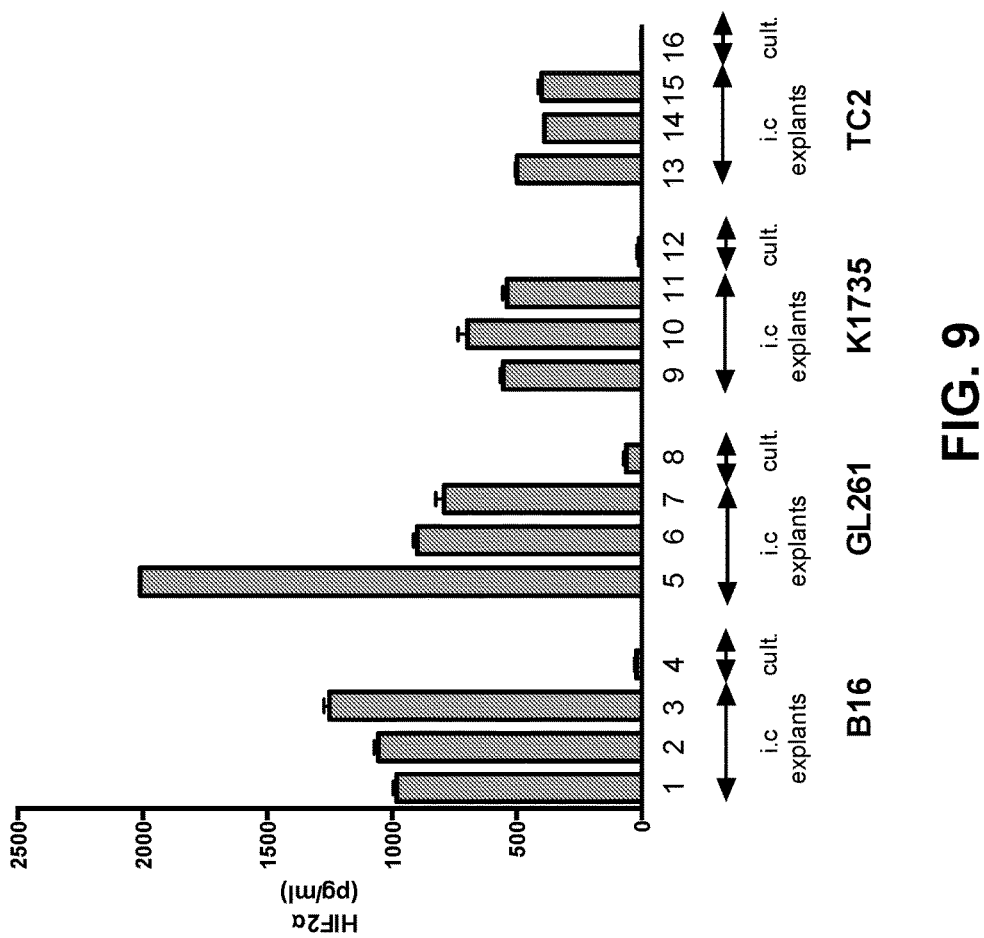
FIG. 9. Intracranial tumors of different histology express a HIF-2αHi phenotype. Tumors established in the brains of C57BL/6 (B16, GL261 or TC2 cells) or C3H (K1735) mice were dissected upon sacrifice (tumor explants), and tumor cells were seeded at $1 \times 10^5$ per well. $1 \times 10^5$ cells of each cell line cultured in vitro (cult.) were also plated. HIF-2α was measured by ELISA after 24 hours. Error bars are expressed as standard deviation (SD).

Intra-cranial tumors of different histologies express a similar HIF-2αHi phenotype. It was hypothesized that the intra-cranial microenvironment imposes a HIF-2αHi phenotype upon different types of tumors, which is distinct from that expressed by the same tumor cells growing in culture. Consistent with this hypothesis, freshly resected i.c. tumors of different histological types, including K1735 melanoma (in C3H mice), as well as B16 melanoma, GL261 glioma, and TC2 prostate cancer (C57Bl/6 mice), all expressed a HIF-2αHi phenotype. In contrast, the same cell lines grown in culture, from which the tumors were initially derived by i.c. implantation, expressed low or undetectable levels of HIF-2α (FIG. 9).

Figure 10:
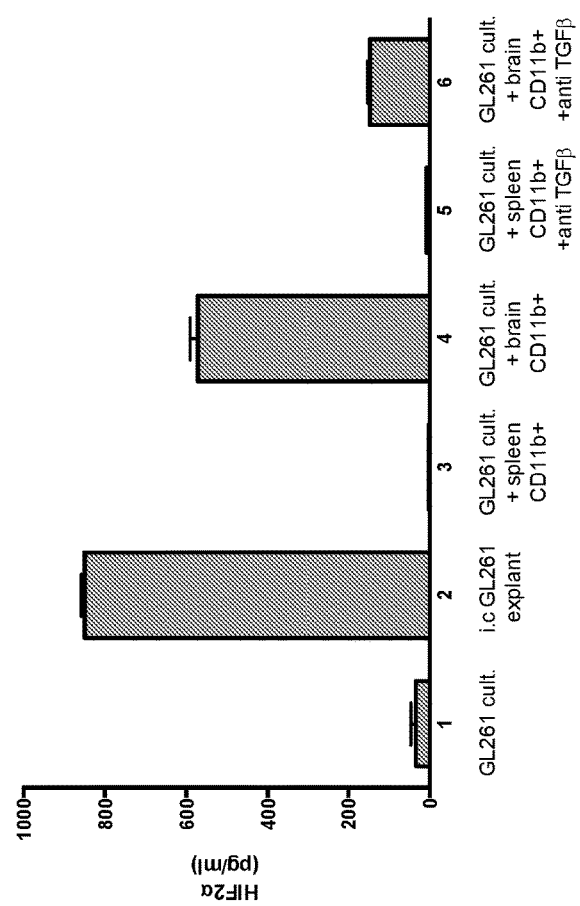
FIG. 10. Brain derived CD11b+ cells impose a HIF-2αHi phenotype on in vitro cultured GL261, in part through TGF-β. HIF-2α expression was measured by ELISA from: $1 \times 10^5$ GL261 cells cultured in vitro for 24 hours (lane 1); GL261 i.c. tumors, dissected from the brain upon sacrifice, and plated at $1 \times 10^5$ cells per well for 24 hours (lane 2); $1 \times 10^5$ GL261 cells co-cultured for 24 hours with $1 \times 10^6$ CD11b+ cells purified from normal splenocytes of C57Bl/6 mice (lane 3); $1 \times 10^5$ GL261 cells co-cultured for 24 hours with $1 \times 10^6$ CD11b+ cells purified from normal brains of C57Bl/6 mice (lane 4). Cultures of lanes 3 and 4 were repeated in the presence of recombinant TGF-β RII Fc chimera at 10 ng/mL (lane 5 and 6). Results are representative of three separate measurements. Error bars are expressed as standard deviation (SD).

CD11b+ cells in intact brain homogenate impose a HIF-2αHi phenotype on GL261 cells in vitro in part through TGF-β. The HIF-2αHi phenotype of i.c. B16-ova tumors was imposed by brain-associated, but not spleen-derived, CD11b+ cells. In vitro co-culture of GL261 cells with CD11b+ cells purified from intact brain homogenate, mediated a similar HIF-2αLo to HIF-2αHi phenotypic transition (FIG. 10). As for the B16 model, splenic CD11b+ cells were unable to impose a HIF-2αHi phenotype on in vitro cultured glioma cells (FIG. 10). Whilst neutralization of neither TNF-α, VEGF, nor interferon-γ prevented induction of the HIF-2αHi phenotype in GL261 and brain-associated CD11b+ cell co-cultures, blocking TGF-β significantly reduced HIF-2α expression (p=0.000173) (FIG. 10). These results demonstrate that CD11b+ cells of the brain microenvironment impose the HIF-2αHi phenotype upon tumors growing i.c., mediated, at least in part, through TGF-β.

Figure 11:
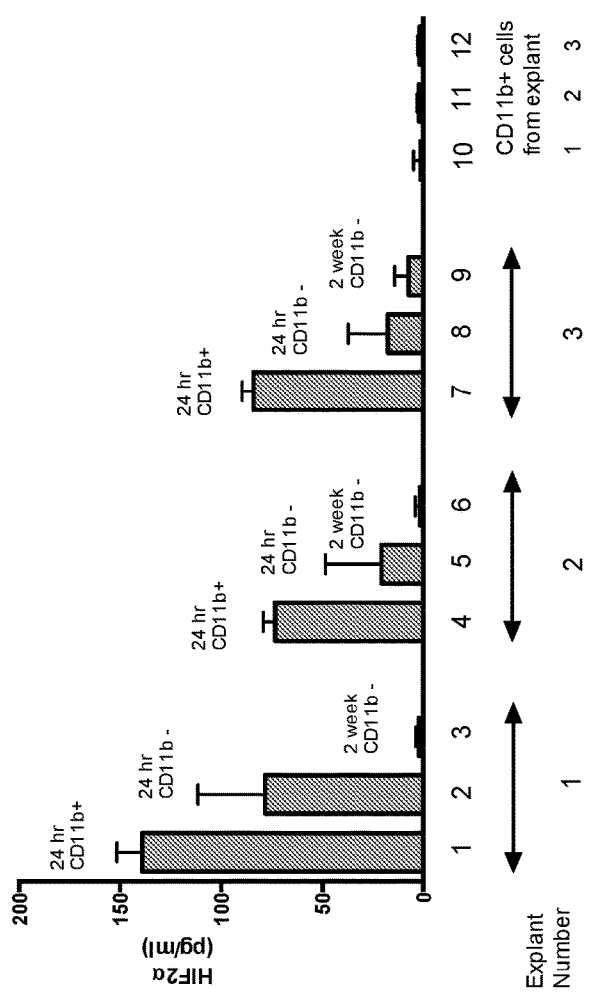
FIG. 11. Human brain tumor explants express a HIF-2αHi phenotype which diminishes with time. Human brain tumor explants were recovered from surgery and depleted of CD11b+ cells. Tumor cells were plated at $1 \times 10^4$ per well either alone (24 hours CD11b−) or with $5 \times 10^3$ CD11b+ cells (24 hours CD11b+). HIF-2α expression was measured at 24 hours. In cultures from which tumor cells survived more than a week, HIF-2α was measured from $1 \times 10^4$ tumor cells after 2 weeks, by which time CD11b+ cells had been washed away/died (2 week CD11b−). HIF-2α also was measured from $1 \times 10^3$ separated CD11b+ cells 24 hours after explant. Results are representative of three separate measurements. Error bars are expressed as standard deviation (SD).

Human tumor explants express a HIF-2αHi phenotype, which is reduced over time. To investigate how the murine model might reflect the patient situation, the HIF-2α phenotype of primary human brain tumor samples was studied. Freshly resected tumors cultured with their own autologous CD11b+ cells exhibited a HIF-2αHi phenotype, although levels of HIF-2α were consistently lower than in resected murine tumors (FIG. 11). Brain tumor explants depleted of CD11b+ cells expressed lower levels of HIF-2α after 24 hours of culture, although this did not reach statistical significance (p=0.101) (FIG. 11). The CD11b+ cells themselves did not express significant levels of HIF-2α (FIG. 11). After 2 weeks, CD11b+ cells within these co-cultures were lost, and the level of tumor cell associated HIF-2α was significantly reduced compared to levels seen at 24 hours post explant (p=0.017) (FIG. 11). Therefore, human brain tumors also express a HIF-2αHi phenotype, which is maintained, at least in part, by immune cells within the brain microenvironment.

Intracranial GL261 can be Treated with VSV-Tumor-Associated Antigen Therapy and Enhanced by Addition of Checkpoint Inhibitors Although mice bearing s.c. B16 tumors were treated successfully with a combination of VSV-expressed N-RAS, CYT-C, and TYRP-1, i.c. B16 tumors were only successfully treated with a combination of VSV expressed HIF-2α, SOX-10, c-MYC, and TYRP-1. The hypothesis that effective immunotherapy of an i.c. tumor of a different histological type could be targeted against this common i.c. tumor phenotype imposed by the brain microenvironment was tested further. Consistent with this, systemic delivery of VSV expressed HIF-2α, SOX-10, and c-MYC generated significant therapy over control treatment (p=0.0001) (FIG. 11). Although a combination of just two of the VSV-antigen gave significant therapy compared to control treatment (p=0.0001), optimal therapy required the combination of all three (HIF-2α, SOX-10, c-MYC) antigens ((VSV-HIF-2α/SOX-10/c-MYC) versus (VSV-HIF-2α/SOX-10+VSV-GFP) p=0.0414). Unlike in the B16 i.c. model, addition of the VSV-TYRP-1 virus gave no added therapeutic benefit to treatment with VSV-expressed HIF-2α, SOX-10, and c-MYC (data not shown). Consistent with our previous data with B16 i.c., as opposed to s.c. tumors, the combination of VSV expressed N-RAS, CYT-C and TYRP-1 was ineffective against i.c. GL261 tumors and offered no significant therapeutic advantage over control therapy (p=0.1432) (FIG. 11).

Figure 12:
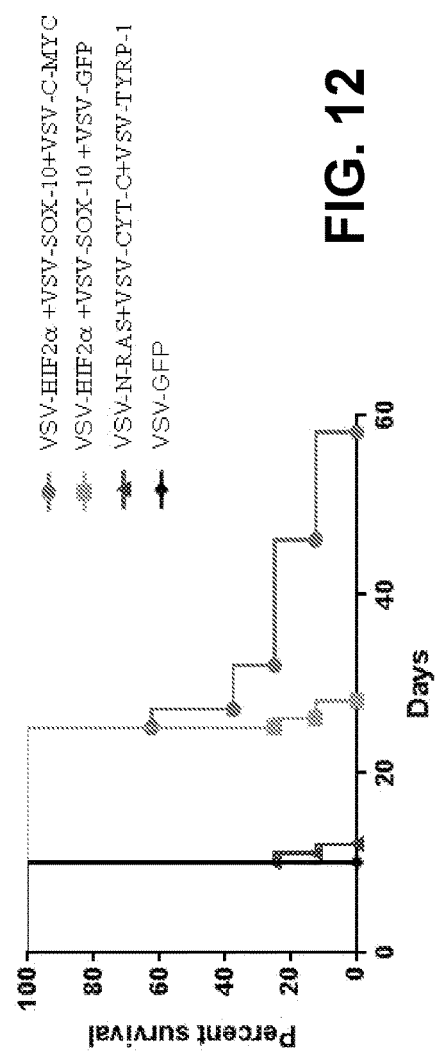
FIG. 12. VSV-TAA therapy of intracranial GL261 tumors. C57BL/6 mice bearing 5 day established i.c. GL261 tumors were treated intravenously with a total of $5 \times 10^6$ pfu of (VSV-HIF-2α, VSV-SOX-10, and VSV-c-MYC); (VSV-HIF-2α, VSV-SOX-10, and VSV-GFP); (VSV-N-RAS, VSV-CYT-C, and VSV-TYRP-1), or (VSV-GFP) on days 6, 8, 10, 13, 15, 17, 20, 22, 24, 27, 29, and 31. Survival with time is shown.

To investigate whether the viroimmunotherapy associated with VSV-antigen therapy of i.c. GL261 could be enhanced through combination with immune checkpoint inhibition, mice bearing i.c. GL261 tumors were treated with 9 (instead of the 12 of FIG. 12) systemic injections of VSV expressed HIF-2α, SOX-10, and c-MYC plus the checkpoint inhibitor antibody anti-PD1. Addition of anti-PD1 antibody significantly extended survival compared to the virus combination alone (p=0.0006) (FIG. 13A).

Taken together, these results demonstrate that the brain micro-environment-imposed antigenic signature of HIF-2α, SOX-10, and c-MYC can be immunologically targeted to treat i.c tumors of different histologies (glioma and melanoma) and that effective immunotherapy of tumors should take into account immunological profiles imposed upon tumors by their anatomical location.

Anti-PD-1 antibody uncovers a Th1 response against intra-cranial GL261. The therapeutic anti-tumor response to self antigens induced by VSV-cDNA library treatment is Th17 CD4+ T cell mediated and no Th1 IFN-γ T cell responses could be detected. Mixed splenocytes and lymph node cultures from mice bearing i.c. GL261 tumors following treatment with VSV-HIF-2α, VSV-SOX-10, and VSV-c-MYC did not secrete IFN-γ in response to challenge with freeze/thaw lysates of explanted i.c. GL261 tumors (FIG. 13B). In contrast, similar mixed cultures from mice treated with the same VSV-HIF-2α, VSV-SOX-10, and VSV-c-MYC plus anti-PD1 antibody, secreted significant levels of IFN-γ (p<0.05), suggesting that checkpoint inhibition through the PD1 axis uncovered a Th1 response to poorly immunogenic self antigens (FIG. 13B). Consistent with the distinct antigenic nature of GL261 cells growing in situ in the brain, compared to the same cells growing in culture (FIGS. 9 and 10), splenocyte and lymph node cultures from mice treated with VSV-HIF-2α/SOX-10/c-MYC+anti-PD1 did not secrete IFN-γ in response to challenge with freeze/thaw lysates derived from GL261 cells cultured in vitro (FIG. 13C). These results demonstrate that a Th1 response to a unique antigenic profile associated with i.c. GL261 tumors is generated following VSV-antigen viroimmunotherapy, but that it is suppressed in vivo and can be de-repressed upon checkpoint inhibition.

Anti-PD1 antibody therapy does not enhance the Th17 response against intra-cranial GL261. Interestingly, despite enhancing therapeutic efficacy in vivo (FIG. 13A), checkpoint inhibition with anti-PD1 did not significantly enhance the Th17 response generated by VSV-HIF-2α/SOX-10/c-MYC treatment (p=0.674) (against either i.c. explanted, or cultured, GL261 freeze thaw lysates), however, addition of anti-PD-1 enhanced a robust Th1, IFN-γ response (FIGS. 13D and 13E). A robust immune response of both Th1 IFN-γ, and Th17, anti-i.c. GL261 responses were only induced when VSV expressed tumor antigens: VSV-HIF-2α/SOX-10/c-MYC, as opposed to VSV-GFP, (FIGS. 13B and 13D, respectively), indicating that virally-mediated expression of tumor antigens was required for an effective immune response.

Anti-PD1 antibody enhances the Th1 response against VSV. VSV-HIF-2α/SOX-10/c-MYC treatment reproducibly induced a Th1 response against VSV antigens (FIG. 13F). This anti-VSV Th1 response also was significantly enhanced in mice treated with checkpoint inhibition compared with VSV-antigen treatment alone (p=0.00375) (FIG. 13F).

Taken together, these results demonstrate that combination of VSV-HIF-2α/SOX-10/c-MYC viroimmunotherapy with anti-PD1 checkpoint inhibition de-represses an anti-tumor Th1 IFN-γ T cell response against both self antigens and against foreign viral antigens, but has no significant effect on the anti-tumor Th17 response.

Anti-PD1 Checkpoint Inhibition Mimics Depletion of Treg

As before (FIG. 13B), the addition of anti-PD1 to VSV-HIF-2α/SOX-10/c-MYC therapy uncovered an anti-tumor Th1 response (lane 1 and 2 compared to 3 and 4, FIG. 14A). In vitro depletion of Treg from the mixed splenocyte/LN cultures prior to re-stimulation with freeze/thaw lysates also de-repressed the Th1 IFN-γ T cell response against i.c.

GL261, compared to Treg-intact cultures (lanes 1 and 2 compared to 5 and 6, FIG. 14A). However, Treg depletion from splenocyte/LN cultures of mice treated with VSV-HIF-2α/SOX-10/c-MYC+anti-PD1 did not further enhance the Th1 IFN-γ T cell response already uncovered by anti-PD1 therapy (lanes 3 and 4 compared to 7 and 8, FIG. 14A). Neither anti-PD1, nor in vitro Treg depletion, enhanced IL-17 responses generated by VSV-TAA therapy (FIG. 14B). These results demonstrate that anti-PD1 immune checkpoint inhibition may operate in vivo, to de-repress an anti-tumor Th1 IFN-γ T cell response and that this may be effected, at least in part, by affecting Treg function.

Combination Checkpoint Inhibition Further Improves VSV-Antigen Therapy

Figure 15A:
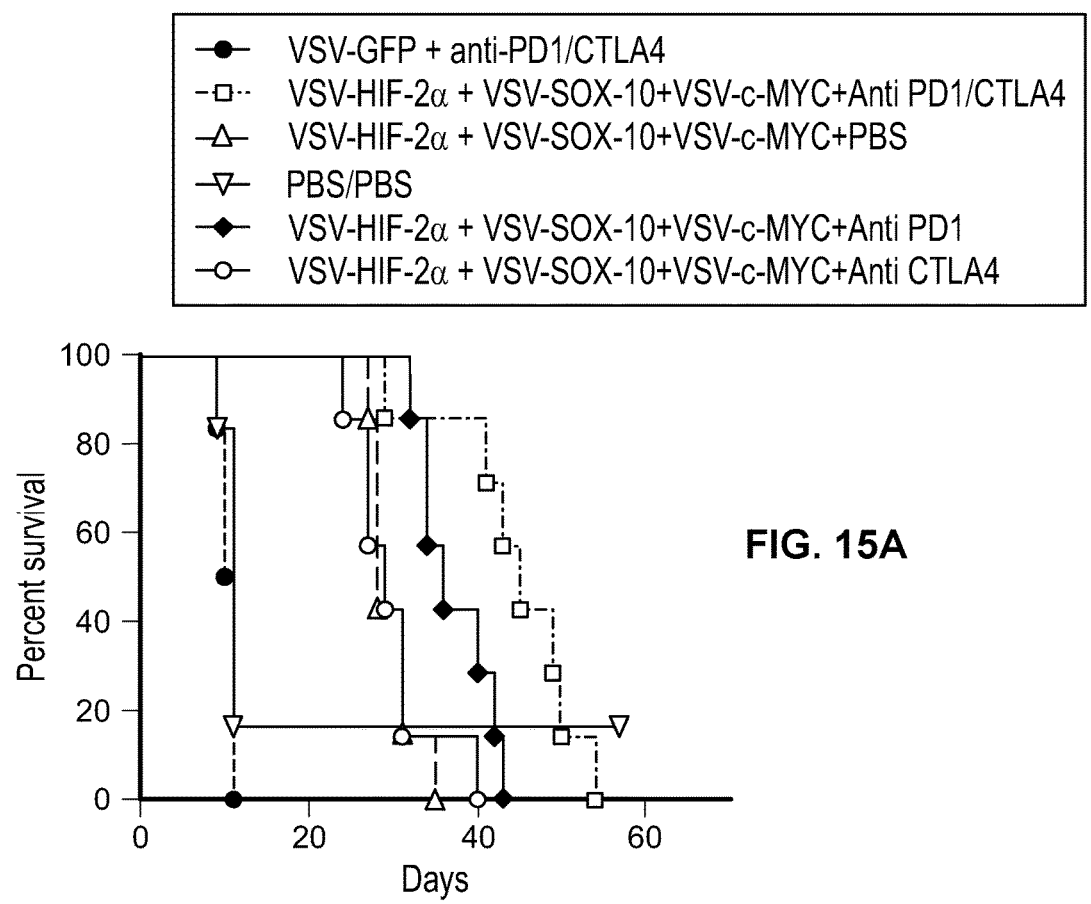

Given the success with enhancing VSV-antigen (e.g., VSV-HIF-2α/SOX-10/c-MYC) therapy with single checkpoint inhibitor therapy, a combination of anti-PD1 and anti-CTLA-4 checkpoint inhibition to target separate stages of the T cell activation/repression pathway was tested in combination with VSV-antigen (e.g., VSV-HIF-2α/SOX-10/c-MYC) therapy. As before, anti-PD1 treatment resulted in a significant improvement in survival in combination with VSV-HIF-2α/SOX-10/c-MYC therapy (FIG. 15A), in mice treated with a sub-optimal dose of 6 injections of VSV-VSV-HIF-2α/SOX-10/c-MYC (as opposed to the 12 of FIG. 12, and 9 of FIG. 13A). In contrast, anti-CTLA4 as a mono-supportive therapy for VSV-HIF-2α/SOX-10/c-MYC gave no added therapeutic benefit to VSV-HIF-2α/SOX-10/c-MYC alone (FIG. 15A). However, when used together, anti-PD1 and anti-CTLA4 significantly improved VSV-HIF-2α/SOX-10/c-MYC therapy alone (p=0.0015) and also was more effective than VSV-HIF-2α/SOX-10/c-MYC+anti-PD1 (p=0.0184) or anti-CTLA4 (p=0.0016) alone.

Figure 15B:
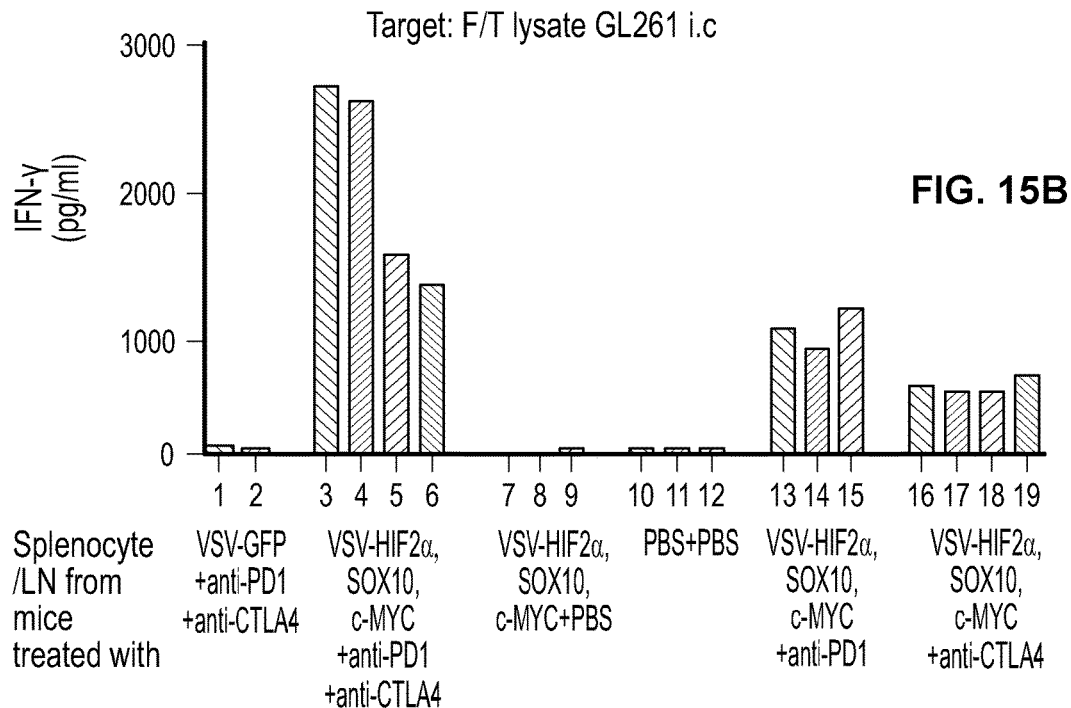
Figure 15C:
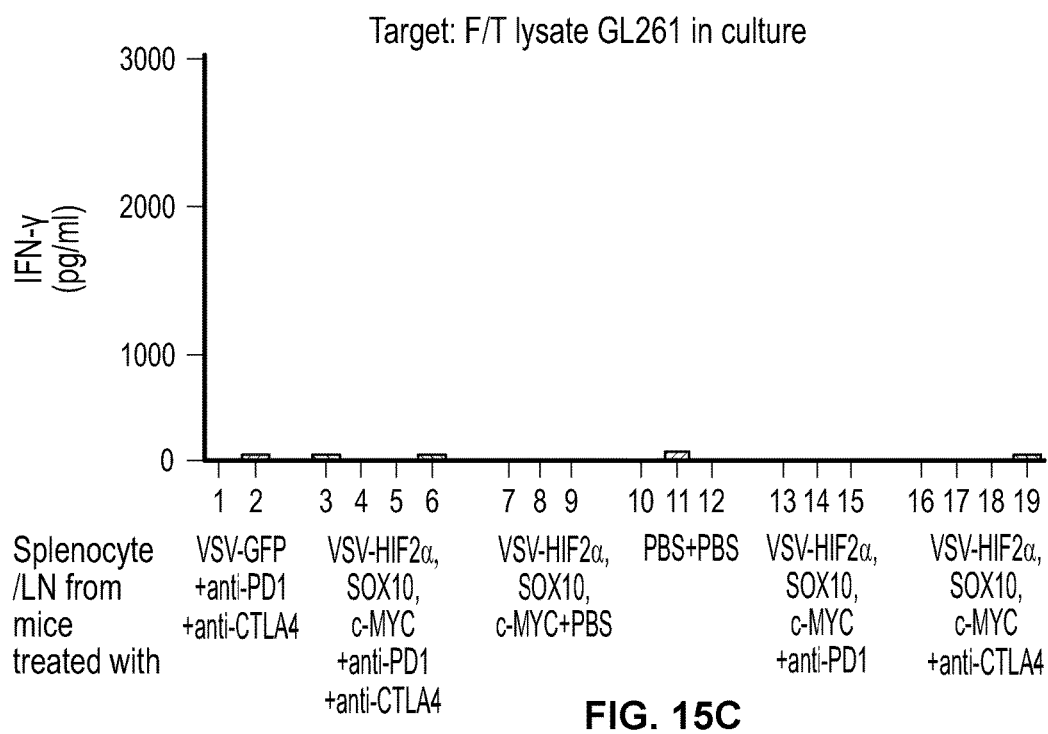

As before (FIG. 13), addition of anti-PD1 therapy to VSV-HIF-2α/SOX-10/c-MYC uncovered a Th1 IFN-γ T cell response to i.c. GL261 explants that was not detected from mice treated with VSV-HIF-2α/SOX-10/c-MYC alone (FIG. 15B). This also was true of anti-CTLA4 therapy in combination with VSV-HIF-2α/SOX-10/c-MYC, although to a lesser extent than with anti-PD1 (FIG. 15B). However, splenocyte/LN cultures from mice treated with VSV-HIF-2α/SOX-10/c-MYC and both anti-PD1 and anti-CTLA4 checkpoint inhibition displayed enhanced Th1 IFN-γ T cell response against i.c. GL261 compared to VSV-HIF-2α/SOX-10/c-MYC therapy in combination with either checkpoint inhibitor alone, although this only reached statistical significance when compared to the anti-CTLA4 treatment group (p=0.0282) (FIG. 15B).

Figure 15D:
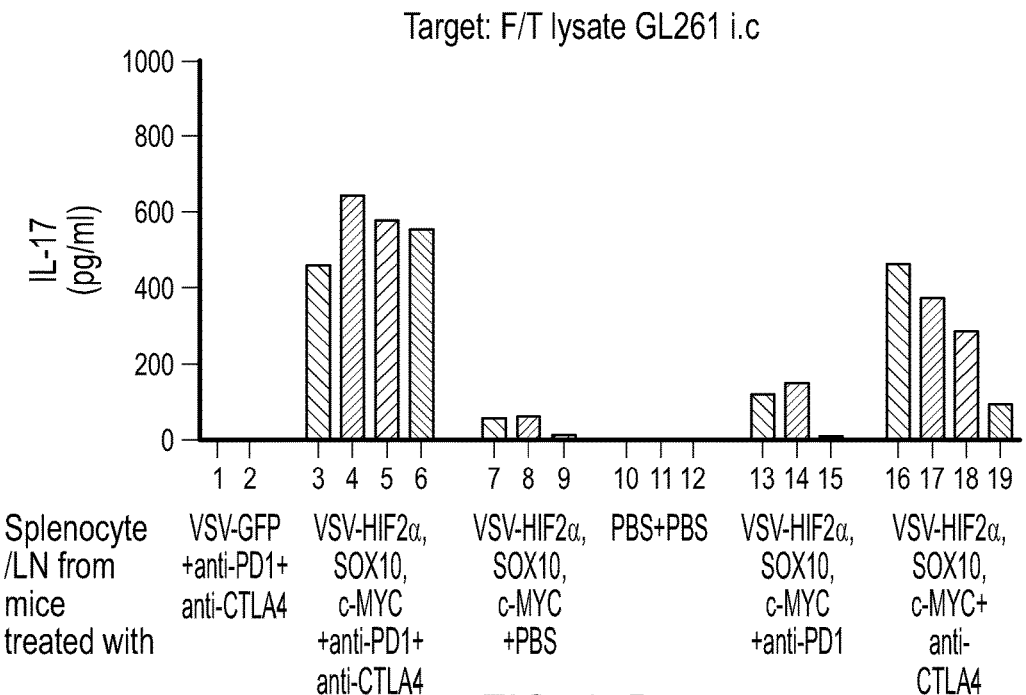
Figure 15E:
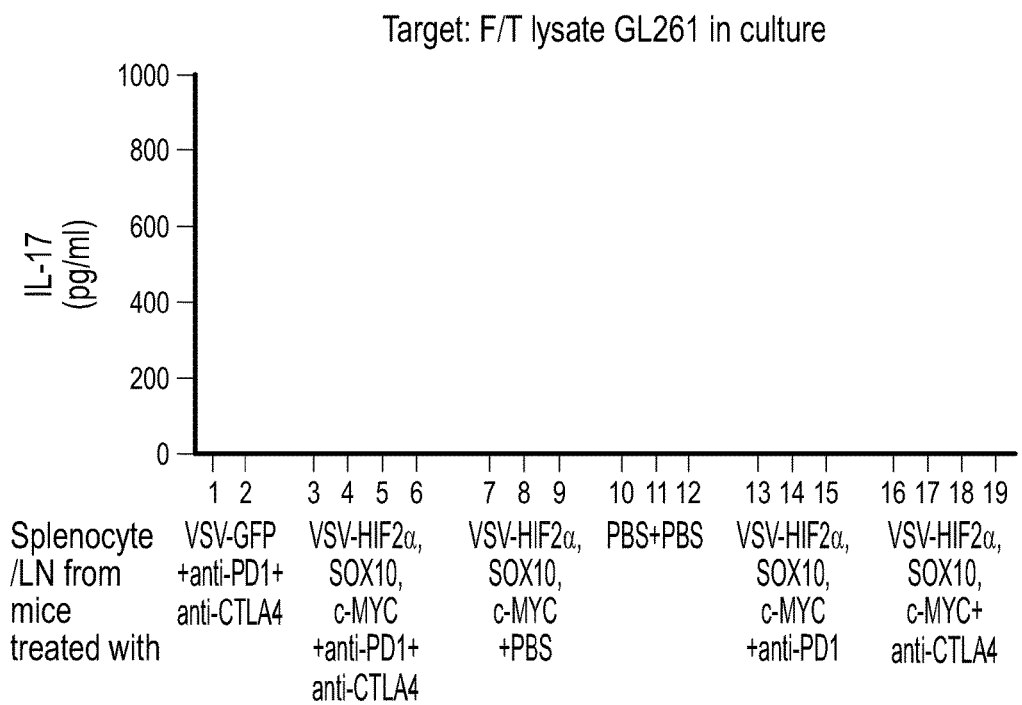

With respect to the Th-17 recall response, VSV-HIF-2α/SOX-10/c-MYC therapy in combination with anti-CTLA4 exhibited a strong trend to enhancing the Th17 response to i.c. GL261 responses (FIG. 15D) compared to VSV-HIF-2α/SOX-10/c-MYC therapy alone, or in combination with anti-PD1. Interestingly, splenocyte/LN cultures from mice treated with VSV-HIF-2α/SOX-10/c-MYC therapy combined with both anti-CTLA4 and anti-PD1 therapy generated the strongest Th17 recall responses against i.c GL261 (FIG. 15D).

Taken together, these results demonstrate that addition of checkpoint inhibitors, either singly or in combination, can enhance therapeutic responses to VSV-antigen (e.g., VSV-HIF-2α/SOX-10/c-MYC) treatment and that these increases in therapy are associated with the de-repression of an anti-tumor Th1 IFN-γ T cell response (anti-PD1, anti-CTLA4, or both) and of the anti-tumor Th17 response (anti-PD1 plus anti-CTLA4).

Example 3—Treating Melanoma Using VSV Vectors Designed to Express Truncated Antigens VSV vectors having nucleic acid that encodes truncated versions of antigens were recovered from the ASMEL cDNA library. The nucleic acids were sequenced to identify the location of the 3' truncations. For the truncated version of VSV-N-RAS, the VSV vector contained an N-RAS cDNA that encodes an N-RAS polypeptide lacking the following C-terminus: YRMKKLNSSDDGTQGCMGLP-CVVM (SEQ ID NO:1). See, also, FIG. 16. For the truncated version of VSV-CYT-C, the VSV vector contained a CYT-C cDNA that encodes a CYT-C polypeptide lacking the following C-terminus: YTIKRHKWSVLKSRKLAYR-PPK (SEQ ID NO:2). See, also, FIG. 17. For the truncated version of VSV-TYRP-1, the VSV vector contained a TYRP-1 cDNA that encodes a TYRP-1 polypeptide lacking the following C-terminus: YQCYAEEYEKLQNPNQSVV (SEQ ID NO:3). See, also, FIG. 18.

For the truncated version of VSV-TGF-β, the VSV vector contained a TGF-β cDNA that encodes a TGF-β polypeptide lacking the following C-terminus: YYVG-RKPKVEQLSN-MIVRSCKCS (SEQ ID NO:4). For the truncated version of VSV-KDR2, the VSV vector contained a KDR2 cDNA that encodes a KDR2 polypeptide lacking the following C-terminus: YSSEEAELLKLIEIGVQTGSTAQILQPDSGT-TLSSPPV (SEQ ID NO:5). For the truncated version of VSV-P-glycoprotein, the VSV vector contained a P-glycoprotein cDNA that encodes a P-glycoprotein polypeptide lacking the following C-terminus: YFSMVSVQAGTKRQ (SEQ ID NO:6).

C57BL/6 mice bearing 7 day established s.c. B16 tumors were treated i.v. with 9 doses of (1) VSV encoding library derived, truncated VSV-N-RAS+VSV-CYT-C+VSV TYRP-1 ($5 \times 10^6$ pfu/100 μL), (2) VSV encoding full length polypeptides: VSV-NRAS+VSV-TYRP-1+VSV-CYT-C, or (3) VSV-GFP. Survival of tumor-bearing C57BL/6 (n=8 mice per group) was determined. The results were representative of two separate experiments.

The combination of truncated cDNA for Cytochrome C (CYT-C), N-RAS, and TYRP-1 was more immunogenic against B16 tumors than the full length versions, when expressed from VSV (FIG. 17). The full Length VSV-cDNA combination improved survival of C57Bl/6 mice with s.c. B16 tumors, and the truncated virus combination appeared to cure the mice.

These results demonstrate that truncated antigens (e.g., antigens lacking a portion of their C terminus) can be used to treat cancer.

Example 4—Treating Cancer in Dogs

Dogs (e.g., 5-10 dogs) with a solitary intracranial mass consistent with a gliomas based on MRI that is surgically accessible are recruited. The diagnosis is confirmed as a high-grade (III-IV) glioma by histopathology. The dogs are otherwise in good health and able to undergo anesthesia for surgical excision and virus delivery.

The dogs are treated by surgical removal of the tumor and administration of either single VSV vectors (e.g., VSV-HIF-2α only) or a combination of different VSV vectors (e.g., VSV-HIF-2a+VSV-SOX-10+VSV-cMYC). For example, any particular combination of VSV vectors provided herein is administered to a dog having cancer. In some cases, a VSV-cDNA library such as an ASMEL is administered to a dog having cancer.

Toxicities are assessed using a standard veterinary scale of grade I-V events based on owner diaries, serial blood tests, and neurological examinations. Surgical resection of the tumor is performed using the appropriate approach based on MRI. Each dog is administered a standard drug regimen before craniotomy to minimize cerebral edema. After surgical debulking, each dog is administered $5 \times 10^8$ pfu of Reolysin (reovirus) injected in 5-4, aliquots around the resection cavity. A postoperative MRI is performed to assess the extent of resection, and then each dog is allowed to recover from anesthesia and is monitored in an intensive care unit. After surgery, each dog is administered prednisone (1 mg/kg body weight) PO every 12 hours for 2 days, and then the dose is tapered and discontinued over 7 days. Adjustments are made to the dose of steroids depending on the clinical signs, such as changes in mentation or neurological function (i.e., hemiparesis), of each individual dog. The dogs are examined by MRI of the brain performed immediately after surgery and then 4, 8, and 12 months after therapy. The scans are evaluated, and the surgical resection of the tumor is defined as gross total resection (GTR) if there is complete resection of the preoperative fluid-attenuated inversion recovery signal abnormality, near total resection (NTR) if a thin (<3 mm) residual fluid-attenuated inversion recovery signal abnormality remains around the rim of the resection cavity, or subtotal resection (STR) if there is residual nodular fluid-attenuated inversion recovery signal abnormality. The sequential MRI scans are evaluated for volume of tumor in individual dogs to measure response to treatment. Clinical response is considered as complete response (CR) if there is no evidence of the target lesion, partial response (PR) if the tumor is <25% of the original longest diameter of the tumor, progressive disease if there is >25% increase in the original longest diameter of the tumor, or stable disease (SD) if there are small changes that do not meet the previously defined criteria. If a dog develops recurrent or worsening neurologic signs before a scheduled MRI, an unscheduled MRI is performed at that time.

As the immunological boost, each dog is treated with intravenous injections of $5 \times 10^6$ pfu of VSV-TAA (e.g., a single VSV vector such as VSV-HIF-2α only or a combination of different VSV vectors such as VSV-HIF-2a+VSV-SOX-10+VSV-cMYC) on days 10, 30, 60, 90, 120, 150, 180, 210, 240, 270, 300, 330, and 360 after surgery, or until tumor recurrence. For example, any particular combination of VSV vectors provided herein is administered to a dog having cancer as an immunological boost. In some cases, a VSV-cDNA library such as an ASMEL is administered to a dog having cancer as an immunological boost.

Dogs are monitored for 30 minutes following each injection for any immediate adverse reactions, such as severe wheals, dyspnea, or other signs of anaphylaxis. Dogs suffering from an acute severe reaction are given dexamethasone (0.01 mg/kg SC) and diphenhydramine (0.5 mg/kg IM). Dogs are followed over a 12-month period by imaging or until euthanasia. Dogs are assessed with complete physical and neurological examinations and quality of life assessments at suture removal and each VSV-TAA injection.

Peripheral blood mononuclear cells (PBMC) are collected prior to surgery and on days 10, 60, 120, 180, 240, 300, and 360 after surgery to determine immunological response by re-stimulating the PBMC in vitro to measure T cell responses against autologous tumor cells by flow cytometry. In some cases, CTL assays and Western blots on serum are performed.

Example 5—Treating Cancer Using VSV Designed to Express IFN-β

VSV encoding TYRP-1 (full length) and IFN-β (VSV-mIFN-mTYRP-1) was generated by inserting mTYRP-1 in the vector backbone containing IFN-β (IFN-β) located between the M and G genes of VSV (FIG. 20). PCR amplification of mTYRP-1 cDNA was prepared from B16 cells using forward (5'-CTCGAGATG-AAATCTTA-CAACGTCC-3'; SEQ ID NO:7) and reverse (5'-CTAGCTAGCTCA-GACCATGGAGTGGTTA-3'; SEQ ID NO:8) primers. The PCR product was then digested and inserted into the XhoI and NheI site (between genes G and L of VSV) of the VSV-IFN-β vector. VSV-mTYRP-1 was generated by inserting TYRP-1 between the G and L genes. Viruses were generated from BHK cells by co-transfection of pVSV-XN2-cDNA library DNA along with plasmids encoding viral genes as described elsewhere (Fernandez et al., *J. Virol.*, 76:895-904 (2002)). Virus was expanded by a single round of infection of BHK cells and purified by sucrose gradient centrifugation.

IFN Gamma Assay

Splenocytes/LN from C57BL/6 mice bearing s.c. B16 tumors and treated with PBS alone or with either VSV-GFP, VSV-mTYRP-1, VSV-mIFN-β-TYRP-1, or VSV-mIFN-β were harvested. Splenocytes were re-stimulated in vitro with PBS, VSV N peptide VSV-N52-59 (RGYVYQGL; SEQ ID NO:9) or with synthetic H-2Kb-restricted melanoma peptides: murine TRP-1222-229 (TAYRYHLL, SEQ ID NO:10; or TWYRYHLL SEQ ID NO:11; TAY, TWY, respectively), TRP-2180-188 (SVYDFFVWL, SEQ ID NO:12; TRP2), murine gp100 (EGSRNQDWL, SEQ ID NO:13; mgp100), or human gp10025-33 (KVPRNQDWL, SEQ ID NO:14; hgp100). Forty eight hours later, supernatants were assayed for IFN-γ by ELISA (FIG. 21).

In Vivo Results $5 \times 10^5$ B16-ova tumor cells in 100 μL of PBS were injected into the flanks of C57BL/6 mice (7 mice per treatment group). Seven days later, mice were treated intratumorally (IT) with PBS, VSV encoding antigens, or VSV-GFP at $7 \times 10^8/50$ μL for three days every other day (FIG. 22). Survival times were determined (FIG. 23).

These results demonstrate that the combined use of a VSV vector encoding an antigen (e.g., TYRP-1) with IFN-β results in prolonged cancer survival and also enhanced IFN-γ response.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising nucleic acid encoding an HIF-2α antigen, a SOX-10 antigen, and a C-MYC antigen, wherein said composition comprises less than 100 separate nucleic acid molecules.

2. The composition of claim 1, wherein said composition comprises a nucleic acid molecule encoding said HIF-2α antigen, a nucleic acid molecule encoding said SOX-10 antigen, and a nucleic acid molecule encoding said C-MYC antigen.

* * * * *

SEQUENCE LISTING

<160> NUMBER OF SEQ ID NOS: 17

<210> SEQ ID NO 1
<211> LENGTH: 32
<212> TYPE: DNA
<213> ORGANISM: Homo sapiens

<400> SEQUENCE: 1
atctcgagat ggatctggtg ctaaaaagat gc                                    32

<210> SEQ ID NO 2
<211> LENGTH: 26
<212> TYPE: DNA
<213> ORGANISM: Homo sapiens

<400> SEQUENCE: 2
atgctagctc agacctgctg cccact                                           26

<210> SEQ ID NO 3
<211> LENGTH: 20
<212> TYPE: DNA
<213> ORGANISM: Mus musculus

<400> SEQUENCE: 3
tcatgaccac agtccatgcc                                                  20

<210> SEQ ID NO 4
<211> LENGTH: 20
<212> TYPE: DNA
<213> ORGANISM: Mus musculus

<400> SEQUENCE: 4
tcagctctgg gatgaccttg                                                  20

<210> SEQ ID NO 5
<211> LENGTH: 8
<212> TYPE: PRT
<213> ORGANISM: Mus musculus

<400> SEQUENCE: 5

Ser Ile Ile Asn Phe Glu Lys Leu
1               5

<210> SEQ ID NO 6
<211> LENGTH: 55
<212> TYPE: DNA
<213> ORGANISM: Mus musculus

<400> SEQUENCE: 6
gaccagacag ggtgttgaag atgcttttta cacactggta agagaaatac gccag           55

<210> SEQ ID NO 7
<211> LENGTH: 60
<212> TYPE: DNA
<213> ORGANISM: Vesicular stomatitis virus

<400> SEQUENCE: 7
tgagctagcc agattcttca tgtttggacc aaatcaactt gtgataccat gctcaaagay 60

<210> SEQ ID NO 8
<211> LENGTH: 56
<212> TYPE: DNA
<213> ORGANISM: Vesicular stomatitis virus -continued

<400> SEQUENCE: 8
ggcctcaatt atatttgagt ttttaattt tatgaaaaaa actaacagca atcatg  56

<210> SEQ ID NO 9
<211> LENGTH: 24
<212> TYPE: PRT
<213> ORGANISM: Mus musculus

<400> SEQUENCE: 9

Tyr Arg Met Lys Lys Leu Asn Ser Ser Asp Asp Gly Thr Gln Gly Cys
 1               5                  10                  15

Met Gly Leu Pro Cys Val Val Met
            20

<210> SEQ ID NO 10
<211> LENGTH: 62
<212> TYPE: DNA
<213> ORGANISM: Mus musculus

<400> SEQUENCE: 10
accatcgaaa acgcatgggg ctcaagatgt tgatgatgat ggctctgctg gtgcccctgg  60
tc  62

<210> SEQ ID NO 11
<211> LENGTH: 60
<212> TYPE: DNA
<213> ORGANISM: Vesicular stomatitis virus

<400> SEQUENCE: 11
tgagctagcc agattcttca tgtttggacc aaatcaactt gtgataccat gctcaaagay 60

<210> SEQ ID NO 12
<211> LENGTH: 56
<212> TYPE: DNA
<213> ORGANISM: Vesicular stomatitis virus

<400> SEQUENCE: 12
ggcctcaatt atatttgagt ttttaatttt tatgaaaaaa actaacagca atcatg 56

<210> SEQ ID NO 13
<211> LENGTH: 22
<212> TYPE: PRT
<213> ORGANISM: Mus musculus

<400> SEQUENCE: 13

Tyr Thr Ile Lys Arg His Lys Trp Ser Val Leu Lys Ser Arg Lys Leu
1 5 10 15

Ala Tyr Arg Pro Pro Lys
20

<210> SEQ ID NO 14
<211> LENGTH: 66
<212> TYPE: DNA
<213> ORGANISM: Mus musculus

<400> SEQUENCE: 14
gcttcttatc tgattcgtgc cagacgcagt atggatgaag ctaaccagcc tctcctcact 60
gatcag 66

<210> SEQ ID NO 15
<211> LENGTH: 60

-continued

```
<212> TYPE: DNA
<213> ORGANISM: Vesicular stomatitis virus

<400> SEQUENCE: 15
tgagctagcc agattcttca tgtttggacc aaatcaactt gtgataccat gctcaaagay     60

<210> SEQ ID NO 16
<211> LENGTH: 56
<212> TYPE: DNA
<213> ORGANISM: Vesicular stomatitis virus
<400> SEQUENCE: 16
ggcctcaatt atatttgagt ttttaatttt tatgaaaaaa actaacagca atcatg         56

<210> SEQ ID NO 17
<211> LENGTH: 19
<212> TYPE: PRT
<213> ORGANISM: Mus musculus

<400> SEQUENCE: 17

Tyr Gln Cys Tyr Ala Glu Glu Tyr Glu Lys Leu Gln Asn Pro Asn Gln
 1               5                  10                  15

Ser Val Val
```